United States Patent [19]
Takatsu et al.

[11] Patent Number: 6,010,642
[45] Date of Patent: Jan. 4, 2000

[54] AZINE DERIVATIVE, PROCESS FOR THE PREPARATION THEREOF, NEMATIC LIQUID CRYSTAL COMPOSITION AND LIQUID CRYSTAL DISPLAY SYSTEM COMPRISING SAME

[75] Inventors: Haruyoshi Takatsu, Tokyo; Sadao Takehara, Chiba; Kiyofumi Takeuchi; Makoto Negishi, both of Tokyo; Norie Osawa, Saitama; Masashi Osawa, Saitama; Shinji Ogawa, Saitama; Hirokazu Yanagihara, Saitama, all of Japan

[73] Assignee: Dainippon Ink and Chemicals, Inc., Tokyo, Japan

[21] Appl. No.: 08/916,026

[22] Filed: Aug. 21, 1997

[30] Foreign Application Priority Data

| Aug. 22, 1996 | [JP] | Japan | 8-221212 |
| Aug. 30, 1996 | [JP] | Japan | 8-230089 |
| Sep. 11, 1996 | [JP] | Japan | 8-240405 |
| Nov. 19, 1996 | [JP] | Japan | 8-307945 |
| May 30, 1997 | [JP] | Japan | 9-141741 |

[51] Int. Cl.$^7$ .......... C09K 19/06; C09K 19/34; C09K 19/20; C09K 19/12
[52] U.S. Cl. ............... 252/299.6; 252/299.61; 252/299.63; 252/299.66; 252/299.01; 252/299.68; 564/249; 544/298; 544/224; 546/339; 546/341; 549/369; 549/370; 558/411
[58] Field of Search ............ 252/299.6, 299.68, 252/299.66, 299.63, 299.61, 299.01; 564/249; 544/298, 224; 546/341, 339; 549/369, 370; 558/411

[56] References Cited

U.S. PATENT DOCUMENTS

| 3,960,749 | 6/1976 | Fergason | 252/299.68 |
| 4,196,975 | 4/1980 | Mailer et al. | 349/182 X |
| 4,265,784 | 5/1981 | Mailer et al. | 252/299.68 |

FOREIGN PATENT DOCUMENTS

| 2 010 274 | 10/1978 | United Kingdom |
| 2027026 | 2/1980 | United Kingdom |

OTHER PUBLICATIONS

Chemical Abstracts, vol. 124, No. 14, Apr. 1, 1996, abstract No. 190019, Centore R et al: "Crystal structure analysis of some mesogenic cyanoazines".

Chemical Abstracts, vol. 112, No. 19, May 7, 1990, abstract No. 178181, Kadry A M et al.: "Utility of o–sulfamoylbenzhydradie in the synthesis of mixed azines".

Chemical Abstracts, vol. 108, No. 20, May 16, 1988, abstract No. 177668, Sereda S V et al: "Crystal and molecular structure of smectic 4,4'–bis(difluoromethoxy)benzylideneazine, p–F2HCO:C6H4:CH:N:N:CH:C6H 4:OCHF2–p".

*Primary Examiner*—C. H. Kelly
*Attorney, Agent, or Firm*—Armstrong, Westerman, Hattori, McLeland & Naughton

[57] ABSTRACT

Disclosed is to provide an azine derivative as a novel liquid crystal compound, a novel process for the preparation of an asymmetrical azine in a high reaction yield with an extremely small amount of by-products such as symmetrical azines, a nematic liquid crystal composition containing the azine derivative which exhibits a broad driving temperature range and an excellent response for the desired high birefringence index, a liquid crystal display device such as TN-LCD, STN-LCD and TFT-LCD having improved electro-optical properties comprising the liquid crystal composition as a constituent material, and a light-scattering type liquid crystal display system which exhibits a suppressed memory phenomenon, a higher uniformity in turbidity for display and improved display properties and response against temperature change while maintaining and improving the required display properties such as fast switching time, lower voltage driving, higher light-control layer resistivity and higher contrast ratio even in the foregoing light-scattering type liquid crystal display system.

20 Claims, No Drawings

AZINE DERIVATIVE, PROCESS FOR THE PREPARATION THEREOF, NEMATIC LIQUID CRYSTAL COMPOSITION AND LIQUID CRYSTAL DISPLAY SYSTEM COMPRISING SAME

FIELD OF THE INVENTION

The present invention relates to an azine derivative useful as an organic electronic material, medicine or agricultural chemicals, particularly as a nematic liquid crystal material for electro-optical liquid crystal display device, a process for the preparation of such an azine derivative, a nematic liquid crystal composition comprising such an azine derivative and a liquid crystal display system comprising such an azine derivative.

BACKGROUND OF THE INVENTION

Liquid crystal display devices have been used in watch and electronic calculator as well as in various measuring instrument, automobile panels, word processors, electronic notebooks, printers, computers and television sets more and more. As typical liquid crystal display systems there are employed TN (twisted nematic) system, STN (super twisted nematic) system, DS (dynamic light scattering) system, GH (guest host) system, FLC (ferroelectric liquid crystal) system, etc. Referring to driving system, multiplex driving system has been popular in place of conventional static driving system. Further, simple matrix system has been popular. In recent years, active matrix system has been put into practical use. Various properties have been required for liquid crystal materials depending on the display system or driving system. Thus, a large number of liquid crystal compounds have been synthesized so far.

Among these liquid crystal compounds, azine derivatives represented by the general formula (A):

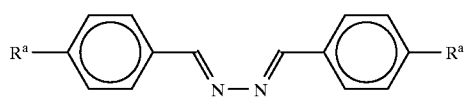

(A)

wherein $R^a$ represents an alkyl group have been known for a relatively long period of time. These liquid crystal materials are excellent as follows:

(i) The upper liquid crystal phase temperature limit $T_{N-1}$ is high;

(ii) The chemical stability of these liquid crystal materials is relatively high; and (iii) These liquid crystal materials can be prepared easily at a low cost.

However, the compounds (A) are disadvantageous in that they have a high melting point.

As a compound which can give solution to these problems there has been reported in JP-A-54-87688 (The term "JP-A" as used herein means an "unexamined published Japanese patent application") an asymmetrical azine represented by the following general formula (B):

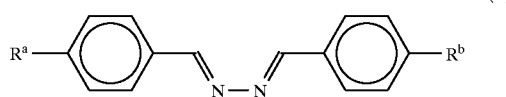

(B)

wherein $R^a$ represents an alkyl group; and Rb represents an alkyl group different from $R^a$. The compound (B) exhibits an upper liquid crystal phase temperature limit as high as the compound (A). In addition, the compound (B) exhibits a lower melting point than the compound (A).

Further, the above cited JP-A-54-87688 discloses an asymmetrical azine as a cyanobenzene derivative represented by the following general formula (C):

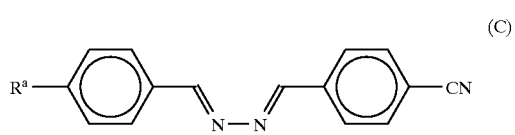

(C)

wherein $R^a$ represents an alkyl group.

However, azine derivatives having alkenyl groups as side chains, azine derivatives containing trans-1,4-cyclohexylene group or fluorine-substituted 1,4-phenylene group, azine derivatives having fluorine atom or -OCF$_3$ as a polar grouop which are expected to exhibit a lower viscosity or azine derivatives of three ring system which are expected to exhibit higher clearing point have never been known.

No processes for the preparation of an asymmetrical azine compound such as the foregoing compounds (B) and (C) have been established. For example, the above cited JP-A-54-87688 merely discloses an ordinary process for the preparation of azines but doesn't disclose detailed examples of preparation. According to the ordinary process for the preparation of azines, a hydrazone represented by the following general formula (A1):

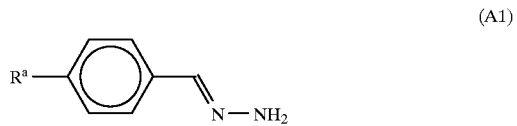

(A1)

wherein $R^a$ is as defined above is reacted with a benzaldehyde derivative represented by the following general formula (A2):

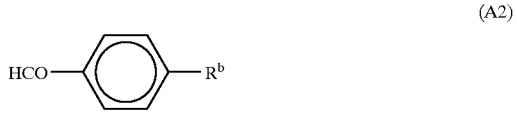

(A2)

wherein $R^b$ is as defined above to prepare an azine.

However, during the reaction or post-treatment, disproportionation occurs to produce symmetrical azines represented by the following general formula (A3):

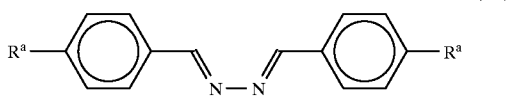

wherein $R^a$ is as defined above or the following general formula (A4):

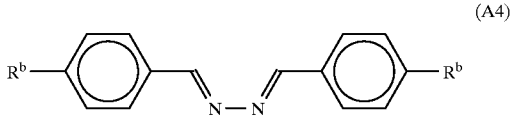

wherein $R^b$ is as defined above in a relatively large amount as by-products besides the desired azines. Further, the preparation of the hydrazone (A1) is often liable to the production of symmetrical azines (A3) during the post-treatment. These symmetrical azines exhibit a good crystallinity and a high melting point similar to the foregoing compound (A) and thus can often hardly be separated and removed away by recrystallization. Further, these symmetrical azines have a poor miscibility with other liquid crystal compounds. Therefore, if the azine derivative thus obtained is used with these symmetrical azines left unseparated, these symmetrical azines can separate out in the composition. In particular, if as $R^a$ or $R^b$ there is used a cyano group or halogen atom, the properties of the product are drastically deteriorated, causing a big problem. Thus, in order to practically use the azines, it is preferred that the azines be free of symmetrical azines (A3) or (A4). Thus, preparation processes which produce no symmetrical azines as by-products are required.

In recent years, for the purpose of improving the response of STN-LCD, an active addressing driving system [Proc. 12th IDRC p. 503, 1992] and a multiline addressing driving system [SID '92 Digest, p. 232, 1992] have been proposed. These driving systems require liquid crystal materials having an elastic constant ratio $K_{33}/K_{11}$ of about 1.5 and a relatively small dielectric anisotropy and viscosity as well as a great birefringence index in particular. Further, for the purpose of accomplishing a brighter display or a higher contrast ratio, a novel reflective type color liquid crystal display system utilizing the birefringence of liquid crystal and phase difference plate instead of a color filter layer [Technical Report of Society of Television Engineering, vol. 14, No. 10, p. 51, 1990] and a liquid display system having a reflective surface provided with small parabolic surfaces on the substrate electrode side have been proposed. These display devices require a liquid crystal material having birefringence properties which produce a greater phase difference due to difference in the wavelength of light or optical birefringence properties which maintain a high contrast even in a wide viewing angle. Further, for various purposes such as miniaturization, portability and increase of the number of pixels, liquid display devices having a broader operating temperature range have been required. These liquid display devices require a liquid crystal material having an elastic constant $K_{11}$ of from 10 to 25, a good chemical stability and a broader nematic temperature and capable of shortening its switching time. Thus, a liquid crystal material having various physical properties which are comprehensively optimized has been required. The proposal of new liquid crystal compositions is still required.

Because of their excellent display quality, active matrix liquid crystal display systems have been on the market of portable terminals, flat panel display, projector, computer, etc. In the active matrix display system, TFT (thin film transistor), MIM (metal insulator metal) or the like is provided every pixel. In this system, emphasis has been placed on the high voltage holding ratio. Further, Kondo et al. proposed a super TFT combined with IPS mode to obtain an even wider viewing angle [Asia Display '95 Digest, p. 707, 1995] (The liquid crystal display device of these active matrix display systems will be hereinafter generically referred to as "TFT-LCD"). In order to cope with such a display device, new liquid crystal compounds or liquid crystal compositions have been still proposed as in JP-A-6-312949 and U.S. Pat. No. 5,480,581.

As a liquid crystal device requiring no polarizer or alignment treatment and producing a bright image with a high contrast there has been known a liquid crystal display device having polymer-encapsulated liquid crystal type. U.S. Pat. Nos. 4,605,284 and 4,435,047 propose gelatin, gum arabic, polyvinyl alcohol, etc. as capsulating substance. These liquid crystal display devices are also known in WO 8504262 and EP-A-205261. These liquid crystal display devices are disadvantageous in that the coincidence or discordance of the individual refractive index of liquid crystal material with the refractive index of polymer must be optimized and a voltage as high as not lower than 25 V is required to obtain a sufficient transparency.

A technique realizing low voltage driving properties, high contrast and multiplex driving properties required for liquid crystal display has been proposed in U.S. Pat. No. 5,304,323. These patents disclose a liquid crystal display device configured such that a liquid crystal material forms a continuous layer in which a polymer substance is distributed in a three-dimensional network.

Referring to liquid crystal materials relating to the foregoing object, European Patent 359,146 discloses a method for optimizing the birefringence index or dielectric anisotropy of liquid crystal materials and JP-A-6-222320 discloses a technique for identifying the elastic constant of liquid crystal materials. Further, U.S. Pat. No. 5,523,127 and EP-A-541912 disclose a liquid crystal material which comprises a fluoro compound to exhibit a contrast of about 40 when used in projection display. However, such a liquid crystal material finds difficulty in satisfying all the requirements, i.e., high resistivity, excellent voltage holding ratio, low driving voltage, strong light scattering that gives a high contrast ratio, fast switching time and good temperature characteristics. Thus, new proposals are still made.

In order to improve the foregoing liquid crystal display properties, a liquid crystal material having a desired birefringence index is required. Further, such a liquid crystal material also needs to have a higher chemical stability, a lower viscosity, a fast response time and a broader driving temperature range. The technique concerning the azine derivative of the general formula (I) of the present invention and its analogous compounds is referred to in, e.g., JP-A-54-87688. However, the knowledge of a mixture containing an azine derivative of the general formula (I) is not yet fully reported. Further, no liquid crystal materials or mixtures having properly adjusted birefringence index, dielectric anisotropy, elastic constant and other properties useful for TN-LCD, STN-LCD and TFT-LCD have been reported.

Further explaining, JP-A-54-87688 proposes the use of a compound represented by any one of the following general formulae (a-1) to (a-4):

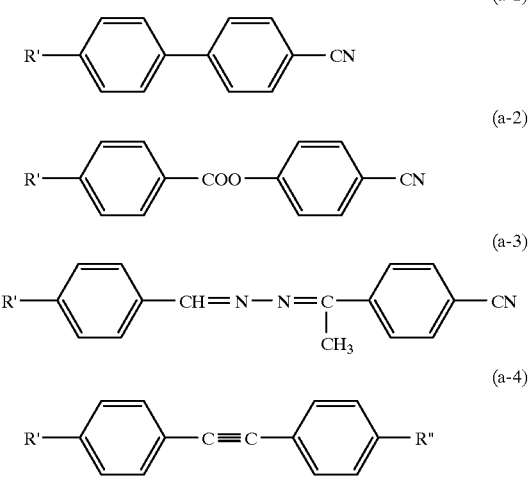

wherein R' and R" each independently represent an alkyl group or alkoxyl group as a compound having a positive dielectric anisotropy. However, the foregoing problems are left unsolved.

SUMMARY OF THE INVENTION

An object of the present invention is to provide an azine as a novel liquid crystal compound which can accomplish the foregoing objects. Another object of the present invention is to provide a novel process for the preparation of an asymmetrical azine in a high reaction yield with an extremely small amount of by-products such as symmetrical azines.

A further object of the present invention is to give solution to the foregoing problems, i.e., provide a nematic liquid crystal composition containing an azine derivative which exhibits a broad driving temperature range and an excellent response for the desired high birefringence index. A still further object of the present invention is to provide a liquid crystal display device such as TN-LCD, STN-LCD and TFT-LCD having improved electro-optical properties comprising such a liquid crystal composition as a constituent material.

A further object of the present invention is to provide a light-scattering type liquid crystal display system which exhibits a suppressed memory phenomenon, a higher uniformity in turbidity for display and improved display properties and response against temperature change while maintaining and improving the required display properties such as fast switching time, lower voltage driving, higher light-control layer resistivity and higher contrast ratio even in the foregoing light-scattering type liquid crystal display system.

The present invention will be further described hereinafter.

The present invention provides a compound, represented by the following general formula (I):

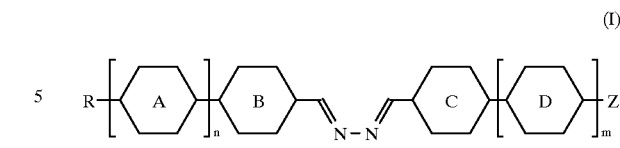

wherein
m and n each independently represent an integer of 0 ir 1;
rings A, B, C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group;
R represents a $C_{1-12}$ alkyl group or alkoxyl group, $C_{2-12}$ alkenyl group or alkoxylalkyl group or $C_{3-12}$ alkenyloxy group; and
Z represents a fluorine atom, chlorine atom, bromine atom, cyano group, $-OCF_3$, $-OCF_2H$, $-CF_3$, $-OCH_2CF_3$, $C_{1-12}$ alkyl group or alkoxyl group, $C_{2-12}$ alkenyl group or alkoxylalkyl group or $C_{3-12}$ alkenyloxy group,
with the proviso that Z is not an alkyl group, cyano group, fluorine atom, chlorine atom or bromine atom when m and n each are 0 and rings B and C each are 1,4-phenylene group and R is an alkyl group.

DETAILED DESCRIPTION OF THE INVENTION

An example of the azine derivative represented by the general formula (I) will be described hereinafter.

The azine derivative represented by the general formula (I) is preferably one represented by the following general formula (Ia):

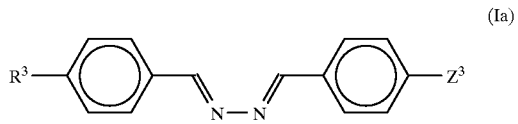

wherein $R^3$ represents a $C_{1-12}$ alkyl group or alkoxyl group; and $Z^3$ represents a fluorine atom, chlorine atom, $-OCF_3$, $-OCFZH$, $-CF_3$ or $-OCH_2CF_3$. Preferably, $Z^3$ is a fluorine atom or $-OCF_3$. More preferably, $R^3$ is a $C_{1-7}$ straight-chain alkyl group. This compound exhibits a lower viscosity than the compound of the foregoing general formula (C) and thus is suitable for fast response.

Similarly, the azine derivative of the present invention is preferably one represented by the following general formula (Ib):

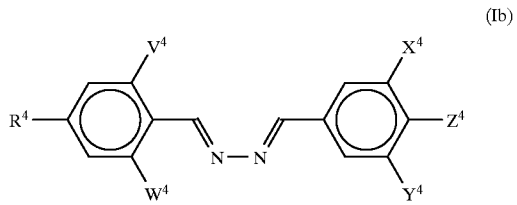

wherein $R^4$ represents a $C_{1-12}$ alkyl group or alkoxyl group; $V^4$, $W^4$, $X^4$ and $Y^4$ each independently represent a fluorine atom or hydrogen atom, with the proviso that at least one of $V^4$, $W^4$, $X^4$ and $Y^4$ represents a fluorine atom; and $Z^4$ represents a fluorine atom, chlorine atom, —OCF$_3$, —OCF$_2$H, —CF$_3$, —OCH$_2$CF$_3$, cyano group, C$_{1-12}$ alkyl group, alkoxyl group or C$_{3-12}$ alkenyloxy group.

In the foregoing compound, $R^4$ is preferably a C$_{1-7}$ alkyl group or alkoxyl group, more preferably a C$_{1-5}$ straight-chain alkyl group. $Z^4$ is preferably a fluorine atom, chlorine atom, —OCF$_3$ or cyano group if the compound of the present invention is used as a P type liquid crystal or is preferably a C$_{1-5}$ alkyl group or alkoxyl group, more preferably a straight-chain alkyl group, if the compound of the present invention is used as an N type liquid crystal. At least one of $V^4$, $W^4$, $X^4$ and $Y^4$ represents a fluorine atom. In particular, $X^4$ is preferably a fluorine atom. In order to drive at a lower voltage, it is preferred that at least two of $V^4$, $W^4$, $X^4$ and $Y^4$ are a fluorine atom.

Similarly, the azine derivative of the present invention is preferably one represented by the following general formula (Ic):

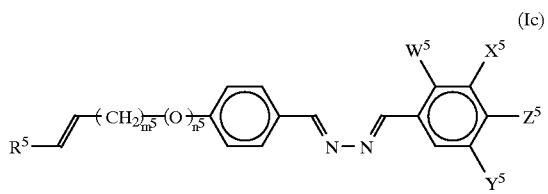

(Ic)

wherein $R^5$ represents a hydrogen atom or C$_{1-12}$ alkyl group, with the proviso that the double bond is trans-positioned when $R^5$ is an alkyl group; $m^5$ represents an integer of from 1 to 10; $n^5$ represents an integer of 0 or 1; $X^5$, $Y^5$ and $W^5$ each independently represent a fluorine atom, chlorine atom, methyl group, cyano group or hydrogen atom; and $Z^5$ represents a fluorine atom, chlorine atom, cyano group, C$_{1-12}$ alkyl group or alkoxyl group or C$_{3-12}$ alkenyl group or alkenyloxy group, with the proviso that one or more hydrogen atoms contained in these groups may be replaced by fluorine atoms.

In the foregoing compound, $R^5$ is more preferably a hydrogen atom or C$_{1-3}$ alkyl group, particularly a hydrogen atom. The suffix $m^5$ is preferably an integer of from 2 to 6, particularly 2. The suffix $n^5$ is preferably 0. $X^5$, $Y^5$ and $W^5$ each independently is preferably a fluorine atom or hydrogen atom. It is preferred that at least one of $X^5$, $Y^5$ and $W^5$ is a hydrogen atom. $Z^5$ is preferably a fluorine atom, C$_{1-7}$ straight-chain alkyl group, C$_{4-7}$ straight-chain alkenyl group, trifluoromethoxy group, trifluoromethyl group, difluoromethoxy group or 2,2,2-trifluoromethoxy group, more preferably a C$_{1-7}$ straight-chain alkyl group or C$_{4-7}$ straight-chain 3-alkenyl group. This compound exhibits a low viscosity, a good solubility and an upper nematic phase temperature limit and thus is useful for liquid crystal material requiring a fast response.

Similarly, the azine derivative of the present invention is preferably one represented by the following general formula (Id):

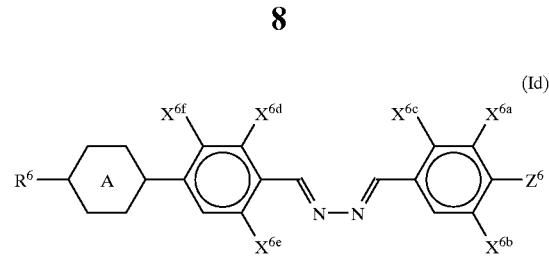

(Id)

wherein $R^6$ represents a C$_{1-20}$ alkyl group or alkoxyl group; ring A represents 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; $X^{6a}$ to $X^{6f}$ each independently represent a hydrogen atom or fluorine atom; Z represents a fluorine atom, chlorine atom, bromine atom, hydrogen atom, cyano group, —OCF$_3$, —OCF$_2$H, —CF$_3$, —OCH$_2$CF$_3$, C$_{1-20}$ alkyl group, alkoxyl group, C$_{2-12}$ alkenyl group or C$_{3-12}$ alkenyloxy group. Ring A is preferably 1,4-phenylene group which may be substituted by fluorine atom or trans-1,4-cyclohexylene group. Further, $X^{6c}$ to $X^{6f}$ each are preferably a fluorine atom. $R^6$ is preferably a C$_{1-7}$ straight-chain alkyl group. In the foregoing compound, Z more preferably represents a fluorine atom, trifluoromethoxy group, C$_{1-7}$ straight-chain alkyl group or C$_{4-7}$ straight-chain alkenyl group. This compound exhibits higher clearing point and hence a broad temperature range in which nematic phase can exhibit. Thus, this compound can extend the nematic phase temperature range when added to a liquid crystal material in a small amount. This compound can occur in the form of various compounds depending on the selection of ring A, $R^6$ and $X^1$ to $X^6$. Preferred among these compounds are those represented by the following general formulae (Id-1) to (Id-9):

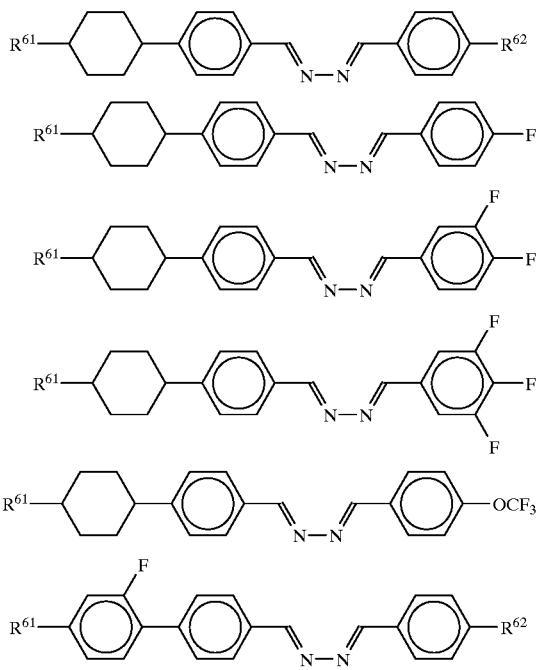

-continued

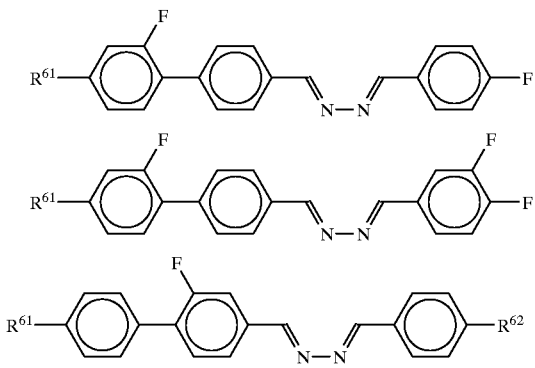

wherein $R^{61}$ represents a $C_{1-7}$ straight-chain alkyl group; $R^{62}$ represents a $C_{1-7}$ straight-chain alkyl group or $C_{4-7}$ straight-chain alkenyl group. Particularly preferred among these compounds are those represented by the general formulae (Id-1) to (Id-3).

Similarly, the azine derivative of the present invention is preferably one represented by the following general formula (Ie):

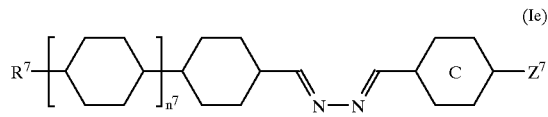

wherein $R^7$ represents a $C_{1-12}$ alkyl group or $C_{2-12}$ alkenyl group or alkoxyl group; $n^7$ represents an integer of 0 or 1; ring C represents 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; and $Z^7$ represents a fluorine atom, chlorine atom, bromine atom, hydrogen atom, cyano group, —OCF$_3$, —OCF$_2$H, —CF$_3$, —OCH$_2$CF$_3$, $C_{1-12}$ alkyl group, alkoxyl group, $C_{2-12}$ alkenyl group, alkoxylalkyl group or $C_{3-12}$ alkenyloxy group. While the conventional azine derivatives assume a light yellow color, this compound is colorless.

The present invention provides a novel process for the preparation of the azine derivative of the general formula (I). In particular, the preparation process of the present invention is suitable for the preparation of an asymmetrical azine derivative.

In accordance with the preparation process of the present invention, a compound represented by the general formula (I):

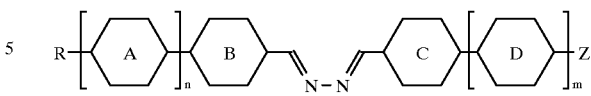

wherein m and n each independently represent an integer of 0 or 1; rings A, B, C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; R represents a $C_{1-12}$ alkyl group or alkoxyl group, $C_{2-12}$ alkenyl group or alkoxylalkyl group or $C_{3-12}$ alkenyloxy group; and Z represents a fluorine atom, chlorine atom, bromine atom, cyano group, —OCF$_3$, —OCF$_2$H, —CF$_3$, —OCH$_2$CF$_3$, $C_{1-12}$ alkyl group or alkoxyl group, $C_{2-12}$ alkenyl group or alkoxylalkyl group or $C_{3-12}$ alkenyloxy group, can be easily prepared by allowing a compound represented by the following general formula (II):

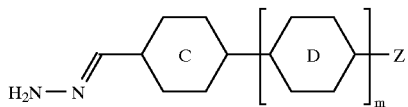

wherein Z represents a fluorine atom, chlorine atom, bromine atom, cyano group, —OCF$_3$, —OCF$_2$H, —CF$_3$, —OCH$_2$CF$_3$, $C_{1-12}$ alkyl group or alkoxyl group, $C_{2-12}$ alkenyl group or alkoxylalkyl group or $C_{3-12}$ alkenyloxy group; rings C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; and m represents an integer of 0 or 1 and a compound represented by the following general formula (III):

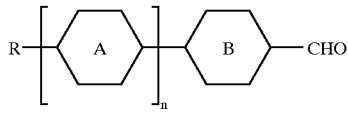

wherein R represents a $C_{1-12}$ alkyl group or alkoxyl group, $C_{2-12}$ alkenyl group or alkoxylalkyl group or $C_{3-12}$ alkenyloxy group; rings A and B each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; and n represents an integer of 0 or 1 to undergo reaction in the presence of an amine.

In accordance with the preparation process described in JP-A-54-87688, a symmetrical azine derivative represented by the following general formula (A5) or (A6) is produced:

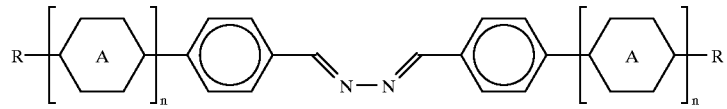

-continued

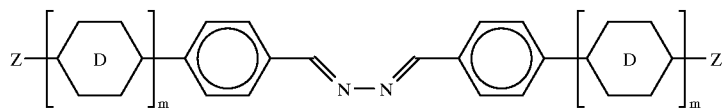
(A6)

wherein R, Z, rings A, B, C and D, m and n are as defined in the general formula (I). However, these symmetrical azines exhibit a good crystallinity and a high melting point and thus can often be hardly separated and removed away by recrystallization. Further, since these symmetrical azines exhibit a poor miscibility with other liquid crystal compounds, they, if left unremoved, can separate out in the composition. In particular, if as R or Z there is used a cyano group or halogen atom, these symmetrical azines exhibit drastically deteriorated properties which cause a big problem.

Accordingly, the preparation process of the present invention comprising the actual use of the compound of the general formula (I) requires a high yield reaction process involving the production of an extremely small amount of by-products such as the foregoing symmetrical azines. In order to inhibit the production of symmetrical azines, the reaction is preferably effected in the presence of an amine.

As the foregoing amine there is preferably used a secondary amine or tertiary amine, particularly tertiary amine. Examples of the tertiary amine employable herein include trialkylamine such as triethylamine, trimethylamine and tributylamine, aromatic amine such as N,N-dimethylaniline and N,N-diethylaniline, and cyclic amine such as pyridine. Particularly preferred among these amines is trialkylamine such as triethylamine.

The amount of the amine to be used is preferably from 0.1 to 20 mols, more preferably from 0.5 to 10 mols per mol of the hydrazone of the general formula (II).

Such an amine may be added to the system during the reaction of the hydrazone of the general formula (II) with the benzaldehyde of the general formula (III). Alternatively, such an amine may be added to the system during the treatment after the preparation of the hydrazone of the general formula (II) so that the hydrazone containing an amine can be reacted with the benzaldehyde of the general formula (III). In some detail, a benzaldehyde derivative represented by the following general formula (IV):

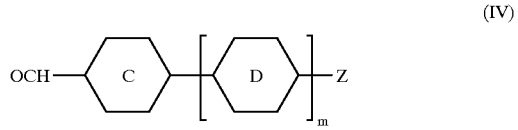
(IV)

wherein Z, m, and rings C and D are as defined in the general formula (II) is reacted with a large excess of the hydrazine in a solvent such as dichloromethane to prepare the hydrazone of the general formula (II). After the termination of the reaction, the reaction product is repeatedly washed with an aqueous basic solution such as saturated aqueous solution of sodium bicarbonate to remove excess hydrazine. To the solution is then added a tertiary amine. To the solution is then added a dehydrating agent such as anhydrous sodium sulfate so that it is dehydrated. The solution thus dehydrated is then added to a dichloromethane solution of the benzaldehyde of the general formula (III) in the presence of a basic alumina so that they are reacted. This reaction may be effected under cooling or heating. In practice, however, this reaction is preferably effected in the vicinity of room temperature. After the termination of the reaction, the reaction product is immediately purified through column chromatography with a basic alumina to give a purified product which is then optionally recrystallized from a polar solvent such as ethanol to obtain the desired compound.

Alternatively, the compound of the general formula (I) of the present invention can also be obtained by reacting a hydrazone of the following general formula (V):

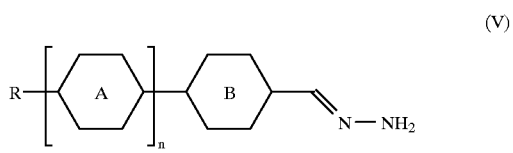
(V)

wherein R, n, and rings A and B are as defined in the general formula (III) instead of the hydrazone of the general formula (II) with the benzaldehyde of the general formula (IV) in the same manner as described above.

Many of benzaldehyde derivatives to be used as starting material are commercially and easily available. Those which are not commercially available, if necessary, can be easily obtained by reacting a Grignard reagent prepared from the corresponding phenyl bromide derivative with a formylating agent such as N,N-dimethylformaldehyde (DMF). These benzaldehyde derivatives can also be obtained by converting the corresponding benzoic acid derivative to an acid chloride, and then reducing the acid chloride.

Examples of the azine derivative of the present invention containing those of general formula (I) thus prepared will be set forth in Table 1 below with their phase transition temperature.

| No. | R | n | A | B | C | D | m | Z | Phase transition temperatures |
|---|---|---|---|---|---|---|---|---|---|
| No. 1 | C₂H₅ | 0 | — |  |  | — | 0 | F | Cr 63.5 N 68 I |
| No. 2 | n-C₃H₇ | 0 | — |  |  | — | 0 | F | Cr 70.5 N 96.5 I |
| No. 3 | n-C₃H₇ | 0 | — |  |  | — | 0 | F | Cr 56.5 N 84 I |
| No. 4 | n-C₃H₇ | 0 | — |  |  | — | 0 | OCF₃ | Cr 93 S 95 SA 98 N 105 I |
| No. 5 | n-C₃H₇ | 0 | — |  |  | — | 0 | CH₃ | Cr 68.5 N 102 I |
| No. 6 | n-C₃H₇ | 0 | — |  |  | — | 0 | C₂H₅ | Cr 62 N 95.5 I |
| No. 7 | n-C₃H₇ | 0 | — |  | 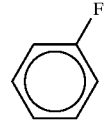 | — | 0 | F | Cr 50 N 59.5 I |
| No. 8 | n-C₃H₇ | 0 | — |  | 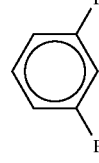 | — | 0 | F | Cr 44 N 51 I |
| No. 9 | n-C₃H₇ | 0 | — |  |  | — | 0 | CH₃ | Cr 82 N 103 I |
| No. 10 | n-C₃H₇ | 0 | — |  |  | — | 0 | 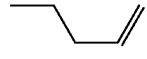 | Cr 57 N 116 I |
| No. 11 | n-C₃H₇ | 0 | — |  |  | — | 0 | F | Cr 66 N 99 I |
| No. 12 | n-C₃H₇ | 1 |  |  |  | — | 0 | CH₃ | Cr 112.5 N 245 I |

-continued

| No. | R | n | A | B | C | D | m | Z | Phase transition temperatures |
|---|---|---|---|---|---|---|---|---|---|
| No. 13 | n-$C_3H_7$ | 1 | hexagon | ring | ring | — | 0 | $C_2H_5$ | Cr 97 N 227 I |
| No. 14 | n-$C_3H_7$ | 1 | hexagon | ring | ring | — | 0 | allyl | Cr 93 N 265.5 I |
| No. 15 | n-$C_3H_7$ | 1 | hexagon | ring | ring | — | 0 | F | Cr 119 N 242 I |
| No. 16 | n-$C_3H_7$ | 1 | hexagon | ring | ring-F | — | 0 | F | Cr 92.5 N 245 I |
| No. 17 | vinyl | 1 | hexagon | ring | ring | — | 0 | $CH_3$ | Cr 110 N 266 I |
| No. 18 | vinyl | 1 | hexagon | ring | ring | — | 0 | $C_2H_5$ | Cr 95 N 264 I |
| No. 19 | vinyl | 1 | hexagon | ring | ring | — | 0 | F | Cr 106 N 255 I |
| No. 20 | vinyl | 1 | hexagon | ring | ring | — | 0 | allyl | Cr 102 N 265 I |
| No. 21 | n-$C_3H_7$ | 0 | — | hexagon | hexagon | — | 0 | n-$C_3H_7$ | Cr 59 N 75.5 I |

(In the table above, Cr stands for crystalline phase, S stands for smectic phase, SA stands for smectic A phase, N stands for nematic phase, and I stands for isotropic liquid phase. Phase transition temperature is represented in ° C.)

Excellent features of the present invention will be described hereinafter.

The compound represented by the formula (D-1)

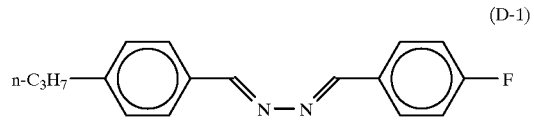

(D-1)

as a known compound in JP-A-54-87688 has the following transition temperature: Cr 70.5 N 96.5 I The comparison of the compound (D-1) with the corresponding compound Nos. 7 and 8 of the present invention set forth in Table 1 in phase transition temperature shows that the compound Nos. 7 and 8 have a melting point as low as about 20° C. and 25° C. lower than that of the compound (D-1). In general, compounds having a high melting point can often undergo phase separation or crystallization in a liquid crystal composition. From this standpoint of view, too, it can be easily appreciated that the compound of the general formula (I) of the present invention is superior to the corresponding compound of the general formula (D-1) in miscibility with conventional liquid crystals.

Further, excellent effects obtained by adding the compound of the general formula (I) to conventional liquid crystal compositions are obvious as follows:

A general-purpose-host liquid crystal (H):

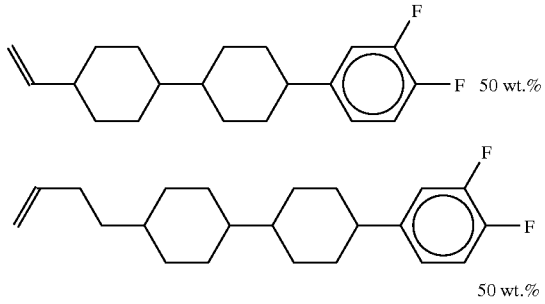

wherein % indicates % by weight was prepared. The host liquid crystal (H) had the following properties:

$T_{N-1}$: 116.7° C.

$T_{-N}$: 11° C.

Switching time: 21.5 msec. (cell thickness: 4.5 μm) 32.5 msec. (cell thickness: 6.0 μm) $V_{th}$: 1.88 (cell thickness: 4.5 μm)

2.14 (cell thickness: 6.0 μm)

$\Delta_n$: 0.09

A liquid crystal composition (M-7) consisting of 80% by weight of the host liquid crystal (H) and 20% by weight of the compound No. 7 of the present invention set forth in Table 1:

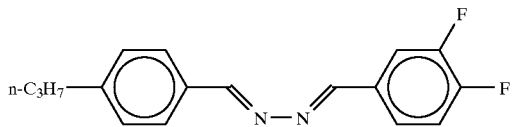

was then prepared.

The liquid crystal composition (M-7) thus prepared exhibited an upper nematic phase temperature limit ($T_{N-1}$) of 98° C. which is about 20° C. lower than that of the host liquid crystal (H). This composition was allowed to stand at a temperature of 0° C. for 24 hours. As a result, no crystallization was observed. This composition was allowed to stand at a temperature of –20° C.so that it was solidified. While being heated, the composition was then measured for temperature ($T_{-N}$) at which it again turns to uniform nematic phase. The results were 9° C. This composition was used to prepare a 4.5 μm cell thickness. The device was then measured for switching time. The results were 14.3 msec., which demonstrates that the response is very fast. The device was also measured for threshold voltage. The results were 1.83 V, which is a slight decrease from that of the host liquid crystal (H).

Similarly, a liquid crystal composition (M-8) consisting of 80% by weight of the general-purpose host liquid crystal (H) and 20% by weight of the compound No. 8:

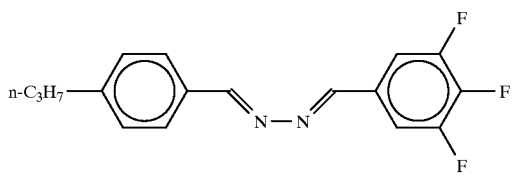

set forth in Table 1 was prepared.

The liquid crystal composition (M-8) thus prepared exhibited an upper nematic phase temperature limit (TN-1) of 91.2° C., which is a decrease from that of the liquid crystal composition (M-7). This composition was then allowed to stand at a temperature of 0° C. for 24 hours. As a result, no crystallization was observed. The composition was then solidified in the same manner as in (M-7). The composition was then measured for T-N in the same manner as in (M-7). The results were 13° C. The composition was then used to prepare an device in the same manner as mentioned above. The device was then measured for switching time. The results were 17.8 msec., which demonstrates that the response is very fast, thought not so high as (M-7). The device was then measured for threshold voltage. The results were 1.54 V, which is a drastic decrease as great as not less than 0.3 V from that of the host liquid crystal (H).

These facts show that the compound of the present invention can exhibit drastically improved miscibility with conventional liquid crystals and switching time when it has fluorine atom incorporated therein as a side substituent. This compound is more useful for the preparation of a liquid crystal composition which can operate in a broad temperature range and exhibits a fast response.

The compounds represented by the following general formulae (A-1), (A-2) and (A-3):

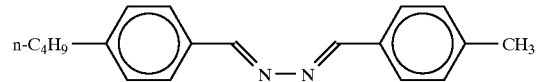

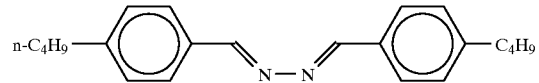

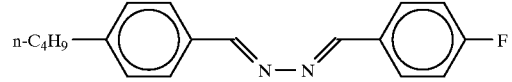

set forth as known compounds in JP-A-54-87688 have the following transition temperatures:

| | | |
|---|---|---|
| (A-1) | Cr 58 | N 87 I |
| (A-2) | Cr 60.5 | N 84 I |
| (A-3) | Cr 56.5 | N 84 I |

The comparison of the compounds of the general formulae (A-1), (A-2) and (A-3) with the corresponding compound Nos. 9, 10 and 11 of the present invention set forth in Table 1 in phase transition temperature shows that the compound of the general formula (I) of the present invention exhibits a sufficiently upper nematic phase temperature limit than the corresponding compound of the general formula (A). In some detail, the compounds No. 9 and No. 11 each exhibit an upper nematic phase temperature limit as high as about 15° C. higher than that of the compound of the general formula (A). The compound No. 10 exhibits an upper nematic phase temperature limit as high as about 30° C. higher than that of the compound of the general formula (A). The introduction of a double bond provides a $T_{N-1}$ increase of about 15° C.

A liquid crystal composition (M-9) consisting of 80% by weight of the host liquid crystal (H) and 20% by weight of the compound No. 9:

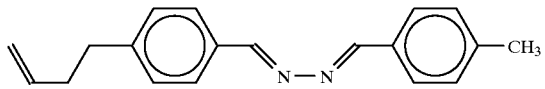

set forth in Table 1 was then prepared. The liquid crystal composition (M-9) thus prepared exhibited an upper nematic phase temperature limit (TN-1) of 118° C., which is a slight increase from that of the host liquid crystal (H). This liquid crystal composition was then allowed to stand at a temperature of 0° C. for 24 hours. As a result, no crystallization was observed. This liquid crystal composition was allowed to stand at a temperature of −20° C. so that it was solidified. While being heated, this liquid crystal composition was measured for temperature at which it again turns to uniform nematic phase ($T_{-N}$). The results were as low as −12° C. A 6.0 μm thick device was prepared from this liquid crystal composition in the same manner as mentioned above. The device thus prepared was then measured for switching time. The results were 30.1 msec., which demonstrates that the response is very fast. The device was also measured for threshold voltage. The results were 2.69 V.

A liquid crystal composition (M-10) consisting of 80% by weight of the host liquid crystal (H) and 20% by weight of the compound No. 10:

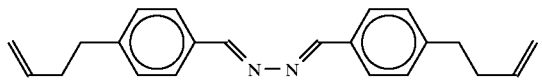

set forth in Table 1 was then prepared. This liquid crystal composition (M-10) exhibited an upper nematic phase temperature limit ($T_{N-1}$) of 119° C., which is a greater increase from that of the host liquid crystal (H) than the liquid crystal composition (M-9). This liquid crystal composition was then allowed to stand at a temperature of 0° C. for 24 hours. As a result, no crystallization was observed. This liquid crystal composition was then solidified in the same manner as in the liquid crystal composition (M-9). This liquid crystal composition was then measured for $T_{-N}$ in the same manner as in the liquid crystal composition (M-9). The results were 5° C. A 6.0 μm thick device was then prepared from this liquid crystal composition in the same manner as mentioned above. The device thus prepared was then measured for switching time. The results were 29.7 msec., which demonstrates that the response is further very fast. This device exhibited a threshold voltage of 2.67 V.

These facts show that the compound of the present invention can exhibit drastically improved miscibility with conventional liquid crystals and switching time when it has an alkenyl group incorporated therein as a side chain. This compound is more useful for the preparation of a liquid crystal composition which-can operate in a broad temperature range and exhibits a fast response.

It was already described that the two-ring azine compound of the present invention has an upper nematic phase temperature limit ($T_{N-1}$). However, as shown in Table 1, a three-ring azine derivative is preferred to obtain a higher $T_{N-1}$. The comparison of these compounds shows that the three-ring azine compound of the present invention exhibits an upper nematic phase temperature limit of not lower than 150° C. higher than that of the corresponding two-ring azine derivative.

Further, excellent effects obtained by adding these three-ring azine compounds to conventional liquid crystal compositions are obvious as follows:

Liquid crystal compositions (M-12), (M-13), (M-14), (M-15) and (M-16) consisting of 80% by weight of the host liquid crystal (H) and 20% by weight of the compounds No. 12, No. 13, No. 14, No. 15 and No. 16:

No. 12

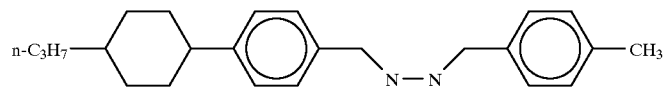

No. 13

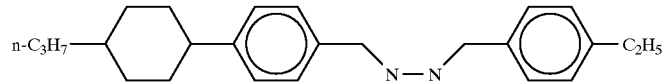

No. 14

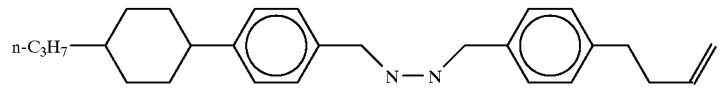

No. 15

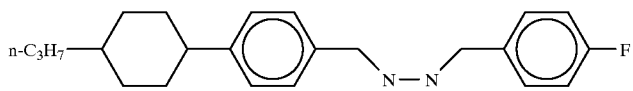

No. 16

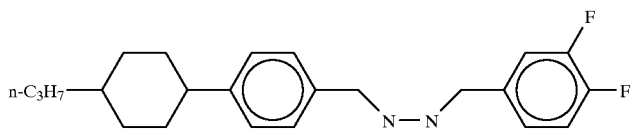

, respectively, were prepared.

The upper nematic phase temperature limit ($T_{N-I}$), melting point ($T_{-N}$), threshold voltage ($V_{th}$), birefringence index ($\Delta n$) and switching time ($\tau$) of the liquid crystal compositions thus prepared and the host liquid crystal (H) are set forth in Table 2.

TABLE 2

Various physical properties of host liquid crystal (H) and liquid crystal compositions

|  | $T_{N-I}(°\,C.)$ | $T_{-N}(°\,C.)$ | $V_{th}(V)$ | $\tau(msec.)$ | $\Delta n$ |
|---|---|---|---|---|---|
| M-12 | 157.2 | −8 | 2.64 | 16.0 | 0.139 |
| M-13 | 152.6 | −5 | 2.54 | 17.4 | 0.137 |
| M-14 | 153.3 | — | 2.69 | 16.3 | 0.136 |
| M-15 | 144.1 | — | 2.42 | 17.0 | 0.131 |
| M-16 | 146.3 | — | 2.07 | 21.0 | 0.128 |
| (H) | 116.7 | 11 | 1.88 | 21.5 | 0.090 |

The liquid crystal composition (M-12) comprising the compound No. 12 as an n-type azine derivative exhibited an upper nematic phase temperature limit of 157.2° C., which is a great increase from that of the host liquid crystal, i.e., 116.7° C. The liquid crystal composition (M-12) exhibited a melting point of −8° C. as compared with that of the host liquid crystal, i.e., 11° C. Thus, the incorporation of 20% by weight of the compound No. 12 as an n-type azine derivative in the host liquid crystal provides a drastic extension of nematic phase temperature range by 59.5° C. This liquid crystal composition was then allowed to stand at a temperature of 0° C. for 24 hours. As a result, no crystallization was observed. A 4.5 μm thick device was prepared from this liquid crystal composition in the same manner as mentioned above. The device thus prepared was then measured for switching time. The results were 16.0 msec., which demonstrates that the response is very fast. The device was also measured for threshold voltage. The results were slightly higher than that of the host liquid crystal (H). The device further exhibited a birefringence index ($\Delta n$) as high as 0.139.

The liquid crystal composition (M-15) was prepared from 20% by weight of the compound No. 15 as a p-type azine derivative and 80% by weight of the host liquid crystal (H). The liquid crystal composition (M-15) thus prepared exhibited an upper nematic phase temperature limit ($T_{N-I}$) of about 30° C. higher than that of the host liquid crystal, i.e., 116.7° C. A liquid crystal device was then prepared from this liquid crystal composition in the same manner as mentioned above. The liquid crystal device thus prepared was then measured for switching time. The results show that the device can respond more rapidly than the host liquid crystal (H), though slightly inferior to those comprising an n-type azine derivative. The device also exhibited a birefringence index ($\Delta n$) as high as 0.131. The device was then measured for threshold voltage. The results show that the device exhibits an improvement in threshold voltage as compared with the liquid crystal compositions (M-12), (M-13) and (M-14) consisting of 80% by weight of the host liquid crystal (H) and 20% by weight of the compounds No. 12, No. 13 and No. 14 as n-type azine derivatives, respectively, though showing a slight increase from that of the host liquid crystal (H).

These facts show that the three-ring compound of the present invention exhibits an excellent miscibility with conventional liquid crystals and a large birefringence index and is very useful for the drastic extension of nematic phase temperature range and the drastic improvement in switching time without increasing the threshold voltage so much.

An example of the nematic liquid crystal composition of the present invention and a liquid crystal display system comprising it will be described below.

The liquid crystal composition of the present invention is a nematic liquid crystal composition comprising as a liquid crystal component A a compound represented by the general formula (I):

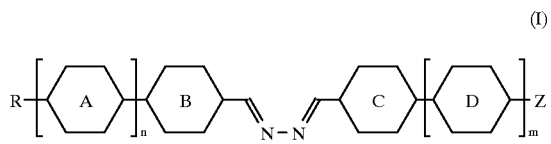

(I)

wherein m and n each independently represent an integer of 0 or 1; rings A, B, C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; R represents a $C_{1-12}$ alkyl group or alkoxyl group, $C_{2-12}$ alkenyl group or alkoxylalkyl group or $C_{3-12}$ alkenyloxy group; and Z represents a fluorine atom, chlorine atom, bromine atom, cyano group, —$OCF_3$, —$OCF_2H$, —$CF_3$, —$OCH_2CF_3$, $C_{1-12}$ alkyl group or alkoxyl group, $C_{2-12}$ alkenyl group or alkoxylalkyl group or $C_{3-12}$ alkenyloxy group, with the proviso that Z is not an alkyl group, cyano group, fluorine atom, chlorine atom or bromine atom when m and n each are 0 and rings B and C each are 1,4-phenylene group and R is an alkyl group. A preferred example of the nematic liquid crystal composition of the present invention is a nematic liquid crystal composition essentially comprising as a liquid crystal component A a compound represented by the general formula (I):

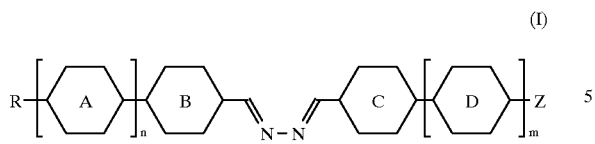
(I)

wherein m and n each independently represent an integer of 0 or 1; rings A, B, C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; R represents a $C_{1-12}$ alkyl group or alkoxyl group, $C_{2-12}$ alkenyl group or alkoxylalkyl group or $C_{3-12}$ alkenyloxy group; and Z represents a fluorine atom, chlorine atom, bromine atom, cyano group, —$OCF_3$, —$OCF_2H$, —$CF_3$, —$OCH_2CF_3$, $C_{1-12}$ alkyl group or alkoxyl group, $C_{2-12}$ alkenyl group or alkoxylalkyl group or $C_{3-12}$ alkenyloxy group and as-a liquid crystal component B a compound having a dielectric anisotropy of not less than +2.

This liquid crystal component A exhibits a relatively low viscosity, a larger birefringence index and a larger elastic constant. Therefore, liquid crystal compositions comprising the liquid crystal component A of the present invention can control a birefringence index and elastic constant in a broad range and can be driven at a fast response.

Further, it was found that the liquid crystal composition of the present invention comprises the liquid crystal component A made of a compound of the general formula (I) in an amount of from 1 to 50% by weight and the liquid crystal component B made of a compound having a dielectric anisotropy of not less than +2 in an amount of from 10 to 90% by weight to have a faster response.

The liquid crystal component A can shift the upper nematic phase temperature limit to a relatively high temperature and exhibit an excellent miscibility when mixed with other liquid crystal materials besides the foregoing properties. Thus, the liquid crystal component A can further extend the display temperature range. Further, the liquid crystal component A exhibits a higher chemical stability. From this standpoint of view, a preferred embodiment of the compound represented by the general formula (I) is one represented by the general formula (I) wherein R represents a methyl group, ethyl group, propyl group, butyl group, pentyl group or 3-butenyl group and/or Z represents a fluorine atom, methyl group, ethyl group, propyl group, butyl group, pentyl group or 3-butenyl group. Specific examples of such a compound include those represented by the following formulae (I-1) to (I-13):

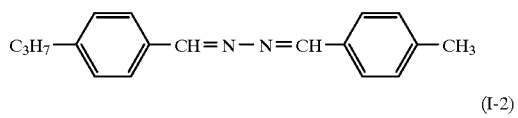
(I-1)

(I-2)

(I-3)

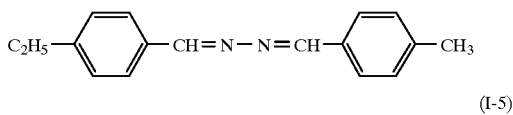
(I-4)

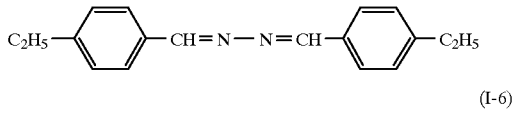
(I-5)

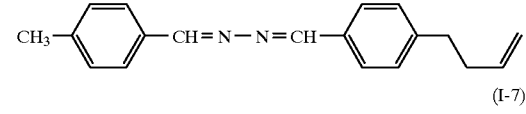
(I-6)

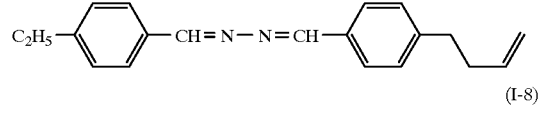
(I-7)

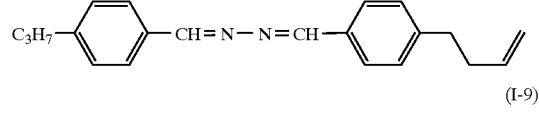
(I-8)

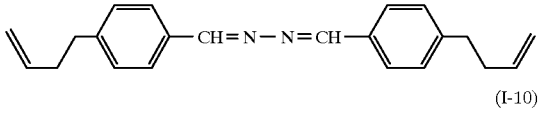
(I-9)

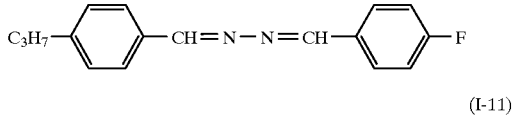
(I-10)

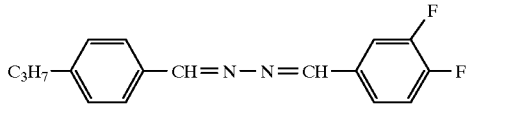
(I-11)

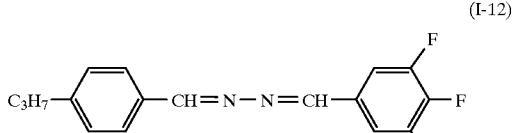
(I-12)

(I-13)

Nematic liquid crystal compositions comprising as the liquid crystal component A one or more such compounds in an amount of from 30 to 100% by weight gave favorable results.

As the liquid crystal component A there may be used one or more compounds of the general formula (I). Even if one compound of the general formula (I) is used, the foregoing effects can be exerted. The liquid crystal composition comprising as the liquid crystal component A at least one compound represented by the general formula (I) provides a liquid crystal display system such as TN-LCD and STN-LCD with improved electro-optical properties, particularly better response time, sharpness and temperature dependence of driving voltage at low temperatures, when incorporated therein as a constituent material.

The liquid crystal composition of the present invention may be in the form of a liquid crystal composition comprising a liquid crystal component B made of one or more compounds having a dielectric anisotropy of not less than +2 in addition to the foregoing liquid crystal component A. The term "liquid crystal compound having a dielectric anisotropy of greater than 2" as used herein has the following meaning. In other words, such a liquid crystal compound has a rod-shaped chemical structure. Such a liquid crystal compound has a core structure having from 1 to 4 6-membered rings at the central portion. The 6-membered rings positioned at both longitudinal ends of the central portion have terminal groups substituted at positions corresponding to the longitudinal position of liquid crystal molecule. At least one of the terminal groups positioned at both ends is a polar group such as —CN, —OCN, —NCS, —F, —Cl, —NO$_2$. —CF$_3$, —OCF$_3$ and —OCHF$_2$. In this arrangement, the optical anisotropy of the liquid crystal layer can be adjusted to a predetermined value that can render the liquid crystal device electrically drivable and operable in a broader temperature range.

As the liquid crystal component B there should be used at least one, preferably from 3 to 15 compounds having a dielectric anisotropy of not less than +2. Further, it is preferred that the liquid crystal component B be properly selected from the group consisting of compounds having a dielectric anisotropy of from +8 to +13, compounds having a dielectric anisotropy of from +14 to +18 and compounds having a dielectric anisotropy of not less than +18. In this manner, predetermined driving voltage and response characteristics can be obtained. In this case, not more than 10 compounds having a dielectric anisotropy of from +8 to +13 are preferably used in admixture, not more than 8 compounds having a dielectric anisotropy of from +14 to +18 are preferably used in admixture, and not more than 10 compounds having a dielectric anisotropy of not less than +18 are preferably used in admixture. The use of the liquid crystal component B in this manner provides a favorable effect on the temperature characteristics of display, i.e., better temperature dependence of driving voltage, contrast related to sharpness, response, etc.

The liquid crystal composotion of the present invention preferably comprises as the liquid crystal component B a compound selected from the group consisting of compounds represented by the following general formulae (II-1) to (II-4):

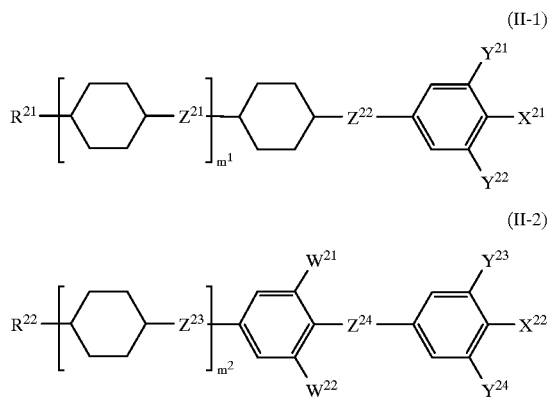

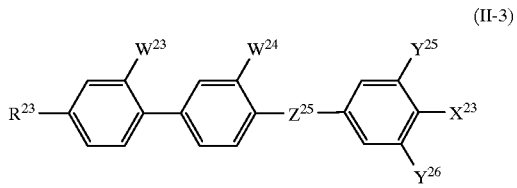

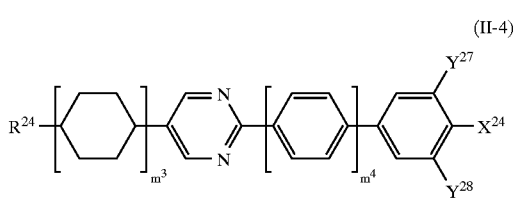

wherein $R^{21}$ to $R^{24}$ each independently represent a $C_{2-10}$ straight-chain alkyl group, alkenyl group or $C_sH_{2s+1}$—O—$C_tH_{2t}$ in which s and t each independently represent an integer of from 1 to 5; $X^{21}$ to $X^{24}$ each independently represent a fluorine atom, chlorine atom, —OCF$_2$, —OCHF$_2$, —CF$_3$ or —CN; $Y^{21}$ $Y^{28}$ each independently represent a hydrogen atom or fluorine atom; $W^{21}$ to $W^{24}$ each independently represent a hydrogen atom or fluorine atom; $Z^{21}$ to $Z^{23}$ each independently represent a single bond, —COO—, —CH$_2$CH$_2$— or —(CH$_2$)$_4$—; $Z^{21}$ may also represent —C≡C— or —CH=CH—; $Z^{24}$ and $Z^{25}$ each independently represent a single bond, —COO—, —C≡C— or —CF=CF—; and $m^1$ to $m^4$ each independently represent an integer of from 0 or 1, with the proviso that $m^3+m^4$ make an integer of 0 or 1, and hydrogen atoms (H) in the cyclohexane ring in the various compounds may be replaced by deuterium atoms (D).

The liquid crystal component B may comprise one compound, preferably from 3 to 15 compounds. Further, the liquid crystal component B preferably comprises compounds selected from the group consisting of compounds of the general formula (II-1) having a dielectric anisotropy of from +8 to +17, compounds of the general formula (II-2) having a dielectric anisotropy of from +25 to +60, compounds of the general formula (II-3) having a dielectric anisotropy of from +10 to +25 and compounds of the general formula (II-4) having a dielectric anisotropy of from +18 to +30. In this manner, predetermined driving voltage and response characteristics can be obtained. In this case, not more than 8 compounds of the general formula (II-1) are preferably used in admixture, not more than 10 compounds of the general formula (II-2) are preferably used in admixture, not more than 8 compounds of the general formula (II-3) are preferably used in admixture, and not more than 6 compounds of the general formula (II-4) are preferably used in admixture. The use of the liquid crystal component B in this manner provides a favorable effect on the temperature characteristics of display, i.e., better temperature dependence of driving voltage, contrast related to sharpness, response, etc.

The liquid crystal component B of the present invention may comprise compounds represented by one or more of the foregoing general formulae (II-1) to (II-4). In this case, the various compounds (II-1) to (II-4) are each incorporated in an amount of from 10 to 100% by weight. Particularly preferred examples of the compounds represented by the foregoing general formulae (II-1) to (II-4) include those represented by the following general formulae (II-1a) to (II-4d):

(II-1a) 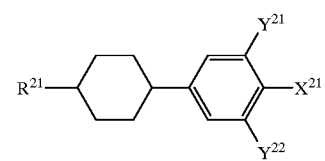
(II-1b) 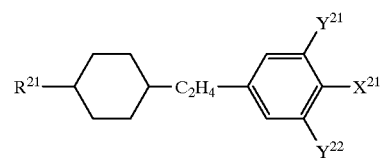
(II-1c) 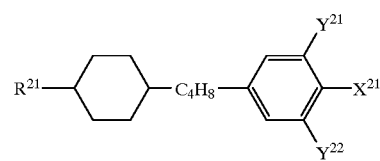
(II-1d) 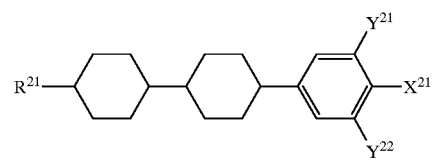
(II-1e) 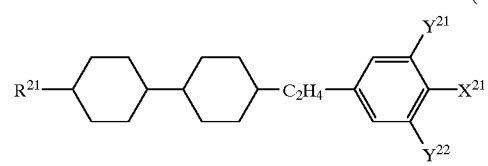
(II-1f) 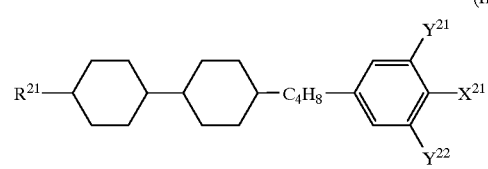
(II-1g) 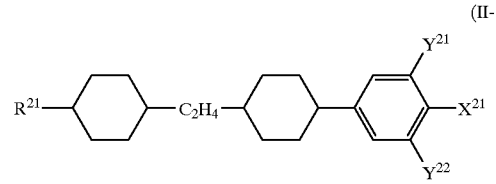
(II-1h) 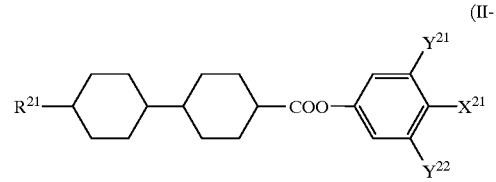
(II-1i) 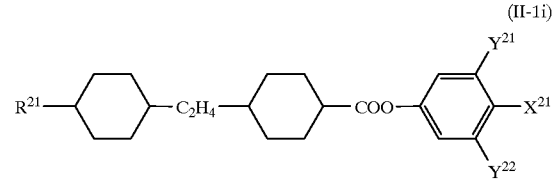
(II-2a) 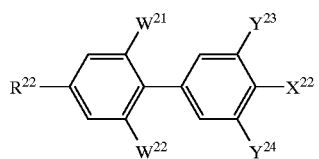
(II-2b) 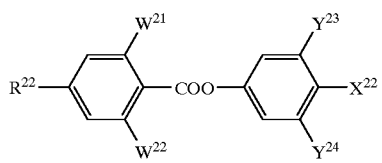
(II-2c) 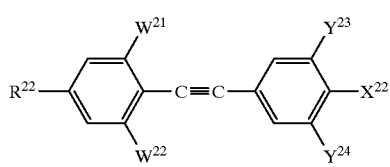
(II-2d) 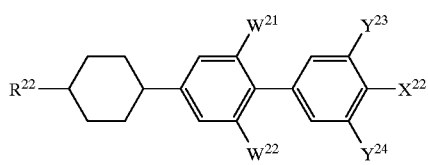
(II-2e) 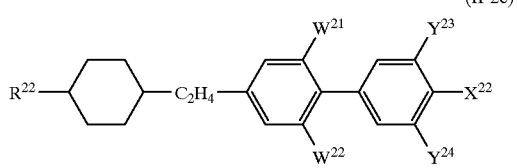
(II-2f) 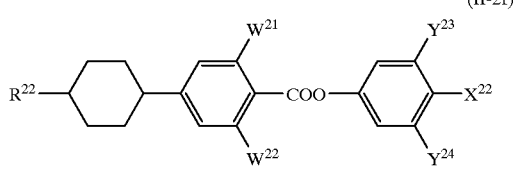
(II-2g) 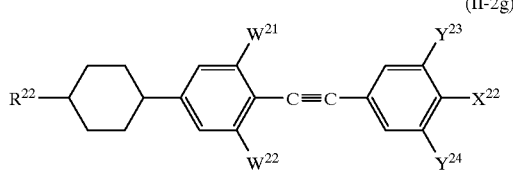
(II-2h) 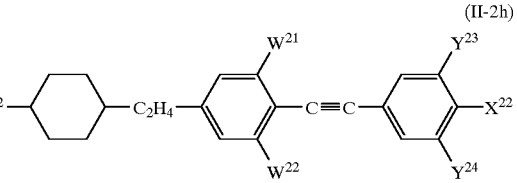
(II-3a) 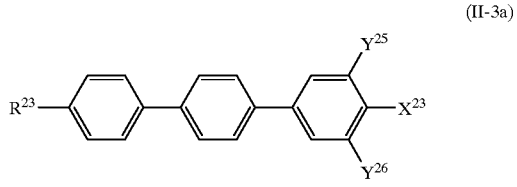

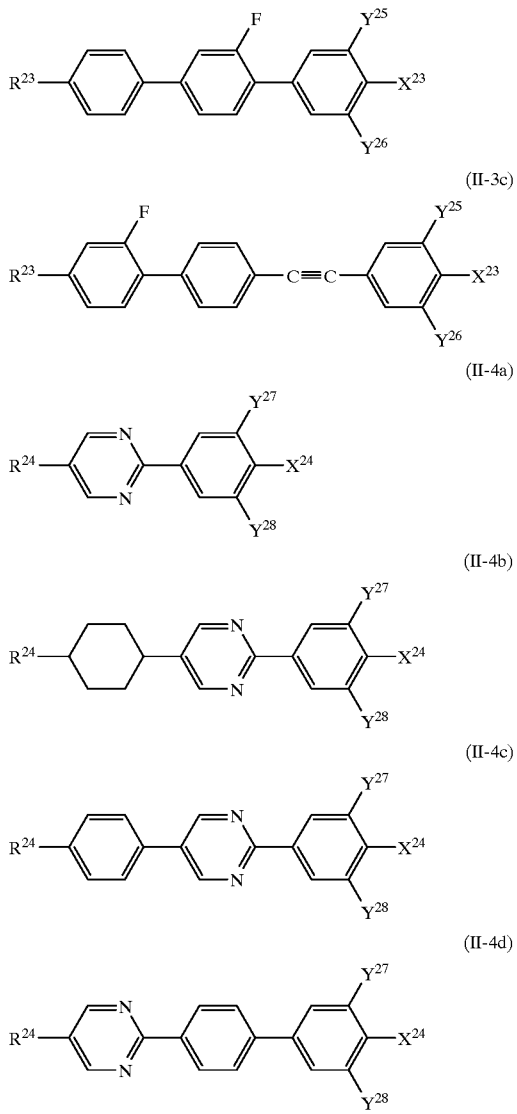

wherein $R^{21}$ to $R^{24}$, $X^{21}$ to $X^{24}$, $Y^{21}$ to $Y^{28, W21}$, and $W^{22}$ are as defined above.

The foregoing various compounds were used in the form of fully purified product obtained by removing impurities through distillation, column purification and recrystallization. The liquid crystal component B comprising these compounds can be well mixed with the liquid crystal component A as an essential component and is particularly useful for the adjustment of driving voltage depending on the purpose or the improvement of temperature dependence of driving voltage or response.

In particular, the compounds represented by the general formulae (II-1a) to (II-1h) and (II-2a) to (II-4d) can exert excellent such effects even if incorporated in an amount as small as from 1 to 25%.

Preferred embodiments will be further described.

In the foregoing compounds represented by the general formulae (II-1) to (II-4), $R^{21}$ is preferably a $C_{2-5}$ alkyl group or an alkenyl group represented by the general formula: $CH_2=CH-(CH_2)_p$ (in which p is 0 or 2). The compounds represented by the general formulae (II-1a) to (II-1c) preferably have these groups. In particular, it is preferred that the liquid crystal component B comprise at least one compound containing such an alkenyl group incorporated therein. In this manner, the viscosity or viscoelasticity of the composition can be reduced. Similarly, $R^{22}$ is preferably a $C_{2-5}$ alkyl group or an alkenyl group represented by the general formula: $CH_2=CH-(CH_2)_p$ (in which p is 2 or 4). The compounds represented by the general formulae (II-2a) to (II-2f) preferably have these groups.

Compounds represented by the general formulae (II-1) to (II-4) wherein $X^{21}$ to $X^{24}$ each represent F, Cl, —$OCF_3$ or —CN are preferably often used. If fast response is regarded as important, compounds represented by the general formulae (II-1a), (II-1d), (II-2a), (II-2c), (II-2d), (II-2g) and (II-3g) wherein $X^{21}$ to $X^{24}$ each are F or —$OCF_3$ are preferably often incorporated in the liquid crystal component B. If a higher birefringence index is needed, compounds represented by the general formulae (II-2a) to (II-4d) wherein $X^{22}$ to $X^{24}$ each are Cl, —$OCF_3$ or —CN are preferably often incorporated in the liquid crystal component B. If a lower driving voltage is needed, compounds represented by the general formulae (II-1a) to (II-1g) wherein $X^{21}$ is —CN and $Y^{21}$ is H or F, compounds represented by the general formulae (II-2a) to (II-2f) wherein $X^{22}$ is F, Cl or —CN and $Y^{23}$ is H or F, compounds represented by the general formulae (II-3a) to (II-3c) wherein $X^{23}$ is F, Cl or —CN and $Y^{25}$ is F and compounds represented by the general formulae (II-4a) to (II-4d) wherein $X^{24}$ is F, Cl or —CN and $Y^{27}$ is F are preferably often incorporated in the liquid crystal component B.

In particular, compounds represented by the general formulae (II-1) to (II-4) wherein $X^{21}$ to $X^{24}$ each are F are preferably often used in an active matrix display system, TFT-LCD, MIM-LCD, super TFT combined with IPS mode or light-scattering type liquid crystal display system having an active matrix technique (e.g., display system having a light-control layer containing a liquid crystal material and a transparent solid substance).

In order to improve the temperature properties of driving voltage, particularly at low temperatures, it is particularly preferred that the liquid crystal composition comprise the foregoing compound wherein at least one of $Y^{23}$, $Y^{24}$, $W^{21}$ and $W^{22}$ is F. Compounds represented by the general formulae (II-1) to (II-4) wherein $R^{23}$ is a $C_{2-5}$ alkyl group or an alkenyl group represented by the general formula: $CH_2=CH-(CH_2)_p$ (in which p is 2 to 5) are preferably used. The compounds represented by the general formulae (II-3a) to (II-3c) preferably contain these groups. $R^{24}$ may be a $C_{2-10}$ alkyl group, preferably a $C_{4-7}$ compound.

If a smaller birefringence index is needed, the compounds represented by the general formulae (II-1a) to (II-1g) are preferably often incorporated in the liquid crystal component B. If a greater birefringence index is needed, the compounds represented by the general formulae (II-3a) to (II-4c) are preferably often incorporated in the liquid crystal component B. If a lower driving voltage is needed, one or more of the compounds represented by the general formulae (II-1) to (II-3) wherein at least one of $Y^{21}$ to $Y^{25}$ and $W^{21}$ to $W^{23}$ is a fluorine atom are preferably incorporated in the liquid crystal component B.

If a fast response is regarded as important, the compounds represented by the general formulae (II-1) to (II-4) wherein $Y^{21}$ to $Y^{28}$ each are H and/or $W^{21}$ to $W^{24}$ each are H may be often used. If it is desired to improve the temperature dependence of driving voltage, compounds represented by the general formulae (II-1) to (II-4) wherein $Y^{21}$ to $Y^{28}$ and $W^{21}$ to $W^{24}$, particularly $Y^21$, $Y^{23}$, $Y^{25}$, $Y^{27}$, and $W^{21}$ to $W^{24}$ each are F, each are F are preferably often used. In particular, if $W^{21}$ and $W^{22}$ each are F, the selection of a compound represented by any one of the general formulae (II-1) to (II-4) wherein $Y^{24}$ is H can improve miscibility. If a compound represented by the general formula (II-3) is used, the selection of such a compound wherein $W^{23}$ and/or $W^{24}$ is F provides further improvement in miscibility.

In the general formula (II-1), at least one of $Z^{21}$ and $Z^{22}$ is preferably a single bond compound. In order to improve the response and miscibility at low temperatures, it is preferable to use a liquid crystal component B comprising a single bond compound and —COO—, —CH$_2$CH$_2$— or —(CH$_2$)$_4$— in combination.

If it is required that the birefringence index is larger, compounds represented by the general formulae (II-2) and (II-3) wherein $Z^{24}$ and $Z^{25}$ each are —C≡C— and/or compounds represented by the general formula (II-4) wherein $X^{24}$ is CN are preferably often incorporated in the liquid crystal component B.

The mixing proportion of the compound represented by the general formula (II-1), (II-2) or (II-4) wherein $m^1$ to $m^4$ each are 0, the compound represented by the general formula (II-1) or (II-2) wherein $m^1$ and $m^2$ each are 1, the compound represented by the general formula (II-4) wherein $m^3+m^4$ make 1 and/or the compound represented by the general formula (II-3) in the liquid crystal component B can be properly selected from the range of 0/100 to 100/0. If an even higher nematic phase-isotropic liquid phase transition temperature is needed, compounds represented by the general formulae (II-1) and (II-2) wherein $m^1$ and $m^2$ each are 1, compounds represented by the general formula (II-3) and/or compounds represented by the general formula (II-4) wherein $m^3+m^4$ make 1 are preferably often used.

If a smaller birefringence index is needed, compounds represented by the general formulae (II-1a) to (II-1g) are preferably often incorporated in the liquid crystal component B. If a greater birefringence index is needed, compounds represented by the general formulae (II-3a) to (II-4c) are preferably often incorporated in the liquid crystal component B. If a lower driving voltage is needed, one or more compounds represented by the general formulae (II-1) to (II-3) wherein at least one of $Y^{21}$ to $Y^{25}$ and $W^{21}$ to $W^{23}$ is F are preferably often incorporated in the liquid crystal component B.

Compounds represented by the general formulae (II-1) and (II-2) wherein hydrogen atoms (H) in the cyclohexane ring are replaced by deuterium atoms (D) may be used. These compounds are useful for the adjustment of the elastic constant of the liquid crystal composition or the adjustment of pretilt angle corresponding to alignment film. Thus, at least one compound having hydrogen atoms substituted by deuterium atoms (D) is preferably incorporated in the liquid crystal component B.

The effects of the liquid crystal component B which has been described can be obtained also when the content of the liquid crystal component C described later is very small. For the purpose of lowering the driving voltage particularly, the content of the liquid crystal component C can be lowered to not more than 10% by weight. In this case, it is preferable to lower the viscosity of the liquid crystal component C as much as possible. In this manner, the rise in the driving voltage is little or none or limited to only a small range, enabling an efficient improvement in response time. For example, if the content of the liquid crystal component C is small, the realization of this effect with the liquid crystal component B preferably involves the incorporation of any one of compounds represented by the general formulae (II-1) to (II-4) wherein $X^{21}$ to $X^{24}$ each are F, Cl or —OCF$_3$, compounds represented by the general formulae (II-1) to (II-4) wherein $Y^{21}$ to $Y^{24}$ each are F, represented by the general formulae (II-1) to (II-4) wherein $Z^{24}$ and $Z^{25}$ each are —COO— or —C≡C— and compounds represented by the general formulae (II-1) to (II-4) wherein $m^1$ is 1 in the liquid crystal component B. In particular, compounds represented by the general formulae (II-1) to (II-4) wherein $X^{21}$ to $X^{24}$ each are F, Cl, —OCF$_3$ or —CN and/or $Y^{21}$ to $Y^{23}$ each are F are desirable.

The liquid crystal composition of the present invention preferably a liquid crystal component C made of a compound having a dielectric anisotropy of from −2 to +2 in an amount of not more than 70% by weight in addition to the liquid crystal component A as an essential component. A preferred example of the liquid crystal compound having a dielectric anisotropy of from −2 to +2 referred to herein will be described hereinafter. In other words, such a liquid crystal compound has a rod-shaped chemical structure. Such a liquid crystal compound has a core structure having from 1 to 4 6-membered rings at the central portion. The 6-membered rings positioned at both longitudinal ends of the central portion have terminal groups substituted at positions corresponding to the longitudinal position of liquid crystal molecule. The terminal groups positioned at both ends are nonpolar groups such as alkyl group, alkoxy group, alkoxyalkyl group, alkenyl group, alkenyloxy group and alkanoyloxy group. The liquid crystal composition of the present invention preferably comprises from 1 to 20, more preferably from 2 to 12 such liquid crystal components C.

The liquid crystal component C of the present invention preferably contains one or more compounds selected from the group consisting of compounds represented by the general formulae (III-1) to (III-4):

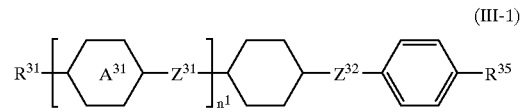

(III-1)

(III-2)

(III-3)

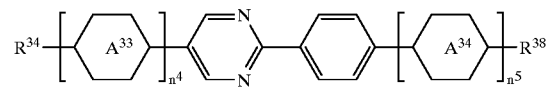

(III-4)

wherein $R^{31}$ to $R^{34}$ each independently represent a C$_{2-7}$ straight-chain alkyl group or alkenyl group; $R^{35}$ to $R^{38}$ each independently represent a C$_{1-7}$ straight-chain alkyl group, alkoxy group, alkenyl group, alkenyloxy group or C$_u$H$_{2u+1}$—O—C$_v$H$_{2v}$ in which u and v each independently represent an integer of from 1 to 5; $Y^{31}$ represents a hydrogen atom, fluorine atom or —CH$_3$; $Y^{32}$ and $Y^{33}$ each independently represent a hydrogen atom or fluorine atom; $Z^{31}$ to $Z^{34}$ each independently represent a single bond, —COO—, —CH$_2$CH$_2$— or —(CH$_2$)$_4$—; $Z^{21}$ may also represent —C≡C— or —CH=CH—; $Z^{35}$ represents a single bond, —C≡C—, —COO—, or —CF=CF—; rings $A^{31}$ and $A^{32}$ each independently represent a cyclohexane ring or cyclohexene ring; rings $A^{33}$ and $A^{34}$ each independently represent a cyclohexane ring or benzene ring; and $n^1$ to $n^5$ each independently represent an integer of 0 or 1, with the proviso that $n^4+n^5$ make an integer of 0 or 1, and hydrogen atoms (H) in the cyclohexane ring in the various compounds may be replaced by deuterium atoms (D), in an amount of from 10 to 100% by weight. Particularly preferred examples of the compounds represented by the general formulae (III-1) to (III-4) in the liquid crystal component C of the present invention include those represented by the following general formulae (III-1a) to (III-4e):

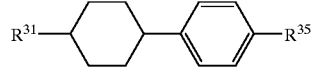
(III-1a)

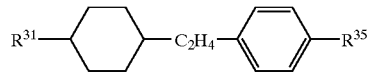
(III-1b)

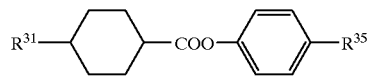
(III-1c)

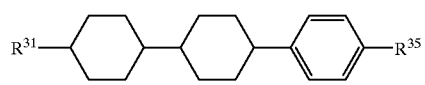
(III-1d)

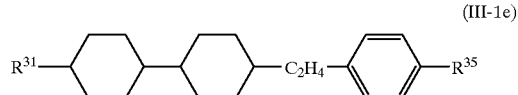
(III-1e)

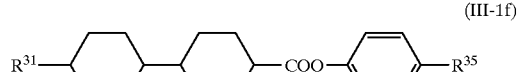
(III-1f)

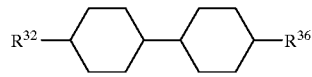
(III-2a)

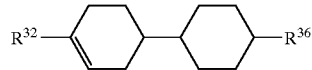
(III-2b)

(III-2c)

(III-2d)

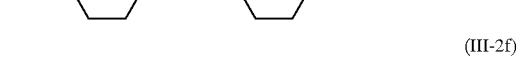
(III-2e)

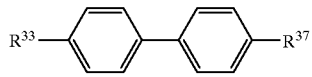
(III-2f)

-continued

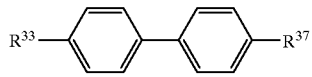
(III-3a)

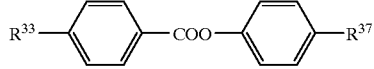
(III-3b)

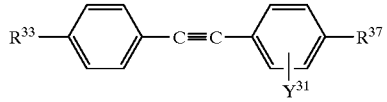
(III-3c)

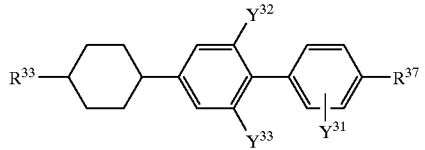
(III-3d)

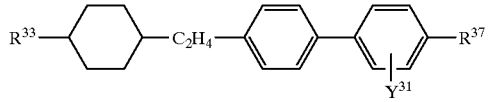
(III-3e)

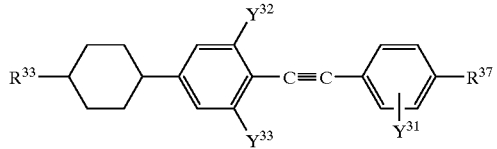
(III-3f)

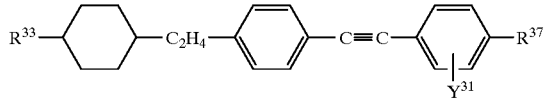
(III-3g)

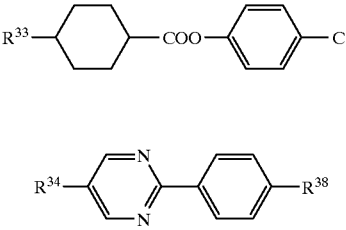
(III-3h)

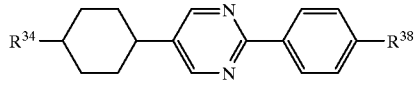
(III-4a)

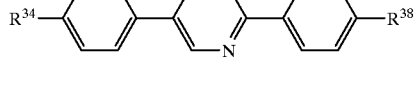
(III-4b)

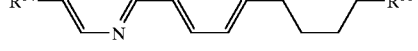
(III-4c)

(III-4d)

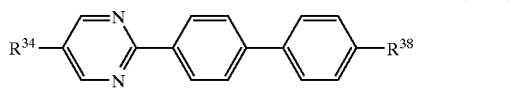
(III-4e)

wherein $R^{31}$ to $R^{38}$ and $Y^{31}$ to $Y^{33}$ are as defined above.

The liquid crystal component C containing such a compound can be well mixed with the liquid crystal component A containing a compound of the general formula (I) and thus is useful for the improvement of nematic phase at low temperatures.

The liquid crystal composition can comprise as liquid crystal component C compounds represented by the general formulae (III-1) to (III-4) incorporated therein to lower its viscosity or viscoelasticity and hence exhibit a relatively high specific resistivity and/or voltage holding ratio. The viscosity of the liquid crystal component C is preferably as low as possible, e.g., not more than 45 cp, more preferably not more than 30 cp, even more preferably not more than 20 cp, particularly not more than 15 cp in the present invention. Preferred among these compounds represented by the general formulae (III-1) to (III-4) as liquid crystal component C are those represented by the general formulae (III-1a) to (III-3a), (III-3c) to (III-3g), (III-4a), and (III-4d) to (III-4e). Further, a liquid crystal component C containing at least one such compound wherein $R^{31}$ to $R^{34}$ each are a $C_{2-5}$ straight-chain alkyl group or an alkenyl group represented by the general formula: $CH_2=CH-(CH_2)_q$ (in which q is 0 or 2) provides a better effect. In particular, compounds represented by the general formulae (III-1a), (III-1d), and (III-2a) to (III-2c), compounds represented by the general formulae (III-3c) to (III-3f) wherein $Y^{31}$ is a hydrogen atom and/or compounds represented by the general formula (III-4a) wherein $R^{38}$ is an alkyl group can exert this effect even when incorporated in an amount as small as from 3 to 30% and thus are useful for the improvement of response time for STN-LCD for example.

A preferred example of the compound, if it is represented by the general formula (III-1), which should be incorporated in the liquid crystal component C to exert the foregoing effects is one wherein $R^{31}$ represents a $C_{2-5}$ straight-chain alkyl group or alkenyl group, $R^{35}$ represents a $C_{1-4}$ straight-chain alkyl group, alkoxy group, alkenyl group or alkenyloxy group; ring $A^{31}$ represents a cyclohexane ring; $Z^{32}$ represents a single bond or —COO— if $n^1$ is 0; and $Z^{31}$ and $Z^{32}$ each represent a single bond if $n^1$ is 1. A preferred example of the compound, if it is represented by the general formula (III-2), which should be incorporated in the liquid crystal component C to exert the foregoing effects is one wherein $R^{32}$ represents a $C_{2-5}$ straight-chain alkyl group or alkenyl group; $R^{36}$ represents a $C_{1-4}$ straight-chain alkyl group, alkoxy group, alkenyl group or alkenyloxy group; ring $A^{32}$ represents a cyclohexane ring or cyclohexene ring and $Z^{33}$ represents a single bond, —COO— or —CH$_2$CH$_2$— if $n^2$ is 0; and ring $A^{32}$ represents a cyclohexane ring and $Z^{33}$ represents a single bond or —CH$_2$CH$_2$— if $n^2$ is 1.

The liquid crystal component C of the present invention may be formed by compounds represented by the general formulae (III-1), (III-2), (III-3) and (III-4), singly for each. By using a compound represented by the general formula (III-1) and/or a compound represented by the general formula (III-2) and a compound represented by the general formula (III-3) and/or a compound represented by the general formula (III-4), particularly one wherein $Z^{35}$ represents —C≡C—, in combination, the birefringence index of the liquid crystal composition can be easily optimized depending on the purpose. By using compounds represented by the general formulae (III-1) and (III-2), e.g., (III-1a) to (III-2f), as much as possible, the birefringence index of the liquid crystal composition can be lowered, making it easy to realize the reduction of color unevenness, the enhancement of viewing angle and the increase of contrast ratio in liquid crystal display systems. By using compounds represented by the general formula (III-3), e.g., (III-3a) to (III-3h), or compounds represented by the general formula (III-4), e.g., (III-4a) to (III-4e), as much as possible, the birefringence index of the liquid crystal composition can be increased, making it possible to prepare a liquid crystal display device having a liquid crystal layer which is as thin as from 1 to 5 μm.

The liquid crystal composition of the present invention, if it is intended to respond to the magnitude of driving voltage at fast response, may be arranged as follows. If it is intended to operate at a middle driving voltage, the liquid crystal composition of the present invention preferably exhibits a dielectric anisotropy of from 3 to 15 and a viscosity of from 8 to 20 cp at 20° C. In this case, the viscosity of the liquid crystal component C itself is preferably not more than 25 cp, more preferably not more than 15 cp, particularly not more than 10 cp. If it is intended to operate at a low driving voltage, the liquid crystal composition of the present invention preferably exhibits a dielectric anisotropy of from 15 to 30, particularly from 18 to 28.

The nematic liquid crystal composition of the present invention, if the liquid crystal component A incorporated therein is mainly composed of a so-called p-type compound having a great dielectric anisotropy, may be free of or may optionally contain a liquid crystal component B, i.e., compound having a dielectric anisotropy of not less than +2. Further, the nematic liquid crystal composition of the present invention, if the liquid crystal component A incorporated therein is mainly composed of a so-called n-type compound having a small dielectric anisotropy, preferably comprises a liquid crystal component B, i.e., compound having a dielectric anisotropy of not less than +2. Further, the nematic liquid crystal composition may comprise a liquid crystal component C as necessary.

At present, alignment films used for TN-LCD, STN-LCD or TFT-LCD are often made of polyimide-based compounds. For example, LX1400, SE150, SE610, AL1051, AL3408, etc. are used. The specification of alignment film is related to liquid crystal display properties, display quality, reliability and productivity. For example, pretilt angle is important for liquid crystal material. The magnitude of pretilt angle needs to be properly adjusted to obtain desired liquid crystal display properties or uniform alignment. For example, if the pretilt angle is large, unstable alignment can easily occur. On the contrary, if the pretilt angle is small, sufficient display properties cannot be satisfied.

The inventors found that a liquid crystal material having a large pretilt angle and a liquid crystal material having a small pretilt angle can be sorted from each other. It was also found that the application of this technique makes it possible to realize desired liquid crystal display properties or uniform alignment from liquid crystal materials. This technique can be applied to the present invention. For example, if the liquid crystal component B contains compounds represented by the general formulae (II-1) to (II-4), the foregoing technique can be applied as follows. In some detail, a large pretilt angle can be obtained by increasing the content of the compounds represented by the general formulae (II-1) to (II-4) wherein $R^{21}$ is an alkenyl group, $X^{21}$ is F, Cl or —CN, and $Y^{21}$ and $Y^{22}$ each are F and/or compounds represented by the general formulae (II-1) to (II-4) wherein $R^{21}$ is an alkyl group, $X^{21}$ is F, Cl or —CN, and $Z^{22}$ is —$CH_2CH_2$— or —$(CH_2)_4$—. A small pretilt angle can be obtained by increasing the content of the compounds represented by the general formulae (II-1) to (II-4) wherein $R^{21}$ is an alkenyl group or $C_sH_{2s+1}$—O—$C_tH_{2t}$, $X^{21}$ is F, $Y^{21}$ is F, and $Y^{22}$ is H and/or compounds represented by the general formulae (II-1) to (II-4) wherein $Z^{22}$ is —COO—. In the case of the compounds represented by the general formulae (II-1), (III-1) and (III-2) wherein hydrogen atoms (H) in the cyclohexane ring are replaced by deuterium atoms (D), different pretilt angles can be obtained with different substitution positions. Thus, these compounds make it possible to adjust pretilt angle in a broad range. This effect, if a large pretilt angle is required for example, can be almost obtained by incorporating the foregoing compounds in the liquid crystal composition in an amount of from 10 to 40% by weight or more based on the total weight of the liquid crystal composition.

The technique concerning the compound of the general formula (I) according to the present invention is referred to in, e.g., JP-A-54-87688. For example, a mixture containing compounds represented by the general formulae (a-1) and (a-2) is disclosed. This technique is allegedly useful for the improvement of miscibility or response characteristics. However, the composition disclosed in the above cited patent finds difficulty in response time and requires improvement. For example, TN-LCD is now required to have a response time of 60 msec. or less, preferably 50 msec. or less, more preferably 40 msec. or less, particularly 30 msec. or less and thus requires improvement. In particular, the compounds represented by the general formulae (a-1) and (a-2) tend to deteriorate response. Thus, new improvements are needed.

The present invention gives solution to the foregoing problems. In some detail, the following countermeasures have been found. (1) The liquid crystal component A is not used in excess. The content of the liquid crystal component A is restricted to not more than 50% by weight. (2) If the content of the liquid crystal component A is particularly great, 4 or more compounds constituting the liquid crystal component B are used. (3) The liquid crystal component B contains one or more cyclohexane ring-containing compounds. (4) If the liquid crystal component B contains compounds represented by the general formulae (II-2) and (II-3), compounds represented by the general formula (II-1) are used as well. (5) If the content of the liquid crystal component A is particularly great, a liquid crystal component C is used as well. (6) If the liquid crystal component B contains compounds represented by the general formula (II-2) and/or compounds represented by the general formula (II-3), a liquid crystal component C is used as well even in a slight amount. In the case of the countermeasure (3), even more desirable results are obtained by incorporating a compound of the general formula (II-1) in the liquid crystal component B. In the case of the countermeasure (6), even more desirable results are obtained by incorporating compounds represented by the general formulae (III-1) to (III-3) in the liquid crystal component C.

The content of the various liquid crystal components in the nematic liquid crystal composition of the present invention may be predetermined as follows. The content of the liquid crystal component A is predetermined to a range of from 1 to 50% by weight, preferably from 3 to 40% by weight. The content of the liquid crystal component B is predetermined to a range of from 10 to 90% by weight, preferably from 25 to 90% by weight, more preferably from 25 to 80% by weight. The content of the liquid crystal component C is predetermined to not more than 70% by weight, preferably from 3 to 65% by weight, more preferably from 5 to 60% by weight, even more preferably from 10 to 55% by weight. The content of the compound represented by the general formula (I), if it is used singly, is preferably less than 20% by weight. If the content of the compound represented by the general formula (I) exceeds this range, two or more such compounds are preferably used. The content of the compounds represented by the general formulae (I-1) to (I-13) in the liquid crystal component A is predetermined to a range of from 50 to 100% by weight, preferably from 70 to 100% by weight. The content of the compounds represented by the general formulae (II-1) to (II-4) or the compounds represented by the general formulae (II-1a) to (II-4d), if they are used singly, is preferably not more than 30% by weight, more preferably not more than 25% by weight. If the content of these compounds exceeds this range, two or more such compounds are preferably used. The content of the compounds represented by the general formulae (II-1a) to (II-4d) in the liquid crystal component B is predetermined to a range of from 10 to 100% by weight, preferably from 50 to 100% by weight, more preferably from 75 to 100% by weight. The content of the compounds represented by the general formulae (III-1) to (III-4) or the compounds represented by the general formulae (III-1a) to (III-4e), if they are used singly, is preferably not more than 30% by weight, more preferably not more than 25% by weight. If the content of these compounds exceeds this range, two or more such compounds are preferably used. The content of the compounds represented by the general formulae (III-1a) to (III-4e) in the liquid crystal component C is predetermined to a range of from 10 to 100% by weight, preferably from 50 to 100% by weight, more preferably from 75 to 100% by weight.

The crystal phase- or smectic phase-nematic phase transition temperature is preferably not higher than −10° C., more preferably not higher than −20° C., particularly not higher than −30° C. The nematic phase-isotropic liquid phase transition temperature is not lower than 60° C., preferably not lower than 70° C., more preferably from 80° C. to 130° C. The liquid crystal composition of the present invention needs to have a dielectric anisotropy of not less than 3, preferably from 4 to 40, more preferably from 4 to 16 if fast response is regarded as important or from 17 to 30 if a lower driving voltage is needed. The smaller or middle birefringence index is preferably predetermined to a range of from not less than 0.08 to less than 0.18. The higher birefringence index is preferably predetermined to a range of from not less than 0.18 to less than 0.33. The properties of such a nematic liquid crystal composition are useful in active matrix, twisted nematic or super twisted nematic liquid crystal display systems.

The foregoing nematic liquid crystal composition is useful for fast response TN-LCD or STN-LCD. The foregoing nematic liquid crystal composition is also useful for liquid crystal display devices which can utilize birefringence of a liquid crystal layer and a phase difference plate to make color display without using any color filter layer. The nematic liquid crystal composition of the present invention can be incorporated in a transparent or reflective liquid crystal display device. These liquid crystal display devices have a transparent electrode layer and two substrates at least one of which is transparent. Between the two substrates the molecules of the nematic liquid crystal composition are twist-aligned. Depending on the purpose, the angle of twist can be predetermined to a range of from 30° to 360°, preferably from 90° to 270°, particularly from 45° to 135° or from 180° to 260°. Therefore, the liquid crystal composition of the present invention may comprise a compound containing an optically active group which gives an induced helical pitch of from 0.5 to 1,000 μm. The pretilt angle given by the alignment film provided on the transparent electrode substrate is preferably predetermined to a range of from 1° to 20°, more preferably from 10 to 40 if the angle of twist is from 30° to 100°, from 2° to 6° if the angle of twist is from 100° to 180°, from 3° to 12° if the angle of twist is from 180° to 260° or from 6° to 20° if the angle of twist is from 260° to 360°.

In order to improve its properties, the liquid crystal composition of the present invention may comprise other nematic liquid crystal compounds, smectic liquid crystal compounds and/or cholesteric liquid crystal compounds which can be recognized as a liquid crystal compound besides the compounds represented by the foregoing general formulae (I-1) to (III-4). However, the use of a large amount of these compounds causes deterioration of the properties of the nematic liquid crystal composition. Accordingly, the amount of these compounds to be added is restricted depending on the requirements for the nematic liquid crystal composition.

A preferred example of the liquid crystal composition of the present invention will be described hereinafter.

For example, a nematic liquid crystal composition comprising a liquid crystal component A consisting of compounds represented by the following general formula (If):

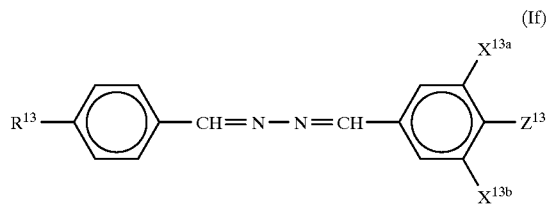

wherein $R^{13}$ represents a $C_{1-10}$ straight-chain alkyl group or alkoxyl group; $Z^{13}$ represents a fluorine atom, chlorine atom, cyano group or —$CF_3$; and $X^{13a}$ and $X^{13b}$ each independently represent a fluorine atom or hydrogen atom and at least one of a liquid crystal component B consisting of compounds having a dielectric anisotropy of not less than +2 and a liquid crystal component C consisting of compounds having a dielectric anisotropy of from −2 to +2 is desirable. In the foregoing nematic liquid crystal composition, the foregoing liquid crystal component A is preferably used in combination with a compound represented by the following general formula (Ig):

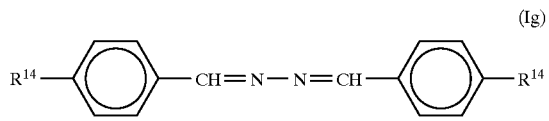

wherein $R^{14}$'s each independently represent a $C_{1-10}$ straight-chain alkyl group or alkoxyl group. More preferably, the liquid crystal component A comprises a compound represented by the general formula (If) wherein $R^{13}$ represents an ethyl group or propyl group and/or a compound represented by the general formula (If) wherein $Z^{13}$ represents a fluorine atom and/or a compound represented by the general formula (If) wherein $X^{13a}$ and $X^{13b}$ each are a fluorine atom in an amount of from 30 to 100% by weight. Even more preferably, the liquid crystal composition comprises the liquid crystal component A in an amount of from 1 to 95% by weight.

Further, the nematic liquid crystal composition of the present invention preferably comprises as the liquid crystal component A a compound represented by the following general formula (Ih):

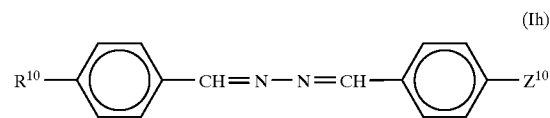

wherein $R^{10}$ represents a $C_{1-10}$ straight-chain alkyl group, alkoxyl group or $C_{2-10}$ straight-chain alkenyl group; and $Z^{10}$ represents a $C_{2-10}$ straight-chain alkyl group.

More preferably, the nematic liquid crystal composition comprises a liquid crystal material B consisting of compounds having a dielectric anisotropy of not less than +2. Even more preferably, the liquid crystal composition exhibits a dielectric anisotropy of not less than 3, a nematic phase-isotropic liquid phase transition temperature of not lower than 60° C. and a crystalline phase or smectic phase-nematic phase transition temperature of not higher than 0° C. Further, in the nematic liquid crystal composition of the present invention, the liquid crystal component A preferably comprises a compound represented by the general formula (Ih) wherein $R^{10}$ represents a methyl group, ethyl group, propyl group or butenyl group and/or a compound represented by the general formula (Ih) wherein $Z^{10}$ represents a butenyl group in an amount of from 30 to 100% by weight. More preferably, the liquid crystal composition comprises the foregoing liquid crystal component A in an amount of from 1 to 50% by weight.

Similarly, the nematic liquid crystal composition preferably comprises as the liquid crystal component A a compound selected from the group consisting of compounds represented by the following general formulae (Ii) and (Ij):

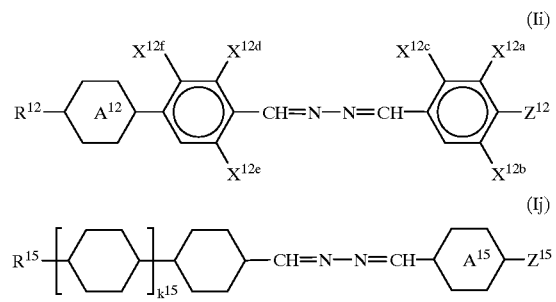

wherein $R^{12}$ and $R^{15}$ each independently represent a $C_{1-10}$ straight-chain alkyl group, alkoxyl group or $C_{2-10}$ straight-chain alkenyl group; $Y^{12a}$ to $Y^{12f}$ each independently represent a hydrogen atom or fluorine atom; $Z^{12}$ and $Z^{15}$ each independently represent a $C_{1-10}$ straight-chain alkyl group, alkoxyl group, $C_{2-10}$ straight-chain alkenyl group, fluorine atom, chlorine atom, —$CF_3$, —$OCF_3$ or cyano group; k represents an integer of from 0 or 1; rings $A^{12}$ and $A^{15}$ each independently represent 1,4-phenylene group which may be substituted by fluorine atom or trans-1,4-cyclohexylene group; and $k^{15}$ represents an integer of from 0 or 1.

More preferably, the nematic liquid crystal composition comprises a liquid crystal material B made of a compound having a dielectric anisotropy of not less than.+2. Even more preferably, the nematic liquid crystal composition exhibits a dielectric anisotropy of not less than 3, a nematic phase-isotropic liquid phase transition temperature of not lower than 60° C. and a crystalline phase or smectic phase-nematic phase transition temperature of not higher than 0° C. Further, in the nematic liquid crystal composition of the present invention, the liquid crystal component A preferably is used in combination with a compound represented by the following general formula (Ik):

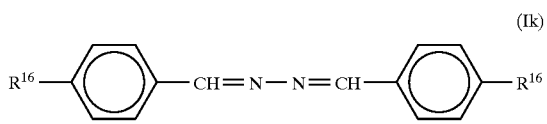

wherein $R^{16}$'s each independently represent a $C_{1-10}$ straight-chain alkyl group, alkoxyl group or $C_{2-10}$ straight-chain alkenyl group. Further, the liquid crystal composition of the present invention preferably comprises the foregoing liquid crystal component A in an amount of from 1 to 50% by weight:

Similarly, the nematic liquid crystal composition of the present invention preferably comprises a liquid crystal component A consisting of compounds represented by the following general formula (Im):

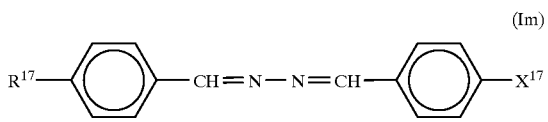

wherein $R^{17}$ represents a $C_{1-10}$ straight-chain alkyl group or alkoxyl group; and $X^{17}$ represents a $C_{1-10}$ straight-chain alkyl group, alkoxyl group, fluorine atom, chlorine atom or cyano group and a liquid crystal component B consisting of compounds having a dielectric anisotropy of not less than +2.

The liquid crystal composition of the present invention preferably comprises 5 to 40 compounds. The foregoing liquid crystal component A preferably comprises a compound represented by the general formula (Im) wherein $X^{17}$ represents a fluorine atom in an amount of from 30 to 100% by weight. More preferably,-the liquid crystal component A comprises a compound represented by the general formula (Im) wherein $R^{17}$ represents a methyl group, ethyl group, propyl group, butyl group or pentyl group and/or a compound represented by the general formula (Im) wherein $Z^{17}$ represents a methyl group, ethyl group, propyl group, butyl group or pentyl group in an amount of from 30 to 100% by weight. Further, the nematic liquid crystal composition of the present invention comprises the foregoing liquid crystal component A in an amount of from 1 to 50% by weight.

Similarly, the nematic liquid crystal composition of the present invention preferably comprises a liquid crystal component A consisting of compounds represented by the following general formula (In):

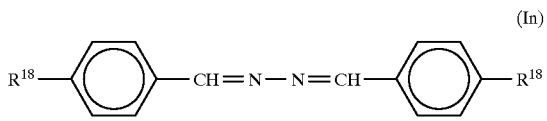

wherein $R^{18}$'s each independently represent a $C_{1-10}$ straight-chain alkyl group or alkoxyl group and a liquid crystal component B consisting of compounds having a dielectric anisotropy of not less than +2. Even more preferably, the nematic liquid crystal composition exhibits a dielectric anisotropy of not less than 3, a nematic phase-isotropic liquid phase transition temperature of not lower than 60° C. and a crystalline phase or smectic phase-nematic phase transition temperature of not higher than 0° C.

The foregoing liquid crystal component A preferably comprises a compound represented by the general formula (In) wherein $R^{18}$ represents a methyl group, ethyl group or propyl group in an amount of from 30 to 100% by weight. More preferably, the liquid crystal composition of the present invention comprises the foregoing liquid crystal component A in an amount of from 1 to 50% by weight.

Further, the liquid crystal composition of the present invention may comprise other compounds besides the foregoing liquid components B and C as necessary. Preferably, the foregoing liquid crystal composition comprises one or more compounds having a core structure containing four 6-membered rings, the liquid crystal phase-isotropic liquid phase transition temperature of not lower than 100° C.

The foregoing liquid crystal composition preferably comprises a compound having an optically active group which gives an inductive helical pitch of from 0.5 to 1,000 μm.

Further, the present invention also provides an active matrix, twisted nematic or super twisted nematic liquid crystal display device comprising the foregoing nematic liquid crystal composition. The thickness of the liquid crystal layer is preferably from 1 to 30 μm.

The present invention further provides a light-scattering type liquid crystal display system comprising the foregoing nematic liquid crystal composition and a light-control layer containing a transparent solid substance. In the light-control layer, the foregoing liquid crystal composition preferably forms a continuous layer in which the foregoing transparent solid substance forms a uniform three-dimensional network structure. The foregoing transparent solid substance is preferably formed by a polymerizable composition containing a polymer-forming bifunctional monomer and a monofunctional monomer.

The inventors found that because of its high birefringence index the foregoing liquid crystal composition can also be effectively incorporated in a light-scattering type liquid crystal display device comprising a light-control layer containing a liquid crystal material and a transparent solid substance sandwiched by a pair of substrates having a transparent electrode layer at least one of which sheets is transparent so that the liquid crystal display device is provided with a high contrast given by favorable light-scattering properties.

In general, a liquid crystal material having a large birefringence index is disadvantageous in that an induced crystal phase or a partly crystallized smectic phase often appears while narrowing its liquid crystal phase. Further, such a liquid crystal material exhibits a great birefringence index and a broad liquid crystal temperature range but cannot realize a particularly high voltage holding ratio essential for active matrix system. Further, a light-scattering type liquid crystal display device prepared from such a liquid crystal material shows a memory phenomenon in which the light transmittance $T_0$ (determined when no voltage is applied) measured shortly after the switching from application of voltage to application of no voltage is greater than that measured shortly after prepared or after a prolonged period of time of voltage application, eventually deteriorating the contrast in the liquid crystal display. The sample use of a fluorotolan-based compound doesn't always give favorable results. The liquid crystal composition of the present invention can avoid or lessen these problems.

Further, the present invention is based on the discovery that the liquid crystal composition of the present invention is a liquid crystal material which exhibits a higher miscibility due to the occurrence of a polymer-forming compound which forms a transparent solid substance. Such a transparent solid substance is preferably formed by the polymerization of a polymer-forming compound. For example, the preparation of such a transparent solid substrate may involve a process which inserts a light-control layer-forming material comprising an ultraviolet-curing resin composition containing a compound having an ultraviolet-curing vinyl group and a liquid crystal material between a pair of substrates, and then curing the ultraviolet-curing resin composition. If the miscibility of the polymer-forming compound and the liquid crystal material is higher, a more uniform solution can be obtained in a broader temperature range. When the polymer-forming compound is cured under these conditions, a light-control layer having light-scattering properties can be prepared free of or almost without offset, providing display properties free of unevenness of driving voltage or contrast ratio as well as a light-scattering type liquid crystal display device which realizes display with a more uniform opaqueness. Accordingly, a liquid crystal material was found which can be subjected to vacuum injection or the like to prepare a liquid crystal display device having more uniform light-scattering properties or a relatively large-sized liquid crystal display device.

The liquid crystal material preferably comprises a cyano group-free liquid crystal compound to exhibit a high voltage holding ratio or a birefringence index as high as not less than 0.200 necessary for active matrix system. As the liquid crystal compound to be used herein there may be preferably used an azine derivative represented by the general formula (I), more preferably in combination with fluolotolan-based compounds represented by the general formulae (II-2) and (II-3). In particular, a fluorotolan-based compound having three rings is preferably used as an essential component. The incorporation of an azine derivative represented by the general formula (I) makes it possible to provide a light-scattering type liquid crystal display system having an improved fast response useful for animated display. In order to prepare a liquid crystal device having a higher voltage holding ratio, it is preferred to use a liquid crystal material having a higher specific resistivity, preferably not less than $10^{11}$ Ω·cm, more preferably not less than $10^{12}$ Ω·cm, most preferably not less than $10^{13}$ Ω·cm.

The inventors disclose in JP-A-6-222320 that the relationship between the physical properties of the liquid crystal material and the display characteristics of the liquid crystal display device is represented by the following equation (VI):

$$Vth \propto \frac{d}{\langle r \rangle + {}^1Kii/A} \left( \frac{{}^2Kii}{\Delta \varepsilon} \right)^{1/2} \quad (VI)$$

wherein Vth represents a threshold voltage; ${}^1Kii$ and ${}^2Kii$ each represent an elastic constant; ii represents 11, 22 or 33; $\Delta \varepsilon$ represents a dielectric anisotropy; <r>represents the average space on mesh size; A represents the anchoring energy of the transparent solid substance with respect to the liquid crystal molecule; and d represents the distance between the substrates having a transparent electrode.

This equation means that the force given to the liquid crystal molecule by the interface of transparent solid substance changes with the ratio of elastic constant ${}^1Kii$ to anchoring energy A. In particular, this equation means that this effect substantially widens the actual average space <r>by ${}^1Kii/A$, effectively reducing the driving voltage. This relationship can also be applied to the present invention. By selecting the dielectric anisotropy and elastic constant of the liquid crystal material depending on the liquid crystal compound constituting the liquid crystal material, a better liquid crystal display device which can be driven at a low voltage can be obtained. To be more concrete, the following arrangement is preferred. The transparent solid substance can be formed by a polymerizable composition containing a bifunctional monomer and a monofunctional monomer as a polymer-forming compound to obtain better liquid crystal display properties. It is thought that the use of a composition comprising a bifunctional monomer and a monofunctional monomer in combination as a polymer-forming compound provides a transparent solid substance with a more uniform structure that makes it easier to control the properties of the interface with the liquid crystal material in the process for the formation of a transparent solid substance from a polymer-forming compound. To be more concrete, the average space <r>and anchoring energy A in the foregoing equation (IV) can be predominant over the other factors. In this manner, the driving voltage can be reduced while maintaining the opaqueness and transparency. Further, the liquid crystal material containing the foregoing compound represented by the general formula (I) for example may comprise a polymerizable composition having a bifunctional monomer and a monofunctional monomer in combination as a polymer-forming compound to eliminate or lessen the memory phenomenon.

The liquid crystal material to be used in the present invention is expected to be useful for a display device comprising liquid crystal droplets formed by microencapsulating a liquid crystal material, dispersed in a transparent solid substance between a pair of substrates having a transparent electrode. The transparent solid substance to be formed between the substrates may be dispersed in fibrous or particulate form or may be in the form of film having droplets of a liquid crystal material dispersed therein. Preferably, the transparent solid substance has a three-dimensional network structure. The liquid crystal material preferably forms a continuous layer. By forming a disordered liquid crystal material, an optical interface is formed to cause light scattering. If the average diameter of the three-dimensional network structure formed by such a transparent solid substance is too great or small as compared with the wavelength of light, it tends to deteriorate light scattering properties. Thus, it is preferably from 0.2 to 2 μm. The thickness of the light-control layer is preferably from 2 to 30 μm, particularly from 5 to 20 μm, depending on the purpose.

On the basis of the inventors' discovery of preferred constitution of miscibility with liquid crystal compound and polymer-forming compound constituting the liquid crystal material and polymerizable composition from extensive studies of liquid crystal material and transparent solid substance constituting a liquid crystal display device utilizing light-scattering state (off-state) and highly transparent state (on-state), the liquid crystal display device of the present invention thus prepared exhibits a lessened memory phenomenon and display properties with a more uniform opaqueness while maintaining fast response, low driving voltage, high light-control layer resistivity and high contrast ratio and enhancing these properties. Thus, the liquid crystal display device of the present invention exhibits properties required for active matrix system. Further, the liquid crystal display device of the present invention can be used for projection display devices or direct view type portable terminal display devices (personal digital assistance).

Preferred embodiments for the azine derivative, process for the preparation thereof, namatic liquid crystal composition containing the same and liquid crystal display system using the same of the present invention are as follows:

(1) A compound, represented by the following general formula (I):

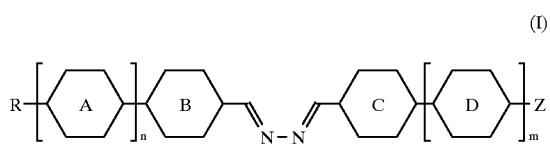

wherein
m and n each independently represent an integer of 0 or 1;
rings A, B, C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group;
R represents a $C_{1-12}$ alkyl group or alkoxyl group, $C_{2-12}$ alkenyl group or alkoxylalkyl group or $C_{3-12}$ alkenyloxy group; and
Z represents a fluorine atom, chlorine atom, bromine atom, cyano group, —$OCF_3$, —$OCF_2H$, —$CF_3$, —$OCH_2CF_3$, $C_{1-12}$ alkyl group or alkoxyl group, $C_{2-12}$ alkenyl group or alkoxylalkyl group or $C_{3-12}$ alkenyloxy group,
with the proviso that Z is not an alkyl group, cyano group, fluorine atom, chlorine atom or bromine atom when m and n each are 0 and rings B and C each are 1,4-phenylene group and R is an alkyl group.

(2) The compound described in Clause (1), wherein m and n are 0 at the same time and rings B and C each independently represent 1,4-phenylene group which may be substituted by fluorine atom, with the proviso that at least one of rings B and C is substituted by fluorine atom when R represents a $C_{1-12}$ alkyl group and Z represents a fluorine atom, chlorine atom, bromine atom or $C_{1-12}$ alkyl group.

(3) The compound described in Clause (2), wherein R represents a $C_{2-12}$ alkenyl group, Z represents a $C_{1-7}$ straight-chain alkyl group, $C_{2-12}$ alkenyl group or fluorine atom and rings B and C each represent 1,4-phenylene group which may be substituted by fluorine atom.

(4) The compound described in Clause (2), wherein R represents a $C_{1-7}$ straight-chain alkyl group, Z represents a fluorine atom or —$OCF_3$ and rings B and C each represents 1,4-phenylene group which may be substituted by fluorine atom.

(5) The compound described in Clause (1), wherein n represents 1, m represents 0, R represents a $C_{1-7}$ straight-chain alkyl group or $C_{2-7}$ straight-chain alkenyl group, rings B and C each represent 1,4-phenylene group which may be substituted by fluorine atom and Z represents a fluorine atom, trifluoromethoxy group, $C_{1-7}$ straight-chain alkyl group or $C_{4-7}$ straight-chain alkenyl group.

(6) The compound described in Clause (1), wherein m and n are 0 at the same time, ring B represents trans-1,4-cyclohexylene group and ring C represents 1,4-phenylene group which may be substituted by fluorine atom or trans-1,4-cyclohexylene group.

(7) A process for the preparation of a compound represented by the general formula (I):

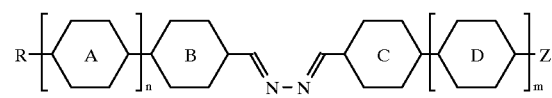

wherein m and n each independently represent an integer of 0 or 1; rings A, B, C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; R represents a $C_{1-12}$ alkyl group or alkoxyl group, $C_{2-12}$ alkenyl group or alkoxylalkyl group or $C_{3-12}$ alkenyloxy group; and Z represents a fluorine atom, chlorine atom, bromine atom, cyano group, —$OCF_3$, —$OCF_2H$, —$CF_3$, —$OCH_2CF_3$, $C_{1-12}$ alkyl group or alkoxyl group, $C_{2-12}$ alkenyl group or alkoxylalkyl group or $C_{3-12}$ alkenyloxy group, which comprises allowing a compound represented by the following general formula (II):

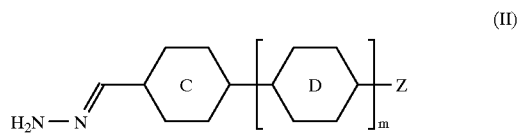

wherein Z represents a fluorine atom, chlorine atom, bromine atom, cyano group, —$OCF_3$, —$OCF_2H$, —$CF_3$, —$OCH_2CF_3$, $C_{1-12}$ alkyl group or alkoxyl group, $C_{2-12}$ alkenyl group or alkoxylalkyl group or $C_{3-12}$ alkenyloxy group; rings C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; and m represents an integer of 0 or 1 and a compound represented by the following general formula (III):

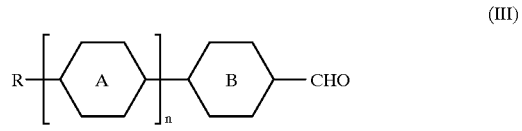

wherein R represents a $C_{1-12}$ alkyl group or alkoxyl group, $C_{2-12}$ alkenyl group or alkoxylalkyl group or $C_{3-12}$ alkenyloxy group; rings A and B each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; and n represents an integer of 0 or 1 to undergo reaction in the presence of an amine.

(8) A process for the preparation of a compound represented by the general formula (I):

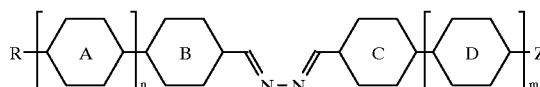 (I)

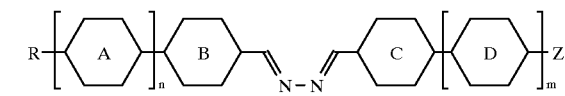 (I)

wherein m and n each independently represent an integer of 0 or 1; rings A, B, C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; R represents a $C_{1-12}$ alkyl group or alkoxyl group, $C_{2-12}$ alkenyl group or alkoxylalkyl group or $C_{3-12}$ alkenyloxy group; and Z represents a fluorine atom, chlorine atom, bromine atom, cyano group, —$OCF_3$, —$OCF_2H$, —$CF_3$, —$OCH_2CF_3$, $C_{1-12}$ alkyl group or alkoxyl group, $C_{2-12}$ alkenyl group or alkoxylalkyl group or $C_{3-12}$ alkenyloxy group, which comprises allowing a compound represented by the following general formula (IV):

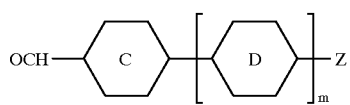 (IV)

wherein Z represents a fluorine atom, chlorine atom, bromine atom, cyano group, —$OCF_3$, —$OCF_2H$, —$CF_3$, —$OCH_2CF_3$, $C_{1-12}$ alkyl group or alkoxyl group, $C_{2-12}$ alkenyl group or alkoxylalkyl group or $C_{3-12}$ alkenyloxy group; rings C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; and m represents an integer of 0 or 1 and a compound represented by the following general formula (V):

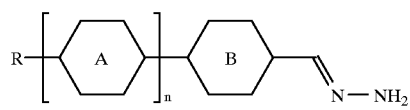 (V)

wherein R represents a $C_{1-12}$ alkyl group or alkoxyl group, $C_{2-12}$ alkenyl group or alkoxylalkyl group or $C_{3-12}$ alkenyloxy group; rings A and B each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; and n represents an integer of 0 or 1 to undergo reaction in the presence of an amine.

(9) A nematic liquid crystal composition, comprising a compound represented by the general formula (I):

wherein m and n each independently represent an integer of 0 or 1;

rings A, B, C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group;

R represents a $C_{1-12}$ alkyl group or alkoxyl group, $C_{2-12}$ alkenyl group or alkoxylalkyl group or $C_{3-12}$ alkenyloxy group; and Z represents a fluorine atom, chlorine atom, bromine atom, cyano group, —$OCF_3$, —$OCF_2H$, —$CF_3$, —$OCH_2CF_3$, $C_{1-12}$ alkyl group or alkoxyl group, $C_{2-12}$ alkenyl group or alkoxylalkyl group or $C_{3-12}$ alkenyloxy group, with the proviso that Z is not an alkyl group, cyano group, fluorine atom, chlorine atom or bromine atom when m and n each are 0 and rings B and C each are 1,4-phenylene group and R is an alkyl group.

(10) The nematic liquid crystal composition described in Clause (9), comprising a compound defined in any one of Clauses (2) to (6).

(11) A nematic liquid crystal composition, comprising as a liquid crystal component A a compound represented by the general formula (I):

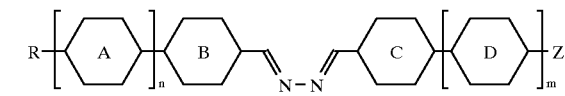 (I)

wherein m and n each independently represent an integer of 0 or 1;

rings A, B, C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group;

R represents a $C_{1-12}$ alkyl group or alkoxyl group, $C_{2-12}$ alkenyl group or alkoxylalkyl group or $C_{3-12}$ alkenyloxy group; and Z represents a fluorine atom, chlorine atom, bromine atom, cyano group, —$OCF_3$, —$OCF_2H$, —$CF_3$, —$OCH_2CF_3$, $C_{1-12}$ alkyl group or alkoxyl group, $C_{2-12}$ alkenyl group or alkoxylalkyl group or $C_{3-12}$ alkenyloxy group and as a liquid crystal component B a compound having a dielectric anisotropy of not less than +2.

(12) The nematic liquid crystal composition described in any one of Clauses (9) to (11), wherein as said liquid crystal component B there is incorporated a compound selected from the group consisting of compounds represented by the following general formulae (II-1) to (II-4):

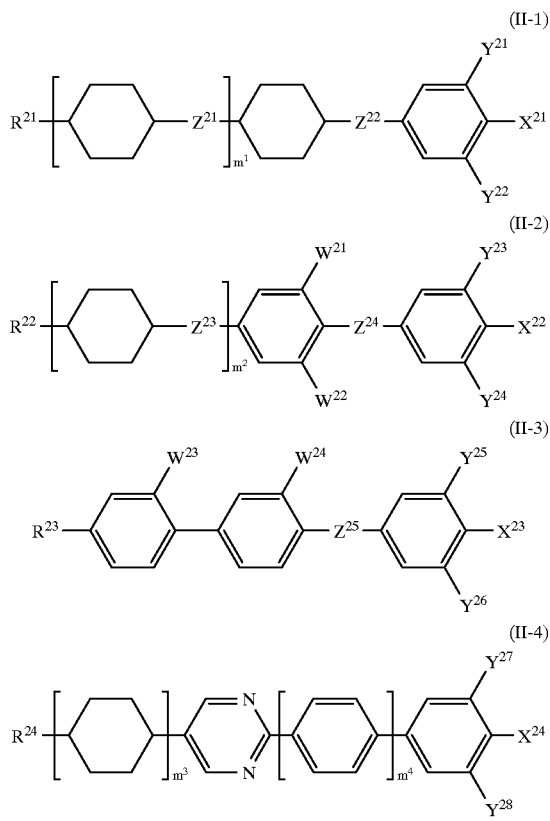

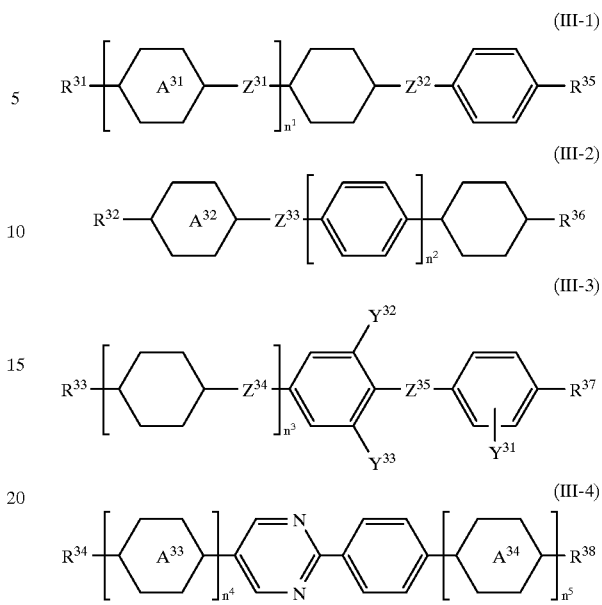

wherein $R^{21}$ to $R^{24}$ each independently represent a $C_{2-10}$ straight-chain alkyl group, alkenyl group or $C_sH_{2s+1}$—O—$C_tH_{2t}$ in which s and t each independently represent an integer of from 1 to 5;

$X^{21}$ to $X^{24}$ each independently represent a fluorine atom, chlorine atom, —$OCF_3$, —$OCHF_2$, —$CF_3$ or —CN;

$Y^{21}$ to $Y^{28}$ each independently represent a hydrogen atom or fluorine atom;

$W^{21}$ to $W^{24}$ each independently represent a hydrogen atom or fluorine atom;

$Z^{21}$ to $Z^{23}$ each independently represent a single bond, —COO—, —$CH_2CH_2$— or —$(CH_2)_4$—;

$Z^{21}$ may also represent —C≡C— or —CH=CH—;

$Z^{24}$ and $Z^{25}$ each independently represent a single bond, —COO—, —C≡C— or —CF=CF—; and $m^1$ to $m^4$ each independently represent an integer of from 0 or 1, with the proviso that $m^3+m^4$ make an integer of 0 or 1, and hydrogen atoms in the cyclohexane ring in the various compounds may be replaced by deuterium atoms (D).

(13) The nematic liquid crystal composition described in any one of Clauses (9) to (12), comprising as a liquid crystal component C a compound having a dielectric anisotropy of from −2 to +2.

(14) The nematic liquid crystal composition described in Clause (13), wherein as said liquid crystal component C there is incorporated a compound selected from the group consisting of compounds represented by the following general formulae (III-1) to (III-4):

wherein $R^{31}$ to $R^{34}$ each independently represent a $C_{2-7}$ straight-chain alkyl group or alkenyl group;

$R^{35}$ to $R^{38}$ each independently represent a $C_{1-7}$ straight-chain alkyl group, alkoxy group, alkenyl group, alkenyloxy group or $C_uH_{2u+1}$—O—$C_vH_{2v}$, in which u and v each independently represent an integer of from 1 to 5;

$Y^{31}$ represents a hydrogen atom, fluorine atom or —$CH_3$;

$Y^{32}$ and $Y^{33}$ each independently represent a hydrogen atom or fluorine atom;

$Z^{31}$ to $Z^{34}$ each independently represent a single bond, —COO—, —$CH_2CH_2$— or —$(CH_2)_4$—;

$Z^{21}$ may also represent —C≡C— or —CH=CH—;

$Z^{35}$ represents a single bond, —C≡C—, —COO— or —CF=CF—;

rings $A^{31}$ and $A^{32}$ each independently represent a cyclohexane ring or cyclohexene ring;

rings $A^{33}$ and $A^{34}$ each independently represent a cyclohexane ring or benzene ring; and $n^1$ to $n^5$ each independently represent an integer of 0 or 1, with the proviso that $n^4+n^5$ make an integer of 0 or 1, and hydrogen atoms in the cyclohexane ring in the various compounds may be replaced by deuterium atoms (D).

(15) The nematic liquid crystal composition described in any one of Clauses (9) to (14), comprising a compound represented by the general formula (I"):

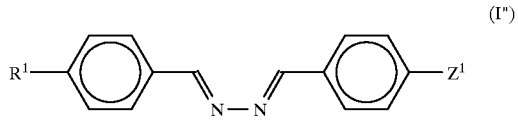

wherein $R^1$ represents a $C_{1-10}$ alkyl group, or alkoxyl group and $Z^1$ represents a $C_{1-10}$ alkyl group, alkoxyl group, fluorine atom, chlorine atom, cyano group or hydrogen atom.

(16) The nematic liquid crystal composition described in any one of Clauses (9) to (15), comprising a compound represented by the general formula (I'"):

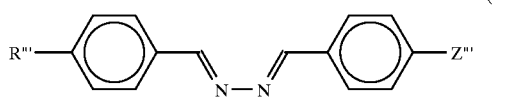

wherein R''' and Z''' each independently represent a $C_{1-10}$ alkyl group or $C_{2-7}$ alkenyl group.

(17) An active matrix, twisted nematic or super twisted nematic liquid crystal display system, comprising a nematic liquid crystal composition described in any one of Clauses (9) to (16).

(18) A light-scattering type liquid crystal display system, comprising a light-control layer having a nematic liquid crystal composition described in any one of Clauses (9) to (16) and a transparent solid substance incorporated therein.

EXAMPLES

The present invention will be further described in the following examples, but the present invention should not be construed as being limited thereto.

The structure of various compounds was identified by nuclear magnetic resonance spectrum (NMR), mass spectrum (MS) and infrared absorption spectrum (IR). The measurement of phase transition temperature was effected by means of a polarizing microscope equipped with a temperature-controlling stage and a differential scanning calorimeter (DSC) in combination. The term "%" as used for composition is meant to indicate "%" by weight.

EXAMPLE 1

Synthesis of 1-(4-fluorobenzylidene)-2-(4-propylbenzylidene)hydrazine (Compound No. 2 set forth in Table 1)

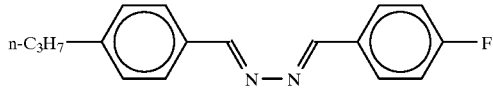

To 140 g of a monohydrate of hydrazine was added a solution of 50 g of 4-propylbenzaldehyde in 250 ml of ethanol. The mixture was stirred at room temperature for 1 hour. To the mixture was then added 400 ml of dichloromethane. The mixture was then washed with 300 ml of saturated aqueous solution of sodium hydrogencarbonate three times. To the resulting organic phase was then added 15 ml of triethylamine. The mixture was then dehydrated and dried over anhydrous sodium sulfate. The solvent was then distilled off under reduced pressure. To the residue was then added 15 ml of triethylamine. To the mixture were then added 250 ml of ethanol and 43 g of 4-fluorobenzaldehyde. The mixture was then stirred at room temperature for 6 hours. To the mixture was then added 400 ml of dichloromethane. The mixture was then washed with 300 ml of saturated aqueous solution of sodium bicarbonate. The solvent was then distilled off under reduced pressure. The residue was purified through alumina (basic) column chromatography (dichloromethane), and then recrystallized from methanol to obtain 26.9 g of 1-(4-fluorobenzylidene)-2-(4-propylbenzylidene)hydrazine. The compound thus obtained had a melting point of 70.5° C. and exhibited nematic phase up to 96.5° C.

The foregoing procedure was followed except that 4-methylbenzaldehyde, 4-ethylbenzaldehyde, 4-butylbenzaldehyde, 4-pentylbenzaldehyde, 4-heptylbenzaldehyde or 4-methoxybenzaldehyde was used instead of 4-propylbenzaldehyde. As a result, the following compounds were obtained:

1-(4-fluorobenzylidene)-2-(4-methylbenzylidene)hydrazine
1-(4-fluorobenzylidene)-2-(4-ethylbenzylidene)hydrazine (I-1)
1-(4-fluorobenzylidene)-2-(4-butylbenzylidene)hydrazine (I-3)
1-(4-fluorobenzylidene)-2-(4-pentylbenzylidene)hydrazine
1-(4-fluorobenzylidene)-2-(4-heptylbenzylidene)hydrazine
1-(4-fluorobenzylidene)-2-(4-methoxybenzylidene)hydrazine

EXAMPLE 2

Synthesis of 1-(4-trifluoromethoxybenzylidene)-2-(4-propylbenzylidene)hydrazine (Compound No. 4 set forth in Table 1)

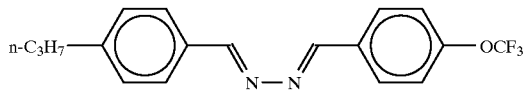

The procedure of Example 1 was followed except that 4-trifluoromethoxybenzene was used instead of 4-fluorobenzaldehyde. As a result, 1-(4-trifluoromethoxybenzylidene)-2-(4-propylbenzylidene)hydrazine was obtained. The phase transition temperature of this compound was set forth in Table 1.

Similarly, the following compounds were obtained:
1-(4-trifluoromethoxybenzylidene)-2-(4-methylbenzylidene)hydrazine
1-(4-trifluoromethoxybenzylidene)-2-(4-ethylbenzylidene)hydrazine
1-(4-trifluoromethoxybenzylidene)-2-(4-butylbenzylidene)hydrazine
1-(4-trifluoromethoxybenzylidene)-2-(4-pentylbenzylidene)hydrazine
1-(4-trifluoromethoxybenzylidene)-2-(4-heptylbenzylidene)hydrazine
1-(4-trifluoromethoxybenzylidene)-2-(4-methoxybenzylidene)hydrazine
1-(4-trifluoroethylbenzylidene)-2-(4-methylbenzylidene)hydrazine
1-(4-trifluoromethylbenzylidene)-2-(4-ethylbenzylidene)hydrazine
1-(4-trifluoroethylbenzylidene)-2-(4-propylbenzylidene)hydrazine
1-(4-trifluoromethylbenzylidene)-2-(4-butylbenzylidene)hydrazine
1-(4-trifluoromethylbenzylidene)-2-(4-pentylbenzylidene)hydrazine
1-(4-trifluoromethylbenzylidene)-2-(4-heptylbenzylidene)hydrazine
1-(4-trifluoromethylbenzylidene)-2-(4-methoxybenzylidene)hydrazine
1-(4-difluoromethoxybenzylidene)-2-(4-methylbenzylidene)hydrazine
1-(4-difluoromethoxybenzylidene)-2-(4-ethylbenzylidene)hydrazine
1-(4-difluoromethoxybenzylidene)-2-(4-propylbenzylidene)hydrazine
1-(4-difluoromethoxybenzylidene)-2-(4-butylbenzylidene)hydrazine
1-(4-difluoromethoxybenzylidene)-2-(4-pentylbenzylidene)hydrazine 1-(4-difluoromethoxybenzylidene)-2-(4-heptylbenzylidene)hydrazine 1-(4-difluoromethoxybenzylidene)-2-(4-methoxybenzylidene)hydrazine 1-[4-(2,2,2-trifluoroethoxy)benzylidene]-2-(4-methylbenzylidene)hydrazine 1-[4-(2,2,2-trifluoroethoxy)benzylidene]-2-(4-ethylbenzylidene)hydrazine 1-[4-(2,2,2-trifluoroethoxy)benzylidene]-2-(4-propylbenzylidene)hydrazine 1-[4-(2,2,2-trifluoroethoxy)benzylidene]-2-(4-butylbenzylidene)hydrazine 1-[4-(2,2,2-trifluoroethoxy)benzylidene]-2-(4-pentylbenzylidene)hydrazine 1-[4-(2,2,2-trifluoroethoxy)benzylidene]-2-(4-heptylbenzylidene)hydrazine 1-[4-(2,2,2-trifluoroethoxy)benzylidene1]-2-(4-methoxybenzylidene)hydrazine

EXAMPLE 3

Preparation of liquid crystal composition (1)

The host liquid crystal (H) having a low viscosity and a broad liquid crystal phase temperature range

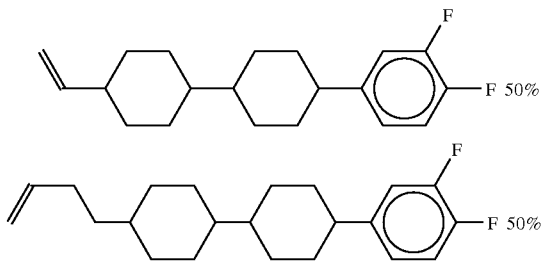

exhibits nematic phase at a temperature of not higher than 116.7° C. and shows a melting point of 11° C. This host liquid crystal was then packed into a 4.5 μm thick TN cell to prepare a liquid crystal device. The liquid crystal device thus prepared was then measured for switching time. The results were 21.5 msec. (Under the application of voltage when the decay time and the rise time are equal), the liquid crystal device exhibited a threshold voltage of 1.88 V.

A composition (M-2) consisting of 80% of this host liquid crystal (H) and 20% of Compound No. 2 obtained in Example 1 was prepared. The composition (M-2) exhibited an upper nematic phase temperature limit (TN-1) of 104° C., which is not too a great drop from that of the host liquid crystal (H). A liquid crystal device was then prepared from this composition in the same manner as mentioned above. The liquid crystal device thus prepared was then measured for switching time. The results were 14.0 msec., which demonstrates that the response rate is very fast. This device exhibited a threshold voltage of 2.07 V, which is not too a great increase from that of the host liquid crystal (H).

This composition was allowed to stand at a temperature of 0° C. for 24 hours. As a result, no crystallization was observed.

A liquid crystal composition (M-4) consisting of 80% of the host liquid crystal (H) and the same amount (20%) of Compound No. 4 obtained in Example 2 as in Compound No. 2 was prepared. This liquid crystal composition (M-4) exhibited an upper nematic phase temperature limit $(T_{N-1})$ of 98° C., which is a slight drop from that of the composition (M-2). A liquid crystal device was then prepared from this composition in the same manner as mentioned above. The liquid crystal device thus prepared was then measured for switching time. The results were 15.8 msec., which demonstrates that the response rate is very fast, though slightly lower than that of the composition (M-2). This device exhibited a threshold voltage of 1.85 V, which is a drop from that of the composition (M-2).

This composition was allowed to stand at a temperature of 0° C. for 24 hours. As a result, this composition, too, showed no crystallization.

EXAMPLE 4

Synthesis of 1-(3,4-difluorobenzylidene)-2-(4-propylbenzylidene)hydrazine (Compound No. 7 set forth in Table 1)

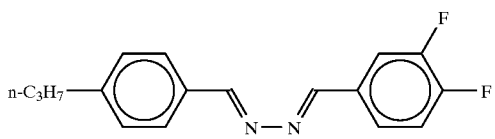

To 40 g of a monohydrate of hydrazine was added a solution of 10 g of 4-propylbenzaldehyde in 50 ml of ethanol. The mixture was stirred at room temperature for 30 minutes. To the mixture was then added 150 ml of saturated aqueous solution of sodium bicarbonate. To the mixture was then added 100 ml of dichloromethane. The mixture was then washed with 150 ml of saturated aqueous solution of sodium bicarbonate twice. To the resulting organic phase was then added 5 ml of triethylamine. The mixture was then dehydrated and dried over anhydrous sodium sulfate. The solvent was then distilled off under reduced pressure. To the residue was then added 5 ml of triethylamine. To the mixture were then added 50 ml of ethanol and 8.5 g of 3,4-difluorobenzaldehyde. The mixture was then stirred at room temperature for 6.5 hours. To the mixture was then added 150 ml of saturated aqueous solution of sodium bicarbonate. To the mixture was then added 100 ml of dichloromethane. The mixture was then washed with 150 ml of saturated aqueous solution of sodium bicarbonate twice. The solvent was then distilled off under reduced pressure. The residue was purified through alumina (basic) column chromatography (dichloromethane), and then recrystallized from methanol to obtain 5.7 g of 1-(3,4-difluorobenzylidene)-2-(4-propylbenzylidene)hydrazine. The compound thus obtained had a melting point of 50° C. and exhibited nematic phase up to 59.5° C.

The foregoing procedure was followed except that 4-methylbenzaldehyde, 4-ethylbenzaldehyde, 4-butylbenzaldehyde, 4-pentylbenzaldehyde, 4-heptylbenzaldehyde or 4-methoxybenzaldehyde was used instead of 4-propylbenzaldehyde. As a result, the following compounds were obtained:

1-(3,4-difluorobenzylidene)-2-(4-methylbenzylidene)hydrazine 1-(3,4-difluorobenzylidene)-2-(4-ethylbenzylidene)hydrazine 1-(3,4-difluorobenzylidene)-2-(4-butylbenzylidene)hydrazine 1-(3,4-difluorobenzylidene)-2-(4-pentylbenzylidene)hydrazine 1-(3,4-difluorobenzylidene)-2-(4-heptylbenzylidene)hydrazine 1-(3,4-difluorobenzylidene)-2-(4-methoxybenzylidene)hydrazine

EXAMPLE 5

Synthesis of 1-(3,4,5-trifluorobenzylidene)-2-(4-propylbenzylidene)hydrazine (Compound No. 8 set forth in Table 1)

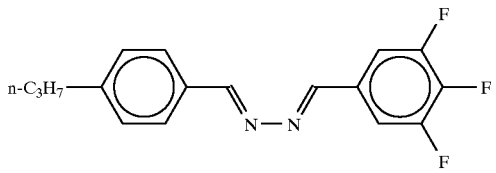

The procedure of Example 4 was followed except that 3,4,5-trifluorobenzaldehyde was used instead of 3,4-difluorobenzaldehyde. As a result, 1-(3,4,5-trifluoro benzylidene)-2-(4-propylbenzylidene)hydrazine (Compound No. 8 set forth in Table 1) was obtained. The phase transition temperature of this compound was set forth in Table 1.

Similarly, the following compounds were obtained:
1-(3,4,5-trifluorobenzylidene)-2-(4-methylbenzylidene)hydrazine
1-(3,4,5-trifluorobenzylidene)-2-(4-ethylbenzylidene)hydrazine
1-(3,4,5-trifluorobenzylidene)-2-(4-butylbenzylidene)hydrazine
1-(3,4,5-triflurobenzyl idene)-2-(4-pentylbenzylidene)hydrazine
1-(3,4,5-trifluorobenzylidene)-2-(4-heptylbenzylidene)hydrazine
1-(3,4,5-trifluorobenzylidene)-2-(4-methoxybenzylidene)hydrazine
1-(3-fluoro-4-trifluoromethoxybenzylidene)-2-(4-methylbenzylidene )hydrazine
1-(3-fluoro-4-trifluoromethoxybenzylidene)-2-(4-ethylbenzylidene)hydrazine
1-(3-fluoro-4-trifluoromethoxybenzylidene)-2-(4-propylbenzyl idene)hydrazine
1-(3-fluoro-4-trifluoromethoxybenzylidene)-2-(4-butylbenzylidene)hydrazine
1-(3-fluoro-4-trifluoromethoxybenzylidene)-2-(4-pentylbenzylidene)hydrazine
1-(3-fluoro-4-trifluoromethoxybenzylidene)-2-(4-heptylbenzylidene)hydrazine
1-(3-fluoro-4-trifluoromethoxybenzylidene)-2-(4-methoxybenzylidene)hydrazine
1-(3,5-difluoro-4-trifluoromethoxybenzylidene)-2-(4-methylbenzylidene)hydrazine
1-(3,5-difluoro-4-trifluoromethoxybenzylidene)-2-(4-ethylbenzylidene)hydrazine
1-(3,5-difluoro-4-trifluoromethoxybenzylidene)-2-(4-propylbenzylidene)hydrazine
1-(3,5-difluoro-4-trifluoromethoxybenzylidene)-2-(4-butylbenzylidene)hydrazine
1-(3,5-difluoro-4-trifluoromethoxybenzylidene)-2-(4-pentylbenzylidene)hydrazine
1-(3,5-difluoro-4-trifluoromethoxybenzylidene)-2-(4-heptylbenzylidene)hydrazine
1-(3,5-difluoro-4-trifluoromethoxybenzylidene)-2-(4-methoxybenzylidene)hydrazine
1-(3-fluoro-4-trifluoromethylbenzylidene)-2-(4-methylbenzyl idene)hydrazine
1-(3-fluoro-4-trifluoromethylbenzylidene)-2-(4-ethylbenzylidene)hydrazine
1-(3-fluoro-4-trifluoromethylbenzylidene)-2-(4-propylbenzylidene)hydrazine
1-(3-fluoro-4-trifluoromethylbenzylidene)-2-(4-butylbenzylidene)hydrazine
1-(3-fluoro-4-trifluoromethylbenzylidene)-2-(4-pentylbenzylidene)hydrazine
1-(3-fluoro-4-trifluoromethylbenzylidene)-2-(4-heptylenzylidene)hydrazine
1-(3-fluoro-4-trifluoromethylbenzylidene)-2-(4-methoxybenzylidene)hydrazine
1-(3,5-difluoro-4-trifluoromethylbenzylidene)-2-(4-methylbenzylidene)hydrazine
1-(3,5-difluoro-4-trifluoromethylbenzylidene)-2-(4-ethylbenzylidene)hydrazine
1-(3,5-difluoro-4-trifluoromethylbenzylidene)-2-(4-propylbenzylidene)hydrazine
1-(3,5-difluoro-4-trifluoromethylbenzylidene)-2-(4-butylbenzylidene)hydrazine
1-(3,5-difluoro-4-trifluoromethylbenzylidene)-2-(4-pentylbenzylidene)hydrazine
1-(3,5-difluoro-4-trifluoromethylbenzylidene)-2-(4-heptylbenzylidene)hydrazine
1-(3,5-difluoro-4-trifluoromethylbenzylidene)-2-(4-methoxybenzylidene)hydrazine
1-(3,5-difluoro-4-trifluoromethylbenzylidene)-2-(4-methylbenzylidene)hydrazine
1-(3,5-difluoro-4-trifluoromethylbenzylidene)-2-(4-ethylbenzylidene)hydrazine
1-(3,5-difluoro-4-trifuoromethylbenzy idene)-2-(4-propylbenzyl idene)hydrazine
1-(3,5-difluoro-4-trifluoromethylbenzylidene)-2-(4-butylbenzylidene)hydrazine
1-(3,5-difluoro-4-trifluoromethylbenzylidene)-2-(4-pentylbenzylidene)hydrazine
1-(3,5-difluoro-4-trifluoromethylbenzylidene)-2-(4-heptylbenzylidene)hydrazine
1-(3,5-difluoro-4-trifluoromethylbenzyl idene)-2-(4-methoxybenzylidene)hydrazine
1-(3-fluoro-4-difluoromethoxybenzylidene)-2-(4-methylbenzylidene)hydrazine
1-(3-fluoro-4-difluoromethoxybenzylidene)-2-(4-ethylbenzylidene)hydrazine
1-(3-fluoro-4-difluoromethoxybenzyidene)-2-(4-propylbenzylidene)hydrazine
1-(3-fluoro-4-difluoromethoxybenzylidene)-2-(4-butylbenzylidene)hydrazine
1-(3-fluoro-4-difluoromethoxybenzylidene)-2-(4-pentylbenzyl idene)hydazine
1-(3-fluoro-4-difluoromethoxybenzylidene)-2-(4-heptylbenzylidene)hydrazine
1-(3-fluoro-4-difluoromethoxybenzyl idene )-2-(4-methoxybenzylidene)hydrazine
1-(3,5-difluoro-4-dif luoromethoxybenzyl idene)-2-(4-methylbenzylidene)hydrazine
1-(3,5-difluoro-4-difluoromethoxybenzylidene)-2-(4-ethylbenzylidene)hydrazine
1-(3,5-difluoro-4-difluoromethoxybenzylidene)-2-(4-propylbenzylidene)hydrazine
1-(3,5-difluoro-4-difluoromethoxybenzylidene)-2-(4-butylbenzylidene)hydrazine
1-(3,5-difluoro-4-difluoromethoxybenzyl idene)-2-(4-pentylbenzylidene)hydrazine
1-(3,5-difluoro-4-difluoromethoxybenzylidene)-2-(4-heptylbenzylidene)hydrazine
1-(3,5-difluoro-4-difluoromethoxybenzylidene)-2-(4-methoxybenzylidene)hydrazine
1-(3-fluoro-4-chlorobenzylidene)-2-(4-methylbenzylidene)hydrazine
1-(3-fluoro-4-chlorobenzylidene)-2-(4-ethylbenzylidene)hydrazine 1-(3-fluoro-4-chlorobenzylidene)-2-(4-propylbenzylidene)hydrazine
1-(3-fluoro-4-chlorobenzylidene)-2-(4-butylbenzylidene)hydrazine
1-(3-fluoro-4-chlorobenzylidene)-2-(4-pentylbenzylidene)hydrazine
1-(3-fluoro-4-chlorobenzylidene)-2-(4-heptylbenzylidene)hydrazine
1-(3-fluoro-4-chlorobenzylidene)-2-(4-methoybenzylidene)hydrazine
1-(3,5-difluoro-4-chlorobenzylidene)-2-(4-methylbenzylidene)hydrazine
1-(3,5-difluoro-4-chlorobenzylidene)-2-(4-ethylbenzylidene)hydrazine
1-(3,5-difluoro-4-chlorobenzylidene)-2-(4-propylbenzylidene)hydrazine
1-(3,5-difluoro-4-chlorobenzylidene)-2-(4-butylbenzylidene)hydrazine
1-(3,5-difluoro-4-chlorobenzylidene)-2-(4-pentylbenzylidene)hydrazine
1-(3,5-difluoro-4-chlorobenzylidene)-2-(4-heptylbenzylidene)hydrazine
1-(3,5-difluoro-4-chlorobenzylidene)-2-(4-methoxybenzylidene)hydrazine
1-[3-fluoro-4-(2,2,2-trifluoroethoxy)benzylidene]-2-(4-methylbenzylidene)hydrazine
1-[3-fluoro-4-(2,2,2-trifluoroethoxy)benzylidene]-2-(4-ethylbenzylidene)hydrazine
1-[3-fluoro-4-(2,2,2-trifluoroethoxy)benzylidene]-2-(4-propylbenzylidene)hydrazine
1-[3-fluoro-4-(2,2,2-trifluoroethoxy)benzylidene]-2-(4-butylbenzylidene)hydrazine
1-[3-fluoro-4-(2,2,2-trifluoroethoxy)benzylidene]-2-(4-pentylbenzylidene)hydrazine
1-[3-fluoro-4-(2,2,2-trifluoroethoxy)benzylidene]-2-(4-heptylbenzylidene)hydrazine
1-[3-fluoro-4-(2,2,2-trifluoroethoxy)benzylidene]-2-(4-methoxybenzylidene)hydrazine
1-[3,5-difluoro-4-(2,2,2-trifluoroethoxy)benzylidene]-2-(4-methylbenzylidene)hydrazine
1-[3,5-difluoro-4-(2,2,2-trifluoroethoxy)benzylidene]-2-(4-ethylbenzylidene)hydrazine
1-[3,5-difluoro-4-(Z,2,2-trifluoroethoxy)benzylidene]-2-(4-propylbenzylidene)hydrazine
1-[3,5-difluoro-4-(2,2,2-trifluoroethoxy)benzylidene]-2-(4-butylbenzylidene)hydrazine
1-[3,5-difluoro-4-(2,2,2-trifluoroethoxy)benzylidene]-2-(4-pentylbenzylidene)hydrazine
1-[3,5-difluoro-4-(2,2,2-trifluoroethoxy)benzylidene]-2-(4-heptylbenzylidene)hydrazine
1-[3,5-difluoro-4-(2,2,2-trifluoroethoxy)benzylidene]-2-(4-methoxybenzylidene)hydrazine
1-(3-fluoro-4-cyanobenzylidene)-2-(4-methylbenzylidene)hydrazine
1-(3-fluoro-4-cyanobenzylidene)-2-(4-ethylbenzylidene)hydrazine
1-(3-fluoro-4-cyanobenzylidene)-2-(4-propylbenzylidene)hydrazine
1-(3-fluoro-4-cyanobenzylidene)-2-(4-butylbenzylidene)hydrazine
1-(3-fluoro-4-cyanobenzylidene)-2-(4-pentylbenzylidene)hydrazine
1-(3-fluoro-4-cyanobenzylidene)-2-(4-heptylbenzylidene)hydrazine
1-(3-fluoro-4-cyanobenzylidene)-2-(4-4-methoxybenzylidene)hydrazine
1-(3,5-difluoro-4-cyanobenzylidene)-2-(4-methylbenzylidene)hydrazine
1-(3,5-difluoro-4-cyanobenzylidene)-2-(4-ethylbenzylidene)hydrazine
1-(3,5-difluoro-4-cyanobenzylidene)-2-(4-propylbenzylidene)hydrazine
1-(3,5-difluoro-4-cyanobenzylidene)-2-(4-butylbenzylidene)hydrazine
1-(3,5-difluoro-4-cyanobenzylidene)-2-(4-pentylbenzylidene)hydrazine
1-(3,5-difluoro-4-cyanobenzylidene)-2-(4-heptylbenzylidene)hydrazine
1-(3,5-difluoro-4-cyanobenzylidene)-2-(4-methoxybenzylidene)hydrazine
1-(3-fluoro-4-methylbenzylidene)-2-(4-methylbenzylidene)hydrazine
1-(3-fluoro-4-methylbenzylidene)-2-(4-ethylbenzylidene)hydrazine
1-(3-fluoro-4-methylbenzylidene)-2-(4-propylbenzylidene)hydrazine
1-(3-fluoro-4-methylbenzylidene)-2-(4-butylbenzylidene)hydrazine
1-(3-fluoro-4-methylbenzylidene)-2-(4-pentylbenzylidene)hydrazine
1-(3-fluoro-4-methylbenzylidene)-2-(4-heptylbenzylidene)hydrazine
1-(3-fluoro-4-methylbenzylidene)-2-(4-methoxybenzylidene)hydrazine
1-(3,5-difluoro-4-methylbenzylidene)-2-(4-methylbenzylidene)hydrazine
1-(3,5-difluoro-4-methylbenzylidene)-2-(4-ethylbenzylidene)hydrazine
1-(3,5-difluoro-4-methylbenzylidene)-2-(4-propylbenzylidene)hydrazine
1-(3,5-difluoro-4-methylbenzylidene)-2-(4-butylbenzylidene)hydrazine
1-(3,5-difluoro-4-methylbenzylidene)-2-(4-pentylbenzylidene)hydrazine
1-(3,5-difluoro-4-methylbenzylidene)-2-(4-heptylbenzylidene)hydrazine
1-(3,5-difluoro-4-methylbenzylidene)-2-(4-methoxybenzylidene)hydrazine
1-(3-fluoro-4-methoxybenzylidene)-2-(4-methylbenzylidene)hydrazine
1-(3-fluoro-4-methoxybenzylidene)-2-(4-ethylbenzylidene)hydrazine
1-(3-fluoro-4-methoxybenzylidene)-2-(4-propylbenzylidene)hydrazine
1-(3-fluoro-4-methoxybenzylidene)-2-(4-butylbenzylidene)hydrazine
1-(3-fluoro-4-methoxybenzylidene)-2-(4-pentylbenzylidene)hydrazine
1-(3-fluoro-4-methoxybenzylidene)-2-(4-heptylbenzylidene)hydrazine
1-(3-fluoro-4-methoxybenzylidene)-2-(4-methoxybenzylidene)hydrazine
1-(3,5-difluoro-4-methoxybenzylidene)-2-(4-methylbenzylidene)hydrazine
1-(3,5-difluoro-4-methoxybenzylidene)-2-(4-ethylbenzylidene)hydrazine
1-(3,5-difluoro-4-ethoxybenzylidene)-2-(4-propylbenzylidene)hydrazine
1-(3,5-difluoro-4-methoxybenzylidene)-2-(4-butylbenzylidene)hydrazine
1-(3,5-difluoro-4-methoxybenzylidene)-2-(4-pentylbenzylidene)hydrazine
1-(3,5-difluoro-4-methoxybenzylidene)-2-(4-heptylbenzylidene)hydrazine
1-(3,5-difluoro-4-methoxybenzylidene)-2-(4-methoxybenzylidene)hydrazine 1-(3-fluoro-4-ethylbenzylidene)-2-(4-methylbenzylidene)hydrazine
1-(3-fluoro-4-ethylbenzylidene)-2-(4-ethylbenzylidene)hydrazine
1-(3-fluoro-4-ethylbenzylidene)-2-(4-propylbenzylidene)hydrazine
1-(3-fluoro-4-ethylbenzylidene)-2-(4-butylbenzylidene)hydrazine
1-(3-fluoro-4-ethylbenzylidene)-2-(4-pentylbenzylidene)hydrazine
1-(3-fluoro-4-ethylbenzylidene)-2-(4-heptylbenzylidene)hydrazine
1-(3-fluoro-4-ethylbenzylidene)-2-(4-methoxybenzylidene)hydrazine
1-(3,5-difluoro-4-ethylbenzylidene)-2-(4-methylbenzylidene)hydrazine
1-(3,5-difluoro-4-ethylbenzylidene)-2-(4-ethylbenzylidene)hydrazine
1-(3,5-difluoro-4-ethylbenzylidene)-2-(4-propylbenzylidene)hydrazine
1-(3,5-difluoro-4-ethylbenzylidene)-2-(4-butylbenzylidene)hydrazine
1-(3,5-difluoro-4-ethylbenzylidene)-2-(4-pentylbenzylidene)hydrazine
1-(3,5-difluoro-4-ethylbenzylidene)-2-(4-heptylbenzylidene)hydrazine
1-(3,5-difluoro-4-ethylbenzylidene)-2-(4-methoxybenzylidene)hydrazine
1-(3-fluoro-4-propylbenzylidene)-2-(4-methylbenzylidene)hydrazine
1-(3-fluoro-4-propylbenzylidene)-2-(4-ethylbenzylidene)hydrazine
1-(3-fluoro-4-propylbenzylidene)-2-(4-propylbenzylidene)hydrazine
1-(3-fluoro-4-propylbenzylidene)-2-(4-butylbenzylidene)hydrazine
1-(3-fluoro-4-propylbenzylidene)-2-(4-pentylbenzylidene)hydrazine
1-(3-fluoro-4-propylbenzylidene)-2-(4-heptybenzylidene)hydrazine
1-(3-fluoro-4-propylbenzylidene)-2-(4-methoxybenzylidene)hydrazine
1-(3,5-difluoro-4-propylbenzylidene)-2-(4-methylbenzylidene)hydrazine
1-(3,5-difluoro-4-propylbenzylidene)-2-(4-ethylbenzylidene)hydrazine
1-(3,5-difluoro-4-propylbenzylidene)-2-(4-propylbenzylidene)hydrazine
1-(3,5-difluoro-4-propylpropylbenzylidene)-2-(4-butylbenzylidene)hydrazine
1-(3,5-difluoro-4-propylbenzylidene)-2-(4-pentylbenzylidene)hydrazine
1-(3,5-difluoro-4-propylbenzylidene)-2-(4-heptylbenzylidene)hydrazine
1-(3,5-difluoro-4-propylbenzylidene)-2-(4-methoxybenzylidene)hydrazine
1-(3-fluoro-4-allyloxybenzylidene)-2-(4-methylbenzylidene)hydrazine
1-(3-fluoro-4-allyloxybenzylidene)-2-(4-ethylbenzylidene)hydrazine
1-(3-fluoro-4-allyloxybenzylidene)-2-(4-propylbenzylidene)hydrazine
1-(3-fluoro-4-allyloxybenzylidene)-2-(4-butylbenzylidene)hydrazine
1-(3-fluoro-4-allyloxybenzylidene)-2-(4-pentylbenzylidene)hydrazine
1-(3-fluoro-4-allyloxybenzylidene)-2-(4-heptylbenzylidene)hydrazine
1-(3-fluoro-4-allyloxybenzylidene)-2-(4-methoxybenzylidene)hydrazine
1-(3,5-difluoro-4-allyloxybenzylidene)-2-(4-methylbenzylidene)hydrazine
1-(3,5-difluoro-4-allyloxybenzylidene)-2-(4-ethylbenzylidene)hydrazine
1-(3,5-difluoro-4-allyloxybenzylidene)-2-(4-propylbenzylidene)hydrazine
1-(3,5-difluoro-4-allyloxybenzylidene)-2-(4-butylbenzylidene)hydrazine
1-(3,5-difluoro-4-allyloxybenzylidene)-2-(4-pentylbenzylidene)hydrazine
1-(3,5-difluoro-4-allyloxybenzylidene)-2-(4-heptylbenzylidene)hydrazine
1-(3,5-difluoro-4-allyloxybenzylidene)-2-(4-methoxybenzylidene)hydrazine
1-(4-fluorobenzylidene)-2-(2-fluoro-4-methylbenzylidene)hydrazine
1-(4-fluorobenzylidene)-2-(2-fluoro-4-ethylbenzylidene)hydrazine
1-(4-fluorobenzylidene)-2-(2-fluoro-4-propylbenzylidene)hydrazine
1-(4-fluorobenzylidene)-2-(2-fluoro-4-butylbenzylidene)hydrazine
1-(4-fluorobenzylidene)-2-(2-fluoro-4-pentylbenzylidene)hydrazine
1-(4-fluorobenzylidene)-2-(2-fluoro-4-heptylbenzylidene)hydrazine
1-(4-fluorobenzylidene)-2-(2-fluoro-4-methoxybenzylidene)hydrazine
1-(3,4-difluorobenzylidene)-2-(2-fluoro-4-methylbenzylidene)hydrazine
1-(3,4-difluorobenzylidene)-2-(2-fluoro-4-methylbenzylidene)hydrazine
1-(3,4-difluorobenzylidene)-2-(2-fluoro-4-propylbenzylidene)hydrazine
1-(3,4-difluorobenzylidene)-2-(2-fluoro-4-butylbenzylidene)hydrazine
1-(3,4-difluorobenzylidene)-2-(2-fluoro-4-pentylbenzylidene)hydrazine
1-(3,4-difluorobenzylidene)-2-(2-fluoro-4-methoxybenzylidene)hydrazine
1-(3,4,5-trifluorobenzylidene)-2-(2-fluoro-4-methylbenzylidene)hydrazine
1-(3,4,5-trifluorobenzylidene)-2-(2-fluoro-4-ethylbenzylidene)hydrazine
1-(3,4,5-trifluorobenzylidene)-2-(2-fluoro-4-propylbenzylidene)hydrazine
1-(3,4,5-trifluorobenzylidene)-2-(2-fluoro-4-butylbenzylidene)hydrazine
1-(3,4,5-trifluorobenzylidene)-2-(2-fluoro-4-pentylbenzylidene)hydrazine
1-(3,4,5-trifluorobenzylidene)-2-(2-fluoro-4-heptylbenzylidene)hydrazine
1-(3,4,5-trifluorobenzylidene)-2-(2-fluoro-4-methoxybenzylidene)hydrazine
1-(4-fluorobenzylidene)-2-(2,6-difluoro-4-methylbenzylidene)hydrazine
1-(4-fluorobenzylidene)-2-(2,6-difluoro-4-ethylbenzylidene)hydrazine
1-(4-fluorobenzylidene)-2-(2,6-difluoro-4-propylbenzylidene)hydrazine
1-(4-fluorobenzylidene)-2-(2,6-difluoro-4-butylbenzylidene)hydrazine
1-(4-fluorobenzylidene)-2-(2,6-difluoro-4-pentylbenzylidene)hydrazine
1-(4-fluorobenzylidene)-2-(2,6-difluoro-4-heptylbenzylidene)hydrazine 1-(3,4-difluorobenzylidene)-2-(2,6-difluoro-4-methoxybenzylidene)hydrazine
1-(3,4-difluorobenzylidene)-2-(2,6-difluoro-4-methylbenzylidene)hydrazine
1-(3,4-difluorobenzylidene)-2-(2,6-difluoro-4-propylbenzylidene)hydrazine
1-(3,4-difluorobenzylidene)-2-(2,6-difluoro-4-butylbenzylidene)hydrazine
1-(3,4-difluorobenzylidene)-2-(2,6-difluoro-4-pentylbenzylidene)hydrazine
1-(3,4-difluorobenzylidene)-2-(2,6-difluoro-4-heptylbenzylidene)hydrazine
1-(3,4-difluorobenzylidene)-2-(2,6-difluoro-4-methoxybenzylidene)hydrazine
1-(3,4-difluorobenzylidene)-2-(2,6-difluoro-4-methylbenzylidene)hydrazine
1-(3,4,5-trifluorobenzylidene)-2-(2,6-difluoro-4-ethylbenzylidene)hydrazine
1-(3,4,5-trifluorobenzylidene)-2-(2,6-difluoro-4-ethylbenzylidene)hydrazine
1-(3,4,5-trifluorobenzylidene)-2-(2,6-difluoro-4-propylbenzylidene)hydrazine
1-(3,4,5-trifluorobenzylidene)-2-(2,6-difluoro-4-butylpentylbenzylidene)hydrazine
1-(3,4,5-trifluorobenzylidene)-2-(2,6-difluoro-4-pentylbenzylidene)hydrazine
1-(3,4,5-trifluorobenzylidene)-2-(2,6-difluoro-4-heptylbenzylidene)hydrazine
1-(3,4,5-trifluorobenzylidene)-2-(2,6-difluoro-4-methoxybenzylidene)hydrazine
1-(4-trifluoromethoxybenzylidene)-2-(2-fluoro-4-methylbenzylidene)hydrazine
1-(4-trifluoromethoxybenzylidene)-2-(2-fluoro-4-ethylbenzylidene)hydrazine
1-(4-trifluoromethoxybenzylidene)-2-(2-fluoro-4-propylbenzylidene)hydrazine
1-(4-trifluoromethoxybenzylidene)-2-(2-fluoro-4-butylbenzylidene)hydrazine
1-(4-trifluoromethoxybenzylidene)-2-(2-fluoro-4-pentylbenzylidene)hydrazine
1-(4-trifluoromethoxybenzylidene)-2-(2-fluoro-4-heptylbenzylidene)hydrazine
1-(4-trifluoromethoxybenzylidene)-2-(2-fluoro-4-methoxybenzylidene)hydrazine
1-(4-trifluoromethoxybenzylidene)-2-(2,6-difluoro-4-methylbenzylidene)hydrazine
1-(4-trifluoromethoxybenzylidene)-2-(2,6-difluoro-4-ethylbenzylidene)hydrazine
1-(4-trifluoromethoxybenzylidene)-2-(2,6-difluoro-4-propylbenzylidene)hydrazine
1-(4-trifluoromethoxybenzylidene)-2-(2,6-difluoro-4-butylbenzylidene)hydrazine
1-(4-trifluoromethoxybenzylidene)-2-(2,6-difluoro-4-pentylbenzylidene)hydrazine
1-(4-trifluoromethoxybenzylidene)-2-(2,6-difluoro-4-heptylbenzylidene)hydrazine
1-(4-trifluoromethoxybenzylidene)-2-(2,6-difluoro-4-methoxybenzylidene )hydrazine
1-(4-cyanobenzylidene)-2-(2-fluoro-4-methylbenzylidene)hydrazine
1-(4-cyanobenzylidene)-2-(2-fluoro-4-ethylbenzylidene)hydrazine
1-(4-cyanobenzylidene)-2-(2-fluoro-4-propylbenzylidene)hydrazine
1-(4-cyanobenzylidene)-2-(2-fluoro-4-butylbenzylidene)hydrazine
1-(4-cyanobenzylidene)-2-(2-fluoro-4-pentylbenzylidene)hydrazine
1-(4-cyanobenzylidene)-2-(2-fluoro-4-heptylbenzylidene)hydrazine
1-(4-cyanobenzylidene)-2-(2-fluoro-4-methoxybenzylidene)hydrazine
1-(4-cyanobenzylidene)-2-(2,6-difluoro-4-methylbenzylidene)hydrazine
1-(4-cyanobenzylidene)-2-(2,6-difluoro-4-ethylbenzylidene)hydrazine
1-(4-cyanobenzylidene)-2-(2,6-difluoro-4-propylbenzylidene)hydrazine
1-(4-cyanobenzylidene)-2-(2,6-difluoro-4-butylbenzylidene)hydrazine
1-(4-cyanobenzylidene)-2-(2,6-difluoro-4-pentylbenzylidene)hydrazine
1-(4-cyanobenzylidene)-2-(2,6-difluoro-4-heptylbenzylidene)hydrazine
1-(4-cyanobenzylidene)-2-(2,6-difluoro-4-methoxybenzylidene)hydrazine
1-(4-trifluoromethylbenzylidene)-2-(2-fluoro-4-methylbenzylidene)hydrazine
1-(4-trifluoromethylbenzylidene)-2-(2-fluoro-4-ethylbenzylidene)hydrazine
1-(4-trifluoromethylbenzylidene)-2-(2-fluoro-4-propylbenzylidene)hydrazine
1-(4-trifluoromethylbenzylidene)-2-(2-fluoro-4-butylbenzylidene)hydrazine
1-(4-trifluoromethylbenzylidene)-2-(2-fluoro-4-pentylbenzylidene)hydrazine
1-(4-trifluoromethylbenzylidene)-2-(2-fluoro-4-heptylbenzylidene)hydrazine
1-(4-trifluoromethylbenzylidene)-2-(2-fluoro-4-methoxybenzylidene)hydrazine
1-(4-trifluoromethylbenzylidene)-2-(2,6-difluoro-4-methylbenzylidene)hydrazine
1-(4-trifluoromethylbenzylidene)-2-(2,6-difluoro-4-ethylbenzylidene)hydrazine
1-(4-trifluoromethylbenzylidene)-2-(2,6-difluoro-4-propylbenzylidene)hydrazine
1-(4-trifluoromethylbenzylidene)-2-(2,6-difluoro-4-butylbenzylidene)hydrazine
1-(4-trifluoromethylbenzylidene)-2-(2,6-difluoro-4-pentylbenzylidene)hydrazine
1-(4-trifluoromethylbenzylidene)-2-(2,6-difluoro-4-heptylbenzylidene)hydrazine
1-(4-trifluoromethylbenzylidene)-2-(2,6-difluoro-4-methoxybenzylidene)hydrazine
1-(4-chlorobenzylidene)-2-(2-fluoro-4-methylbenzylidene)hydrazine
1-(4-chlorobenzylidene)-2-(2-fluoro-4-ethylbenzylidene)hydrazine
1-(4-chlorobenzylidene)-2-(2-fluoro-4-propylbenzylidene)hydrazine
1-(4-chlorobenzylidene)-2-(2-fluoro-4-butylbenzylidene)hydrazine
1-(4-chlorobenzylidene)-2-(2-fluoro-4-pentylbenzylidene)hydrazine
1-(4-chlorobenzylidene)-2-(2-fluoro-4-heptylbenzylidene)hydrazine
1-(4-chlorobenzylidene)-2-(2-fluoro-4-methoxybenzylidene)hydrazine
1-(4-chlorobenzylidene)-2-(2,6-difluoro-4-methylbenzylidene)hydrazine
1-(4-chlorobenzylidene)-2-(2,6-difluoro-4-ethylbenzylidene)hydrazine
1-(4-chlorobenzylidene)-2-(2,6-difluoro-4-propylbenzylidene)hydrazine
1-(4-chlorobenzylidene)-2-(2,6-difluoro-4-butylbenzylidene)hydrazine 1-(4-chlorobenzylidene)-2-(2,6-difluoro-4-pentylbenzylidene)hydrazine
1-(4-chlorobenzylidene)-2-(2,6-difluoro-4-heptylbenzylidene)hydrazine
1-(4-chlorobenzylidene)-2-(2,6-difluoro-4-methoxybenzylidene)hydrazine
1-(4-methoxybenzylidene)-2-(2-fluoro-4-methylbenzylidene)hydrazine
1-(4-methoxybenzylidene)-2-(2-fluoro-4-ethylbenzylidene)hydrazine
1-(4-methoxybenzylidene)-2-(2-fluoro-4-propylbenzylidene)hydrazine
1-(4-methoxybenzylidene)-2-(2-fluoro-4-butylbenzylidene)hydrazine
1-(4-methoxybenzylidene)-2-(2-fluoro-4-pentylbenzylidene)hydrazine
1-(4-methoxybenzylidene)-2-(2-fluoro-4-heptylbenzylidene)hydrazine
1-(4-methoxybenzylidene)-2-(2-fluoro-4-methoxybenzylidene)hydrazine
1-(4-methoxybenzylidene)-2-(2,6-difluoro-4-methylbenzylidene)hydrazine
1-(4-methoxybenzylidene)-2-(2,6-difluoro-4-ethylbenzylidene)hydrazine
1-(4-methoxybenzylidene)-2-(2,6-difluoro-4-propylbenzylidene)hydrazine
1-(4-methoxybenzylidene)-2-(2,6-difluoro-4-butylbenzylidene)hydrazine
1-(4-methoxybenzylidene)-2-(2,6-difluoro-4-pentylbenzylidene)hydrazine
1-(4-methoxybenzylidene)-2-(2,6-difluoro-4-heptylbenzylidene)hydrazine
1-(4-methoxybenzylidene)-2-(2,6-difluoro-4-methoxybenzylidene)hydrazine
1-(4-methylbenzylidene)-2-(2-fluoro-4-methylbenzylidene)hydrazine
1-(4-methylbenzylidene)-2-(2-fluoro-4-ethylbenzylidene)hydrazine
1-(4-methylbenzylidene)-2-(2-fluoro-4-propylbenzylidene)hydrazine
1-(4-methylbenzylidene)-2-(2-fluoro-4-butylbenzylidene)hydrazine
1-(4-methylbenzylidene)-2-(2-fluoro-4-pentylbenzylidene)hydrazine
1-(4-methylbenzylidene)-2-(2-fluoro-4-heptylbenzylidene)hydrazine
1-(4-methylbenzylidene)-2-(2-fluoro-4-methoxybenzylidene)hydrazine
1-(4-methylbenzylidene)-2-(2,6-difluoro-4-methylbenzylidene)hydrazine
1-(4-methylbenzylidene)-2-(2,6-difluoro-4-ethylbenzylidene)hydrazine
1-(4-methylbenzylidene)-2-(2,6-difluoro-4-propylbenzylidene)hydrazine
1-(4-methylbenzylidene)-2-(2,6-difluoro-4-butylbenzylidene)hydrazine
1-(4-methylbenzylidene)-2-(2,6-difluoro-4-pentylbenzylidene)hydrazine
1-(4-methylbenzylidene)-2-(2,6-difluoro-4-heptylbenzylidene)hydrazine
1-(4-methylbenzylidene)-2-(2,6-difluoro-4-methoxybenzylidene)hydrazine
1-(4-ethylbenzylidene)-2-(2-fluoro-4-methylbenzylidene)hydrazine
1-(4-ethylbenzylidene)-2-(2-fluoro-4-ethylbenzylidene)hydrazine
1-(4-ethylbenzylidene)-2-(2-fluoro-4-propylbenzylidene)hydrazine
1-(4-ethylbenzylidene)-2-(2-fluoro-4-butylbenzylidene)hydrazine
1-(4-ethylbenzylidene)-2-(2-fluoro-4-pentylbenzylidene)hydrazine
1-(4-ethylbenzylidene)-2-(2-fluoro-4-heptylbenzylidene)hydrazine
1-(4-ethylbenzylidene)-2-(2-fluoro-4-methoxybenzylidene)hydrazine
1-(4-ethylbenzylidene)-2-(2,6-difluoro-4-methylbenzylidene)hydrazine
1-(4-ethylbenzylidene)-2-(2,6-difluoro-4-ethylbenzylidene)hydrazine
1-(4-ethylbenzylidene)-2-(2,6-difluoro-4-propylbenzylidene)hydrazine
1-(4-ethylbenzylidene)-2-(2,6-difluoro-4-butylbenzylidene)hydrazine
1-(4-ethylbenzylidene)-2-(2,6-difluoro-4-pentylbenzylidene)hydrazine
1-(4-ethylbenzylidene)-2-(2,6-difluoro-4-heptylbenzylidene)hydrazine
1-(4-ethylbenzylidene)-2-(2,6-difluoro-4-methoxybenzylidene)hydrazine
1-(4-propylbenzylidene)-2-(2-fluoro-4-methylbenzylidene)hydrazine
1-(4-propylbenzylidene)-2-(2-fluoro-4-ethylbenzylidene)hydrazine
1-(4-propylbenzylidene)-2-(2-fluoro-4-propylbenzylidene)hydrazine
1-(4-propylbenzylidene)-2-(2-fluoro-4-butylbenzylidene)hydrazine
1-(4-propylbenzylidene)-2-(2-fluoro-4-pentylbenzylidene)hydrazine
1-(4-propylbenzylidene)-2-(2-fluoro-4-heptylbenzylidene)hydrazine
1-(4-propylbenzylidene)-2-(2-fluoro-4-methoxybenzylidene)hydrazine
1-(4-propylbenzylidene)-2-(2,6-difluoro-4-methylbenzylidene)hydrazine
1-(4-propylbenzylidene)-2-(2,6-difluoro-4-ethylbenzylidene)hydrazine
1-(4-propylbenzylidene)-2-(2,6-difluoro-4-propylbenzylidene)hydrazine
1-(4-propylbenzylidene)-2-(2,6-difluoro-4-butylbenzylidene)hydrazine
1-(4-propylbenzylidene)-2-(2,6-difluoro-4-pentylbenzylidene)hydrazine
1-(4-propylbenzylidene)-2-(2,6-difluoro-4-heptylbenzylidene)hydrazine
1-(4-propylbenzylidene)-2-(2,6-difluoro-4-methoxybenzylidene)hydrazine

EXAMPLE 6

Preparation of Liquid Crystal Composition (2)

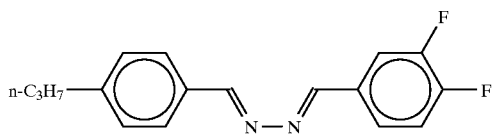

A composition (M-7) consisting of 80% of the host liquid crystal (H) and 20% of Compound No. 7 obtained in Example 4 was prepared. The composition thus prepared exhibited an upper nematic phase temperature limit (TN-1) of 98° C., which is a drop of about 20° C. from that of the host liquid crystal (H). This composition was then allowed to stand at a temperature of 0° C. for 24 hours. As a result, no crystallization was observed. This liquid crystal composition was allowed to stand at a temperature of −20° C. for a prolonged period of time so that it was solidified. While being heated, this liquid crystal composition was measured for temperature at which it again turns to uniform nematic phase ($T_{-N}$). The results were 9° C. A liquid crystal device was then prepared from this composition in the same manner as mentioned above. The liquid crystal device thus prepared was then measured for switching time. The results were 14.3 msec., which demonstrates that the response is very fast. The liquid crystal device was then measured for threshold voltage. The results were 1.83 V, which is a slight drop from that of the host liquid crystal (H).

EXAMPLE 7

Preparation of Liquid Crystal Composition (3)

A liquid crystal composition (M-8) consisting of 80% of the host liquid crystal (H) and 20% of Compound No. 8:

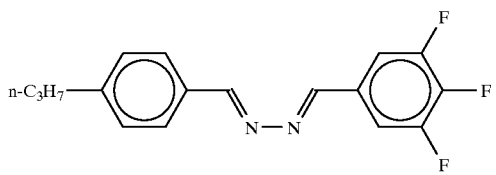

obtained in Example 5 was prepared. The liquid crystal composition (M-8) thus prepared exhibited an upper nematic phase temperature limit ($T_{N-I}$) of 91.2° C., which is a drop from that of the liquid crystal composition (M-7). The liquid crystal composition (M-8) was then allowed to stand at a temperature of 0° C. for 24 hours or longer. No crystallization was observed. The liquid crystal composition (M-8) was then solidified in the same manner as (M-7). The liquid crystal composition was then measured for $T_{-N}$. The results were 13° C.

A liquid crystal device was then prepared from this liquid crystal composition in the same manner as mentioned above. The liquid crystal device thus prepared was then measured for switching time. The results were 17.8 msec., which demonstrates that the response rate is very fast, though inferior to that of the liquid crystal composition (M-7). The liquid crystal device was then measured for threshold voltage. The results were 1.54 V, which is a decrease as great as not less than 0.3 V from that of the host liquid crystal (H).

EXAMPLE 8

Synthesis of 1-[4-(3-butenyl)benzylidene]-2-(4-methylbenzylidene)hydrazine (Compound No. 9 set forth in Table 1)

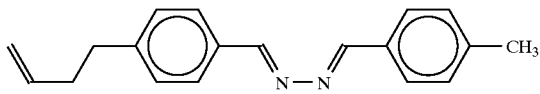

To 15.6 g of a monohydrate of hydrazine was added a solution of 5.0 g of 4-(3-butenyl)benzaldehyde (synthesized by reacting 1-(3-butenyl)-4-bromobenzene with magnesium to prepare a Grignard reagent which is then reacted with DMF) in 20 ml of ethanol. The mixture was stirred at room temperature for 30 minutes. To the mixture was then added 20 ml of saturated aqueous solution of sodium bicarbonate. To the mixture was then added 10 ml of dichloromethane. The mixture was then washed with 10 ml of saturated aqueous solution of sodium bicarbonate twice. To the resulting organic phase was then added 3.5 ml of triethylamine. The mixture was then dehydrated and dried over anhydrous sodium sulfate. The solvent was then distilled off under reduced pressure. To the residue was then added 3.5 ml of triethylamine. To the mixture were then added 20 ml of ethanol and 3.75 g of 4-methylbenzaldehyde. The mixture was then stirred at room temperature for 3 hours. To the mixture was then added 20 ml of saturated aqueous solution of sodium bicarbonate. To the mixture was then added 10 ml of dichloromethane. The mixture was then washed with 10 ml of saturated aqueous solution of sodium bicarbonate. The solvent was then distilled off under reduced pressure. The residue was purified through alumina (basic) column chromatography (dichloromethane), and then recrystallized from methanol to obtain 7.0 g of 1-[4-(3-butenyl)benzylidene]-2-(4-methylbenzylidene)hydrazine. The compound thus obtained had a melting point of 82° C. and exhibited nematic phase up to 103° C.

The foregoing procedure was followed except that 4-ethylbenzaldehyde, 4-propylbenzaldehyde, 4-butylbenzaldehyde, 4-pentylbenzaldehyde, 4-heptylbenzaldehyde, 2,4-dimethylbenzaldehyde, 4-methoxybenzaldehyde, 2,3-difluoro-4-ethoxybenzaldehyde, 4-fluorobenzaldehyde, 3,4-difluorobenzaldehyde, 3,4,5-trifluorobenzaldehyde, 4-chlorobenzaldehyde, 4-trifluoromethoxybenzaldehyde or 4-cyanobenzaldehyde was used instead of 4-methylbenzaldehyde. As a result, the following compounds were obtained:

1-[4-(3-butenyl)benzylidene]-2-(4-ethylbenzylidene) hydrazine
1-[4-(3-butenyl)benzylidene]-2-(4-propylbenzylidene) hydrazine
1-[4-(3-butenyl)benzylidene]-2-(4-butylbenzylidene) hydrazine
1-[4-(3-butenyl)benzylidene]-2-(4-pentylbenzylidene) hydrazine
1-[4-(3-butenyl)benzylidene]-2-(4-heptylbenzylidene) hydrazine
1-[4-(3-butenyl)benzylidene]-2-(2,4-dimethylbenzylidene) hydrazine
1-[4-(3-butenyl)benzylidene]-2-(4-methoxybenzylidene) hydrazine
1-[4-(3-butenyl)benzylidene]-2-(2,3-difluoro-4-ethoxybenzylidene)hydrazine
1-[4-(3-butenyl)benzylidene]-2-(4-fluorobenzylidene) hydrazine
1-[4-(3-butenyl)benzylidene]-2-(3,4-difluorobenzylidene) hydrazine
1-[4-(3-butenyl)benzylidene]-2-(3,4,5-trifluorobenzylidene) hydrazine
1-[4-(3-butenyl)benzylidene]-2-(4-chlorobenzylidene) hydrazine
1-[4-(3-butenyl)benzylidene]-2-(4-trifluoromethoxybenzylidene)hydrazine
1-[4-(3-butenyl)benzylidene]-2-(4-cyanobenzylidene) hydrazine Further, the foregoing procedure was followed except that 4-(trans-3-pentenyl)benzaldehyde, 4-(4-pentenyl) benzaldehyde, 4-(trans-3-hexenyl)benzaldehyde, 4-(5-hexenyl) benzaldehyde, 4-allyloxybenzaldehyde or 4-allylbenzaldehyde was used instead of 4-(3-butenyl) benzaldehyde. As a result, the following compounds were obtained:

1-[4-(trans-3-pentenyl)benzylidene]-2-(4-methylbenzylidene)hydrazine
1-[4-(trans-3-pentenyl)benzylidene]-2-(4-ethylbenzylidene)hydrazine
1-[4-(trans-3-pentenyl)benzylidene]-2-(4-propylbenzylidene)hydrazine
1-[4-(trans-3-pentenyl)benzylidene]-2-(4-butylbenzylidene)hydrazine
1-[4-(trans-3-pentenyl)benzylidene]-2-(4-pentylbenzylidene)hydrazine
1-[4-(trans-3-pentenyl)benzylidene]-2-(4-heptylbenzylidene)hydrazine
1-[4-(trans-3-pentenyl)benzylidene]-2-(2,4-dimethylbenzylidene)hydrazine
1-[4-(trans-3-pentenyl)benzylidene]-2-(4-methoxybenzylidene)hydrazine
1-[4-(trans-3-pentenyl)benzylidene]-2-(2,3-difluoro-4-ethoxybenzylidene)hydrazine
1-[4-(trans-3-pentenyl)benzylidene]-2-(4-fluorobenzylidene)hydrazine
1-[4-(trans-3-pentenyl)benzylidene]-2-(3,4-difluorobenzylidene)hydrazine
1-[4-(trans-3-pentenyl)benzylidene]-2-(3,4,5-trifluorobenzylidene)hydrazine
1-[4-(trans-3-pentenyl)benzylidene]-2-(4-chlorobenzylidene)hydrazine
1-[4-(trans-3-pentenyl)benzylidene]-2-(4-trifluoromethoxybenzylidene)hydrazine
1-[4-(trans-3-pentenyl)benzylidene]-2-(4-cyanobenzylidene)hydrazine
1-[4-(4-pentenyl)benzylidene]-2-(4-methylbenzylidene)hydrazine
1-[4-(4-pentenyl)benzylidene]-2-(4-ethylbenzylidene)hydrazine
1-[4-(4-pentenyl)benzylidene]-2-(4-propylbenzylidene)hydrazine
1-[4-(4-pentenyl)benzylidene]-2-(4-butylbenzylidene)hydrazine
1-[4-(4-pentenyl)benzylidene]-2-(4-pentylbenzylidene)hydrazine
1-[4-(4-pentenyl)benzylidene]-2-(4-heptylbenzylidene)hydrazine
1-[4-(4-pentenyl)benzylidene]-2-(2,4-dimethylbenzylidene)hydrazine
1-[4-(4-pentenyl)benzylidene]-2-(4-methoxybenzylidene)hydrazine
1-[4-(4-pentenyl)benzylidene]-2-(2,3-difluoro-4-ethoxybenzylidene)hydrazine
1-[4-(4-pentenyl)benzylidene]-2-(4-fluorobenzylidene)hydrazine
1-[4-(4-pentenyl)benzylidene]-2-(3,4-difluorobenzylidene)hydrazine
1-[4-(4-pentenyl)benzylidene]-2-(3,4,5-trifluorobenzylidene)hydrazine
1-[4-(4-pentenyl)benzylidene]-2-(4-chlorobenzylidene)hydrazine
1-[4-(4-pentenyl)benzylidene]-2-(4-trifluoromethoxybenzylidene)hydrazine
1-[4-(4-pentenyl)benzylidene]-2-(4-cyanobenzylidene)hydrazine
1-[4-(trans-3-hexenyl)benzylidene]-2-(4-methylbenzylidene)hydrazine
1-[4-(trans-3-hexenyl)benzylidene]-2-(4-ethylbenzylidene)hydrazine
1-[4-(trans-3-hexenyl)benzylidene]-2-(4-propylbenzylidene)hydrazine
1-[4-(trans-3-hexenyl)benzylidene]-2-(4-butylbenzylidene)hydrazine
1-[4-(trans-3-hexenyl)benzylidene]-2-(4-pentylbenzylidene)hydrazine
1-[4-(trans-3-hexenyl)benzylidene]-2-(4-heptylbenzylidene)hydrazine
1-[4-(trans-3-hexenyl)benzylidene]-2-(2,4-dimethylbenzylidene)hydrazine
1-[4-(trans-3-hexenyl)benzylidene]-2-(4-methoxybenzylidene)hydrazine
1-[4-(trans-3-hexenyl)benzylidene]-2-(2,3-difluoro-4-ethoxybenzylidene)hydrazine
1-[4-(trans-3-hexenyl)benzylidene]-2-(4-fluorobenzylidene)hydrazine
1-[4-(trans-3-hexenyl)benzylidene]-2-(3,4-difluorobenzylidene)hydrazine
1-[4-(trans-3-hexenyl)benzylidene]-2-(3,4,5-trifluorobenzylidene)hydrazine
1-[4-(trans-3-hexenyl)benzylidene]-2-(4-chlorobenzylidene)hydrazine
1-[4-(trans-3-hexenyl)benzylidene]-2-(4-trifluoromethoxybenzylidene)hydrazine
1-[4-(trans-3-hexenyl)benzylidene]-2-(4-cyanobenzylidene)hydrazine
1-[4-(5-hexenyl)benzylidene]-2-(4-2ethylbenzylidene)hydrazine
1-[4-(5-hexenyl)benzylidene]-2-(4-ethylbenzylidene)hydrazine
1-[4-(5-hexenyl)benzylidene]-2-(4-propylbenzylidene)hydrazine
1-[4-(5-hexenyl)benzylidene]-2-(4-butylbenzylidene)hydrazine
1-[4-(5-hexenyl)benzylidene]-2-(4-pentylbenzylidene)hydrazine
1-[4-(5-hexenyl)benzylidene]-2-(4-heptylbenzylidene)hydrazine
1-[4-(5-hexenyl)benzylidene]-2-(2,4-dimethylbenzylidene)hydrazine
1-[4-(5-hexenyl)benzylidene]-2-(4-methoxybenzylidene)hydrazine
1-[4-(5-hexenyl)benzylidene]-2-(2,3-difluoro-4-ethoxybenzylidene)hydrazine
1-[4-(5-hexenyl)benzylidene]-2-(4-fluorobenzylidene)hydrazine
1-[4-(5-hexenyl)benzylidene]-2-(3,4-difluorobenzylidene)hydrazine
1-[4-(5-hexenyl)benzylidene]-2-(3,4,5-trifluorobenzylidene)hydrazine
1-[4-(5-hexenyl)benzylidene]-2-(4-chlorobenzylidene)hydrazine
1-[4-(5-hexenyl)benzylidene]-2-(4-trifluoromethoxybenzylidene)hydrazine
1-[4-(5-hexenyl)benzylidene]-2-(4-cyanobenzylidene)hydrazine
1-[4-allyloxybenzylidene]-2-(4-methylbenzylidene)hydrazine
1-[4-allyloxybenzylidene]-2-(4-ethylbenzylidene)hydrazine
1-[4-allyloxybenzylidene]-2-(4-propylbenzylidene)hydrazine
1-[4-allyloxybenzylidene]-2-(4-butylbenzylidene)hydrazine
1-[4-allyloxybenzylidene]-2-(4-pentylbenzylidene)hydrazine
1-[4-allyloxybenzylidene]-2-(4-heptylbenzylidene)hydrazine
1-[4-allyloxybenzylidene]-2-(2,4-dimethylbenzylidene)hydrazine
1-[4-allyloxybenzylidene]-2-(4-methoxybenzylidene)hydrazine
1-[4-allyloxybenzylidene]-2-(2,3-difluoro-4-ethoxybenzylidene)hydrazine 1-[4-allyloxybenzylidene]-2-(4-fluorobenzylidene)hydrazine
1-[4-allyloxybenzylidene]-2-(3,4-difluorobenzylidene)hydrazine
1-[4-allyloxybenzylidene]-2-(3,4,5-trifluorobenzylidene)hydrazine
1-[4-allyloxybenzylidene]-2-(4-chlorobenzylidene)hydrazine
1-[4-allyloxybenzylidene]-2-(4-trifluoromethoxybenzylidene)hydrazine
1-[4-allyloxybenzylidene]-2-(4-cyanobenzylidene)hydrazine
1-[4-allylbenzylidene]-2-(4-methylbenzylidene)hydrazine
1-[4-allylbenzylidene]-2-(4-ethylbenzylidene)hydrazine
1-[4-allylbenzylidene]-2-(4-propylbenzylidene)hydrazine
1-[4-allylbenzylidene]-2-(4-butylbenzylidene)hydrazine
1-[4-allylbenzylidene]-2-(4-pentylbenzylidene)hydrazine
1-[4-allylbenzylidene]-2-(4-heptylbenzylidene)hydrazine
1-[4-allylbenzylidene]-2-(2,4-dimethylbenzylidene)hydrazine
1-[4-allylbenzylidene]-2-(4-methoxybenzylidene)hydrazine
1-[4-allylbenzylidene]-2-(2,3-difluoro-4-ethoxybenzylidene)hydrazine
1-[4-allylbenzylidene]-2-(4-fluorobenzylidene)hydrazine
1-[4-allylbenzylidene]-2-(3,4-difluorobenzylidene)hydrazine
1-[4-allylbenzylidene]-2-(3,4,5-trifluorobenzylidene)hydrazine
1-[4-allylbenzylidene]-2-(4-chlorobenzylidene)hydrazine
1-[4-allylbenzylidene]-2-(4-trifluoromethoxybenzylidene)hydrazine
1-[4-allylbenzylidene]-2-(4-cyanobenzylidene)hydrazine

EXAMPLE 9

Synthesis of 1,2-bis[4-(3-butenyl)benzylidene]hydrazine (Compound No. 10 set forth in Table 1)

(I-2)

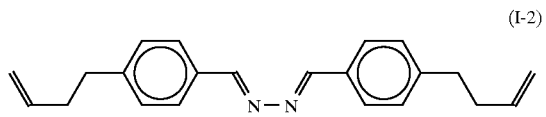

8.4 g of a monohydrate of hydrazine and 45 g of 4-(3-butenyl)benzaldehyde were dissolved in 80 ml of methanol. The mixture was stirred at room temperature for 2 hours. To the mixture was then added 150 ml of dichloromethane. The mixture was then washed with saturated aqueous solution of sodium bicarbonate twice. The mixture was then dehydrated and dried over anhydrous sodium sulfate. The solvent was then distilled off under reduced pressure. The resulting crude reaction product was purified through basic alumina column chromatography, and then recrystallized from methanol to obtain 42 g of 1,2-bis[4-(3-butenyl)benzylidene]hydrazine. The compound thus obtained had a melting point of 57° C. and exhibited nematic phase up to 116° C.

The following compounds were obtained in the same manner as mentioned above.

1,2-Bis[4-(trans-3-pentenyl)benzylidene]hydrazine
1,2-Bis[4-(4-pentenyl)benzylidene]hydrazine
1,2-Bis[4-(trans-3-hexenyl)benzylidene]hydrazine
1,2-Bis[4-(5-hexenyl)benzylidene]hydrazine
1,2-Bis(4-allyloxybenzylidene)hydrazine
1,2-Bis(4-allylbenzylidene)hydrazine

EXAMPLE 10

Preparation of Liquid Crystal Composition (4)

The host liquid crystal (H) was then packed into a 6.0 μm thick TN cell to prepare a liquid crystal device. The liquid crystal device thus prepared was then measured for switching time. The results were 32.5 msec. (Under the application of voltage when the decay time and the rise time are equal), the liquid crystal device exhibited a threshold voltage of 2.14 V.

A liquid crystal composition (M-9) consisting of 80% of the host liquid crystal (H) and 20% of Compound No. 9:

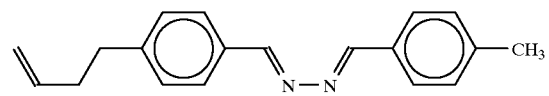

obtained in Example 8 was prepared. The liquid crystal composition (M-9) exhibited an upper nematic phase temperature limit ($T_{N-1}$) of 118° C., which is a slight increase from that of the host liquid crystal (H). The liquid crystal composition was then allowed to stand at a temperature of 0° C. for 24 hours. As a result, no crystallization was observed. This liquid crystal composition was allowed to stand at a temperature of −20° C. for a prolonged period of time so that it was solidified. While being heated, this liquid crystal composition was measured for temperature at which it again turns to uniform nematic phase ($T_{-N}$). The results were as low as −12° C. A liquid crystal device was then prepared from this composition in the same manner as in the host liquid crystal (H). The liquid crystal device thus prepared was then measured for switching time. The results were 30.1 msec., which demonstrates that the response is fast. The liquid crystal device was then measured for threshold voltage. The results were 2.69 V.

Accordingly, the incorporation of Compound No. 9 makes it possible to extend the nematic phase temperature range of the host liquid crystal as well as shorten the switching time of the host liquid crystal.

EXAMPLE 11

Preparation of Liquid Crystal Composition (5)

A liquid crystal composition (M-10) consisting of 80% of the host liquid crystal (H) and the same amount (20%) of Compound No. 10 obtained in Example 9 as mentioned above was prepared. This liquid crystal composition (M-10) exhibited an upper nematic phase temperature limit ($T_{N-1}$) of 119° C., which is an increase from that of the liquid crystal composition (M-9). This liquid crystal composition was allowed to stand at a temperature of 0° C. for 24 hours. As a result, no crystallization was observed. This liquid crystal composition was then solidified in the same manner as (M-9). This liquid crystal composition was then measured for $T_{-N}$. The results were 5° C.

A liquid crystal device was then prepared from this composition in the same manner as mentioned above. The liquid crystal device thus prepared was then measured for switching time. The results were 29.7 msec., which demonstrates that the response is fast. The liquid crystal device was then measured for threshold voltage. The results were 2.67 V.

EXAMPLE 12

Synthesis of 1-(4-ethylbenzylidene)-2-[4-(trans-4-propyl)cyclohexylbenzylidene]hydrazine (Compound No. 13 set forth in Table 1)

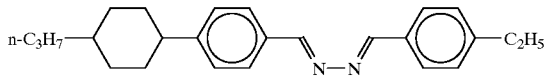

To 242 g of a monohydrate of hydrazine was added a solution of 65 g of 4-ethylbenzaldehyde in 300 ml of dichloromethane. The mixture was then stirred at room temperature for 1 hour. The mixture was then washed with 300 ml of saturated aqueous solution of sodium bicarbonate twice to remove excess hydrazine. To the resulting organic phase was then added 40 ml of triethylamine. The mixture was then dehydrated and dried over anhydrous sodium sulfate. Sodium sulfate was then removed by filtration. The resulting filtrate was then added dropwise to 300 ml of dichloromethane and 121 g of 4-(trans-4-propyl) cyclohexylbenzaldehyde in the presence of 240 g of basic alumina. The mixture was then stirred at room temperature for 3 hours. The reaction solution was directly purified through alumina (basic) column chromatography (dichloromethane), and then recrystallized from ethanol to obtain 44 g of 1-(4-ethylbenzylidene)-2-[4-(trans-4-propyl)cyclohexylbenzylidene]hydrazine. The compound thus obtained had a melting point of 97° C. and exhibited nematic phase up to 227° C.

The foregoing procedure was followed except that 4-methylbenzaldehyde, 4-propylbenzaldehyde, 4-butylbenzaldehyde, 4-pentylbenzaldehyde, 4-heptylbenzaldehyde, 4-(3-butenyl)benzaldehyde, 4-(4-pentenyl)benzaldehyde, 4-(5-hexenyl)benzaldehyde or 4-(6-heptenyl)benzaldehyde instead of 4-ethylbenzaldehyde. As a result, the following compounds were obtained:

1-(4-methylbenzylidene)-2-[4-(trans-4-propyl)cyclohexylbenzylidene]hydrazine(I-1)
1-(4-propylbenzylidene)-2-[4-(trans-4-propyl)cyclohexylbenzylidene]hydrazine(I-3)
1-(4-butylbenzylidene)-2-[4-(trans-4-propyl)cyclohexylbenzylidene]hydrazine
1-(4-pentylbenzylidene)-2-[4-(trans-4-propyl)cyclohexylbenzylidene]hydrazine
1-(4-heptylbenzylidene)-2-[4-(trans-4-propyl)cyclohexylbenzylidene]hydrazine
1-(4-hexylbenzylidene)-2-[4-(trans-4-propyl)cyclohexylbenzylidene]hydrazine
1-[4-(3-butenyl)benzylidene]-2-[4-(trans-4-propyl)cyclohexylbenzylidene]hydrazine
1-[4-(4-pentenyl)benzylidene]-2-[4-(trans-4-propyl)cyclohexylbenzylidene]hydrazine
1-[4-(5-hexenyl)benzylidene]-2-[4-(trans-4-propyl)cyclohexylbenzylidene]hydrazine
1-[4-(6-heptenyl)benzylidene]-2-[4-(trans-4-propyl)cyclohexylbenzylidene]hydrazine Further, the foregoing procedure was followed except that 4-(trans-4-methyl)cyclohexylbenzaldehyde, 4-(trans-4-ethyl)cyclohexylbenzaldehyde, 4-(trans-4-butyl)cyclohexylbenzaldehyde, 4-(trans-5-hexyl)cyclohexylbenzaldehyde or 4-(trans-6-heptyl)cyclohexylbenzaldehyde instead of 4-(trans-4-propyl)cyclohexylbenzaldehyde. As a result, the following compounds were obtained:

1-(4-methylbenzylidene)-2-[4-(trans-4-methyl)cyclohexylbenzylidene]hydrazine
1-(4-ethylbenzylidene)-2-[4-(trans-4-methyl)cyclohexylbenzylidene]hydrazine
1-(4-propylbenzylidene)-2-[4- (trans-4-methyl)cyclohexylbenzylidene]hydrazine
1-(4-butylbenzylidene)-2-[4-(trans-4-methyl)cyclohexylbenzylidene]hydrazine
1-(4-pentylbenzylidene)-2-[4-(trans-4-methyl)cyclohexylbenzylidene]hydrazine
1-(4-hexylbenzylidene)-2-[4-(trans-4-methyl)cyclohexylbenzylidene]hydrazine
1-(4-heptylbenzylidene)-2-[4-(trans-4-methyl)cyclohexylbenzylidene]hydrazine
1-[4-(3-butenyl)benzylidene]-2-[4-(trans-4-methyl)cyclohexylbenzylidene]hydrazine
1-[4-(4-pentenyl)benzylidene]-2-[4-(trans-4-methyl)cyclohexylbenzylidene]hydrazine
1-[4-(5-hexenyl)benzylidene]-2-[4-(trans-4-methyl)cyclohexylbenzylidene]hydrazine
1-[4-(6-heptenyl)benzylidene]-2-[4-(trans-4-methyl)cyclohexylbenzylidene]hydrazine
1-(4-methylbenzylidene)-2-[4-(trans-4-ethyl)cyclohexylbenzylidene]hydrazine
1-(4-ethylbenzylidene)-2-[4-(trans-4-ethyl)cyclohexylbenzylidene]hydrazine
1-(4-propylbenzylidene)-2-[4-(trans-4-ethyl)cyclohexylbenzylidene]hydrazine
1-(4-butylbenzylidene)-2-[4-(trans-4-ethyl)cyclohexylbenzylidene]hydrazine
1-(4-pentylbenzylidene)-2-[4-(trans-4-ethyl)cyclohexylbenzylidene]hydrazine
1-(4-hexylbenzylidene)-2-[4-(trans-4-ethyl)cyclohexylbenzylidene]hydrazine
1-(4-heptylbenzylidene)-2-[4-(trans-4-ethyl)cyclohexylbenzylidene]hydrazine
1-[4-(3-butenyl)benzylidene]-2-[4-(trans-4-ethyl)cyclohexylbenzylidene]hydrazine
1-[4-(4-pentenyl)benzylidene]-2-[4-(trans-4-ethyl)cyclohexylbenzylidene]hydrazine
1-[4-(5-hexenyl)benzylidene]-2-[4-(trans-4-ethyl)cyclohexylbenzylidene]hydrazine
1-[4-(6-heptenyl)benzylidene]-2-[4-(trans-4-ethyl)cyclohexylbenzylidene]hydrazine
1-(4-methylbenzylidene)-2-[4-(trans-4-butyl)cyclohexylbenzylidene]hydrazine
1-(4-ethylbenzylidene)-2-[4-(trans-4-butyl)cyclohexylbenzylidene]hydrazine
1-(4-propylbenzylidene)-2-[4-(trans-4-butyl)cyclohexylbenzylidene]hydrazine
1-(4-butylbenzylidene)-2-[4-(trans-4-butyl)cyclohexylbenzylidene]hydrazine
1-(4-pentylbenzylidene)-2-[4-(trans-4-butyl)cyclohexylbenzylidene]hydrazine
1-(4-hexylbenzylidene)-2-[4-(trans-4-butyl)cyclohexylbenzylidene]hydrazine
1-(4-heptylbenzylidene)-2-[4-(trans-4-butyl)cyclohexylbenzylidene]hydrazine
1-[4-(3-butenyl)benzylidene]-2-[4-(trans-4-butyl)cyclohexylbenzylidene]hydrazine
1-[4-(4-pentenyl)benzylidene]-2-[4-(trans-4-butyl)cyclohexylbenzylidene]hydrazine
1-[4-(5-hexenyl)benzylidene]-2-[4-(trans-4-butyl)cyclohexylbenzylidene]hydrazine
1-[4-(6-heptenyl)benzylidene]-2-[4-(trans-4-butyl)cyclohexylbenzylidene]hydrazine
1-(4-methylbenzylidene)-2-[4-(trans-4-pentyl)cyclohexylbenzylidene]hydrazine
1-(4-ethylbenzylidene)-2-[4-(trans-4-pentyl)cyclohexylbenzylidene]hydrazine 1-(4-propylbenzylidene)-2-[4-(trans-4-pentyl)cyclohexylbenzylidene]hydrazine
1-(4-butylbenzylidene)-2-[4-(trans-4-pentyl)cyclohexylbenzylidene]hydrazine
1-(4-pentylbenzylidene)-2-[4-(trans-4-pentyl)cyclohexylbenzylidene]hydrazine
1-(4-hexylbenzylidene)-2-[4-(trans-4-pentyl)cyclohexylbenzylidene]hydrazine
1-(4-heptylbenzylidene)-2-[4-(trans-4-pentyl)cyclohexylbenzylidene]hydrazine
1-[4-(3-butenyl)benzylidene]-2-[4-(trans-4-pentyl)cyclohexylbenzylidene]hydrazine
1-[4-(4-pentenyl)benzylidene]-2-[4-(trans-4-pentyl)cyclohexylbenzylidene]hydrazine
1-[4-(5-hexenyl)benzylidene]-2-[4-(trans-4-pentyl)cyclohexylbenzylidene]hydrazine
1-[4-(6-heptenyl)benzylidene]-2-[4-(trans-4-pentyl)cyclohexylbenzylidene]hydrazine
1-(4-methylbenzylidene)-2-[4-(trans-4-hexyl)cyclohexylbenzylidene]hydrazine
1-(4-ethylbenzylidene)-2-[4-(trans-4-hexyl)cyclohexylbenzylidene]hydrazine
1-(4-propylbenzylidene)-2-[4-(trans-4-hexyl)cyclohexylbenzylidene]hydrazine
1-(4-butylbenzylidene)-2-[4-(trans-4-hexyl)cyclohexylbenzylidene]hydrazine
1-(4-pentylbenzylidene)-2-[4-(trans-4-hexyl)cyclohexylbenzylidene]hydrazine
1-(4-hexylbenzylidene)-2-[4-(trans-4-hexyl)cyclohexylbenzylidene]hydrazine
1-(4-heptylbenzylidene)-2-[4-(trans-4-hexyl)cyclohexylbenzylidene]hydrazine
1-[4-(3-butenyl)benzylidene]-2-[4-(trans-4-hexyl)cyclohexylbenzylidene]hydrazine
1-[4-(4-pentenyl)benzylidene]-2-[4-(trans-4-hexyl)cyclohexylbenzylidene]hydrazine
1-[4-(5-hexenyl)benzylidene]-2-[4-(trans-4-hexyl)cyclohexylbenzylidene]hydrazine
1-[4-(6-heptenyl)benzylidene]-2-[4-(trans-4-hexyl)cyclohexylbenzylidene]hydrazine
1-(4-methylbenzylidene)-2-[4-(trans-4-heptyl)cyclohexylbenzylidene]hydrazine
1-(4-ethylbenzylidene)-2-[4-(trans-4-heptyl)cyclohexylbenzylidene]hydrazine
1-(4-propylbenzylidene)-2-[4-(trans-4-heptyl)cyclohexylbenzylidene]hydrazine
1-(4-butylbenzylidene)-2-[4-(trans-4-heptyl)cyclohexylbenzylidene]hydrazine
1-(4-pentylbenzylidene)-2-[4-(trans-4-heptyl)cyclohexylbenzylidene]hydrazine
1-(4-hexylbenzylidene)-2-[4-(trans-4-heptyl)cyclohexylbenzylidene]hydrazine
1-(4-heptylbenzylidene)-2-[4-(trans-4-heptyl)cyclohexylbenzylidene]hydrazine
1-[4-(3-butenyl)benzylidene]-2-[4-(trans-4-heptyl)cyclohexylbenzylidene]hydrazine
1-[4-(4-pentenyl)benzylidene]-2-[4-(trans-4-heptyl)cyclohexylbenzylidene]hydrazine
1-[4-(5-hexenyl)benzylidene]-2-[4-(trans-4-heptyl)cyclohexylbenzylidene]hydrazine
1-[4-(6-heptenyl)benzylidene]-2-[4-(trans-4-heptyl)cyclohexylbenzylidene]hydrazine

EXAMPLE 13

Synthesis of 1-(4-fluorobenzylidene)-2-[4-(trans-4-propyl)cyclohexylbenzylidene]hydrazine
(Compound No. 15 set forth in Table 1)

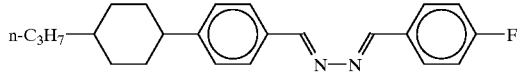

The procedure of Example 12 was followed except that 4-fluorobenzaldehyde was used instead of 4-ethylbenzaldehyde. As a result, 1-(4-fluorobenzylidene)-2-[4-(trans-4-propyl) cyclohexylbenzylidene]hydrazine was obtained. The phase transition temperature of this compound is set forth in Table 1.

Similarly, the following compounds were obtained:
1-(4-fluorobenzylidene)-2-[4-(trans-4-methyl)cyclohexylbenzylidene]hydrazine
1-(4-fluorobenzylidene)-2-[4-(trans-4-ethyl)cyclohexylbenzylidene]hydrazine
1-(4-fluorobenzylidene)-2-[4-(trans-4-butyl)cyclohexylbenzylidene]hydrazine
1-(4-fluorobenzylidene)-2-[4-(trans-4-pentyl)cyclohexylbenzylidene]hydrazine
1-(4-fluorobenzylidene)-2-[4-(trans-4-hexyl)cyclohexylbenzylidene]hydrazine
1-(4-fluorobenzylidene)-2-[4-(trans-4-heptyl)cyclohexylbenzylidene]hydrazine
1-(3,4-difluorobenzylidene)-2-[4-(trans-4-methyl)cyclohexylbenzylidene]hydrazine
1-(3,4-difluorobenzylidene)-2-[4-(trans-4-ethyl)cyclohexylbenzylidene]hydrazine
1-(3,4-difluorobenzylidene)-2-[4-(trans-4-propyl)cyclohexylbenzylidene]hydrazine
1-(3,4-difluorobenzylidene)-2-[4-(trans-4-pentyl)cyclohexylbenzylidene]hydrazine
1-(3,4-difluorobenzylidene)-2-[4-(trans-4-hexyl)cyclohexylbenzylidene]hydrazine
1-(3,4-difluorobenzylidene)-2-[4-(trans-4-heptyl)cyclohexylbenzylidene]hydrazine
1-(3,4,5-trifluorobenzylidene)-2-[4-(trans-4-methyl)cyclohexylbenzylidene]hydrazine
1-(3,4,5-trifluorobenzylidene)-2-[4-(trans-4-ethyl)cyclohexylbenzylidene]hydrazine
1-(3,4,5-trifluorobenzylidene)-2-[4-(trans-4-propyl)cyclohexylbenzylidene]hydrazine
1-(3,4,5-trifluorobenzylidene)-2-[4-(trans-4-butyl)cyclohexylbenzylidene]hydrazine
1-(3,4,5-trifluorobenzylidene)-2-[4-(trans-4-pentyl)cyclohexylbenzylidene]hydrazine
1-(3,4,5-trifluorobenzylidene)-2-[4-(trans-4-hexyl)cyclohexylbenzylidene]hydrazine
1-(3,4,5-trifluorobenzylidene)-2-[4-(trans-4-heptyl)cyclohexylbenzylidene]hydrazine
1-(4-trifluoromethoxybenzylidene)-2-[4-(trans-4-methyl)cyclohexylbenzylidene]hydrazine
1-(4-trifluoromethoxybenzylidene)-2-[4-(trans-4-ethyl)cyclohexylbenzylidene]hydrazine
1-(4-trifluoromethoxybenzylidene)-2-[4-(trans-4-propyl)cyclohexylbenzylidene]hydrazine
1-(4-trifluoromethoxybenzylidene)-2-[4-(trans-4-butyl)cyclohexylbenzylidene]hydrazine
1-(4-trifluoromethoxybenzylidene)-2-[4-(trans-4-pentyl)cyclohexylbenzylidene]hydrazine
1-(4-trifluoromethoxybenzylidene)-2-[4-(trans-4-hexyl)cyclohexylbenzylidene]hydrazine 1-(4-trifluoromethoxybenzylidene)-2-[4-(trans-4-heptyl)cyclohexylbenzylidene]hydrazine
1-[4-(2-fluoro-4-methyl)phenylbenzylidene]-2-(4-methyl)benzylidenehydrazine
1-[4-(2-fluoro-4-ethyl)phenylbenzylidene]-2-(4-methyl)benzylidenehydrazine
1-[4-(2-fluoro-4-propyl)phenylbenzylidene]-2-(4-methyl)benzylidenehydrazine
1-[4-(2-fluoro-4-butyl)phenylbenzylidene]-2-(4-methyl)benzylidenehydrazine
1-[4-(2-fluoro-4-pentyl)phenylbenzylidene]-2-(4-methyl)benzylidenehydrazine
1-[4-(2-fluoro-4-hexyl)phenylbenzylidene]-2-(4-methyl)benzylidenehydrazine
1-[4-(2-fluoro-4-heptyl)phenylbenzylidene]-2-(4-methyl)benzylidenehydrazine
1-[4-(2-fluoro-4-methyl)phenylbenzylidene]-2-(4-ethyl)benzylidenehydrazine
1-[4-(2-fluoro-4-ethyl)phenylbenzylidene]-2-(4-ethyl)benzylidenehydrazine
1-[4-(2-fluoro-4-propyl)phenylbenzylidene]-2-(4-ethyl)benzylidenehydrazine
1-[4-(2-fluoro-4-butyl)phenylbenzylidene]-2-(4-ethyl)benzylidenehydrazine
1-[4-(2-fluoro-4-pentyl)phenylbenzylidene]-2-(4-ethyl)benzylidenehydrazine
1-[4-(2-fluoro-4-hexyl)phenylbenzylidene-]2-(4-ethyl)benzylidenehydrazine
1-[4-(2-fluoro-4-heptyl)phenylbenzylidene]-2-(4-ethyl)benzylidenehydrazine
1-[4-(2-fluoro-4-methyl)phenylbenzylidene]-2-(4-propyl)benzylidenehydrazine
1-[4-(2-fluoro-4-ethyl)phenylbenzylidene]-2-(4-propyl)benzylidenehydrazine
1-[4-(2-fluoro-4-propyl)phenylbenzylidene]-2-(4-propyl)benzylidenehydrazine
1-[4-(2-fluoro-4-butyl)phenylbenzylidene]-2-(4-propyl)benzylidenehydrazine
1-[4-(2-fluoro-4-pentyl)phenylbenzylidene]-2-(4-propyl)benzylidenehydrazine
1-[4-(2-fluoro-4-hexyl)phenylbenzylidene]-2-(4-propyl)benzylidenehydrazine
1-[4-(2-fluoro-4-heptyl)phenylbenzylidene]-2-(4-propyl)benzylidenehydrazine
1-[4-(2-fluoro-4-methyl)phenylbenzylidene]-2-(4-butyl)benzylidenehydrazine
1-[4-(2-fluoro-4-ethyl)phenylbenzylidene]-2-(4-butyl)benzylidenehydrazine
1-[4-(2-fluoro-4-propyl)phenylbenzylidene]-2-(4-butyl)benzylidenehydrazine
1-[4-(2-fluoro-4-butyl)phenylbenzylidene]-2-(4-butyl)benzylidenehydrazine
1-[4-(2-fluoro-4-pentyl)phenylbenzylidene]-2-(4-butyl)benzylidenehydrazine
1-[4-(2-fluoro-4-hexyl)phenylbenzylidene]-2-(4-butyl)benzylidenehydrazine
1-[4-(2-fluoro-4-heptyl)phenylbenzylidene]-2-(4-butyl)benzylidenehydrazine
1-[4-(2-fluoro-4-methyl)phenylbenzylidene]-2-(4-pentyl)benzylidenehydrazine
1-[4-(2-fluoro-4-ethyl)phenylbenzylidene]-2-(4-pentyl)benzylidenehydrazine
1-[4-(2-fluoro-4-propyl)phenylbenzylidene]-2-(4-pentyl)benzylidenehydrazine
1-[4-(2-fluoro-4-butyl)phenylbenzylidene]-2-(4-pentyl)benzylidenehydrazine
1-[4-(2-fluoro-4-pentyl)phenylbenzylidene-]2-(4-pentyl)benzylidenehydrazine
1-[4-(2-fluoro-4-hexyl)phenylbenzylidene]-2-(4-pentyl)benzylidenehydrazine
1-[4-(2-fluoro-4-heptyl)phenylbenzylidene-]2-(4-pentyl)benzylidenehydrazine
1-[4-(2-fluoro-4-methyl)phenylbenzylidene]-2-(4-hexyl)benzylidenehydrazine
1-[4-(2-fluoro-4-ethyl)phenylbenzylidene]-2-(4-hexyl)benzylidenehydrazine
1-[4-(2-fluoro-4-propyl)phenylbenzylidene]-2-(4-hexyl)benzylidenehydrazine
1-[4-(2-fluoro-4-butyl)phenylbenzylidene]-2-(4-hexyl)benzylidenehydrazine
1-[4-(2-fluoro-4-pentyl)phenylbenzylidene]-2-(4-hexyl)benzylidenehydrazine
1-[4-(2-fluoro-4-hexyl)phenylbenzylidene]-2-(4-hexyl)benzylidenehydrazine
1-[4-(2-fluoro-4-heptyl)phenylbenzylidene]-2-(4-hexyl)benzylidenehydrazine
1-[4-(2-fluoro-4-methyl)phenylbenzylidene]-2-(4-heptyl)benzylidenehydrazine
1-[4-(2-fluoro-4-ethyl)phenylbenzylidene]-2-(4-heptyl)benzylidenehydrazine
1-[4-(2-fluoro-4-propyl)phenylbenzylidene]-2-(4-heptyl)benzylidenehydrazine
1-[4-(2-fluoro-4-butyl)phenylbenzylidene]-2-(4-heptyl)benzylidenehydrazine
1-[4-(2-fluoro-4-pentyl)phenylbenzylidene-]2-(4-heptyl)benzylidenehydrazine
1-[4-(2-fluoro-4-hextyl)phenylbenzylidene]-2-(4-heptyl)benzylidenehydrazine
1-[4-(2-fluoro-4-heptyl)phenylbenzylidene]-2-(4-heptyl)benzylidenehydrazine
1-[4-(2-fluoro-4-methyl)phenylbenzylidene]-2-[4-(3-butenyl)benzylidene]hydrazine
1-[4-(2-fluoro-4-ethyl)phenylbenzylidene]-2-[4-(3-butenyl)benzylidene]hydrazine
1-[4-(2-fluoro-4-propyl)phenylbenzylidene]-2-[4-(3-butenyl)benzylidene]hydrazine
1-[4-(2-fluoro-4-butyl)phenylbenzylidene]-2-[4-(3-butenyl)benzylidene]hydrazine
1-[4-(2-fluoro-4-pentyl)phenylbenzylidene]-2-[4-(3-butenyl)benzylidene]hydrazine
1-[4-(2-fluoro-4-hexyl)phenylbenzylidene]-2-[4-(3-butenyl)benzylidene]hydrazine
1-[4-(2-fluoro-4-heptyl)phenylbenzylidene]-2-[4-(3-butenyl)benzylidene]hydrazine
1-[4-(2-fluoro-4-methyl)phenylbenzylidene]-2-[4-(4-pentenyl)benzylidene]hydrazine
1-[4-(2-fluoro-4-ethyl)phenylbenzylidene]-2-[4-(4-pentenyl)benzylidene]hydrazine
1-[4-(2-fluoro-4-propyl)phenylbenzylidene]-2-[4-(4-pentenyl)benzylidene]hydrazine
1-[4-(2-fluoro-4-butyl)phenylbenzylidene]-2-[4-(4-pentenyl)benzylidene]hydrazine
1-[4-(2-fluoro-4-pentyl)phenylbenzylidene]-2-[4-(4-pentenyl )benzylidene]hydrazine
1-[4-(2-fluoro-4-hexyl)phenylbenzylidene]-2-[4-(4-pentenyl)benzylidene]hydrazine
1-[4-(2-fluoro-4-heptyl)phenylbenzylidene]-2-[4-(4-pentenyl)benzylidene]hydrazine
1-[4-(2-fluoro-4-methyl)phenylbenzylidene]-2-[4-(5-hexenyl)benzylidene]hydrazine
1-[4-(2-fluoro-4-ethyl)phenylbenzylidene]-2-[4-(5-hexenyl)benzylidene]hydrazine
1-[4-(2-fluoro-4-propyl)phenylbenzylidene]-2-[4-(5-hexenyl)benzylidene]hydrazine
1-[4-(2-fluoro-4-butyl)phenylbenzylidene]-2-[4-(5-hexenyl)benzylidene]hydrazine 1-[4-(2-fluoro-4-pentyl)phenylbenzylidene]-2-[4-(5-hexenyl)benzylidene]hydrazine
1-[4-(2-fluoro-4-hexyl)phenylbenzylidene]-2-[4-(5-hexenyl)benzylidene]hydrazine
1-[4-(2-fluoro-4-heptyl)phenylbenzylidene]-2-[4-(5-hexenyl)benzylidene]hydrazine
1-[4-(2-fluoro-4-methyl)phenylbenzylidene]-2-[4-(6-heptenyl)benzylidene]hydrazine
1-[4-(2-fluoro-4-ethyl)phenylbenzylidene]-2-[4-(6-heptenyl)benzylidene]hydrazine
1-[4-(2-fluoro-4-propyl)phenylbenzylidene]-2-[4-(6-heptenyl)benzylidene]hydrazine
1-[4-(2-fluoro-4-butyl)phenylbenzylidene]-2-[4-(6-heptenyl)benzylidene]hydrazine
1-[4-(2-fluoro-4-pentyl)phenylbenzylidene]-2-[4-(6-heptenyl)benzylidene]hydrazine
1-[4-(2-fluoro-4-hexyl)phenylbenzylidene]-2-[4-(6-heptenyl)benzylidene]hydrazine
1-[4-(2-fluoro-4-heptyl)phenylbenzylidene]-2-[4-(6-heptenyl)benzylidene]hydrazine
1-[4-(2-fluoro-4-methyl)phenylbenzylidene]-2-(4-fluoro)benzylidenehydrazine
1-[4-(2-fluoro-4-ethyl)phenylbenzylidene]-2-(4-fluoro)benzylidenehydrazine
1-[4-(2-fluoro-4-propyl)phenylbenzylidene]-2-(4-fluoro)benzylidenehydrazine
1-[4-(2-fluoro-4-butyl)phenylbenzylidene]-2-(4-fluoro)benzylidenehydrazine
1-[4-(2-fluoro-4-pentyl)phenylbenzylidene-]2-(4-fluoro)benzylidenehydrazine
1-[4-(2-fluoro-4-hexyl)phenylbenzylidene]-2-(4-fluoro)benzylidenehydrazine
1-[4-(2-fluoro-4-heptyl)phenylbenzylidene]-2-(4-fluoro)benzylidenehydrazine
1-[4-(2-fluoro-4-methyl)phenylbenzylidene]-2-(3,4-difluoro)benzylidenehydrazine
1-[4-(2-fluoro-4-ethyl)phenylbenzylidene]-2-(3,4-difluoro)benzylidenehydrazine
1-[4-(2-fluoro-4-propyl)phenylbenzylidene]-2-(3,4-difluoro)benzylidenehydrazine
1-[4-(2-fluoro-4-butyl)phenylbenzylidene]-2-(3,4-difluoro)benzylidenehydrazine
1-[4-(2-fluoro-4-pentyl)phenylbenzylidene]-2-(3,4-difluoro)benzylidenehydrazine
1-[4-(2-fluoro-4-hexyl)phenylbenzylidene]-2-(3,4-difluoro)benzylidenehydrazine
1-[4-(2-fluoro-4-heptyl)phenylbenzylidene]-2-(3,4-difluoro)benzylidenehydrazine
1-[4-(4-methylphenyl)-3-fluorobenzylidene]-2-(4-methyl)benzylidenehydrazine
1-[4-(4-methylphenyl)-3-fluorobenzylidene]-2-(4-ethyl)benzylidenehydrazine
1-[4-(4-methylphenyl)-3-fluorobenzylidene]-2-(4-propyl)benzylidenehydrazine
1-[4-(4-methylphenyl)-3-fluorobenzylidene]-2-(4-butyl)benzylidenehydrazine
1-[4-(4-methylphenyl)-3-fluorobenzylidene]-2-(4-pentyl)benzylidenehydrazine
1-[4-(4-methylphenyl)-3-fluorobenzylidene]-2-(4-hexyl)benzylidenehydrazine
1-[4-(4-methylphenyl)-3-fluorobenzylidene]-2-(4-heptyl)benzylidenehydrazine
1-[4-(4-methylphenyl)-3-fluorobenzylidene]-2-(4-(3-butenyl)benzylidenehydrazine
1-[4-(4-methylphenyl)-3-fluorobenzylidene]-2-[4-(4-pentenyl)]benzylidenehydrazine
1-[4-(4-methylphenyl)-3-fluorobenzylidene]-2-[4-(5-hexenyl)]benzylidenehydrazine
1-[4-(4-methylphenyl)-3-fluorobenzylidene]-2-[4-(6-heptenyl)]benzylidenehydrazine
1-[4-(4-ethylphenyl)-3-fluorobenzylidene]-2-(4-methyl)benzylidenehydrazine
1-[4-(4-ethylphenyl)-3-fluorobenzylidene]-2-(4-ethyl)benzylidenehydrazine
1-[4-(4-ethylphenyl)-3-fluorobenzylidene]-2-(4-propyl)benzylidenehydrazine
1-[4-(4-ethylphenyl)-3-fluorobenzylidene]-2-(4-butyl)benzylidenehydrazine
1-[4-(4-ethylphenyl)-3-fluorobenzylidene]-2-(4-pentyl)benzylidenehydrazine
1-[4-(4-ethylphenyl)-3-fluorobenzylidene]-2-(4-hexyl)benzylidenehydrazine
1-[4-(4-ethylphenyl)-3-fluorobenzylidene]-2-(4-heptyl)benzylidenehydrazine
1-[4-(4-ethylphenyl)-3-fluorobenzylidene]-2-[4-(3-butenyl)]benzylidenehydrazine
1-[4-(4-ethylphenyl)-3-fluorobenzylidene]-2-[4-(4-pentenyl)]benzylidenehydrazine
1-[4-(4-ethylphenyl)-3-fluorobenzylidene]-2-[4-(5-hexenyl)]benzylidenehydrazine
1-[4-(4-ethylphenyl)-3-fluorobenzylidene]-2-[4-(6-heptenyl)]benzylidenehydrazine
1-[4-(4-propylphenyl)-3-fluorobenzylidene]-2-(4-methyl)benzylidenehydrazine
1-[4-(4-propylphenyl)-3-fluorobenzylidene]-2-(4-ethyl)benzylidenehydrazine
1-[4-(4-propylphenyl )-3-fluorobenzylidene]-2-(4-propyl)benzylidenehydrazine
1-[4-(4-propylphenyl)-3-fluorobenzylidene]-2-(4-butyl)benzylidenehydrazine
1-[4-(4-propylphenyl)-3-fluorobenzylidene]-2-(4-pentyl)benzylidenehydrazine
1-[4-(4-propylphenyl)-3-fluorobenzylidene]-2-(4-hexyl)benzylidenehydrazine
1-[4-(4-propylphenyl)-3-fluorobenzylidene]-2-(4-heptyl)benzylidenehydrazine
1-[4-(4-propylphenyl)-3-fluorobenzylidene]-2-[4-(3-butenyl)]benzylidenehydrazine
1-[4-(4-propylphenyl)-3-fluorobenzylidene]-2-[4-(4-pentenyl)]benzylidenehydrazine
1-[4-(4-propylphenyl)-3-fluorobenzylidene]-2-[4-(5-hexenyl)]benzylidenehydrazine
1-[4-(4-propylphenyl)-3-fluorobenzylidene]-2-[4-(6-heptenyl)]benzylidenehydrazine
1-[4-(4-butylphenyl)-3-fluorobenzylidene]-2-(4-methyl)benzylidenehydrazine
1-[4-(4-butylphenyl)-3-fluorobenzylidene]-2-(4-ethyl)benzylidenehydrazine
1-[4-(4-butylphenyl)-3-fluorobenzylidene]-2-(4-propyl)benzylidenehydrazine
1-[4-(4-butylphenyl)-3-fluorobenzylidene]-2-(4-butyl)benzylidenehydrazine
1-[4-(4-butylphenyl)-3-fluorobenzylidene]-2-(4-pentyl)benzylidenehydrazine
1-[4-(4-butylphenyl)-3-fluorobenzylidene]-2-(4-hexyl)benzylidenehydrazine
1-[4-(4-butylphenyl)-3-fluorobenzylidene]-2-(4-heptyl)benzylidenehydrazine
1-[4-(4-butylphenyl)-3-fluorobenzylidene]-2-[4-(3-butenyl)]benzylidenehydrazine
1-[4-(4-butylphenyl)-3-fluorobenzylidene]-2-[4-(4-pentenyl)]benzylidenehydrazine
1-[4-(4-butylphenyl)-3-fluorobenzylidene]-2-[4-(5-hexenyl)]benzylidenehydrazine
1-[4-(4-butylphenyl)-3-fluorobenzylidene]-2-[4-(6-heptenyl)]benzylidenehydrazine 1-[4-(4-pentylphenyl)-3-fluorobenzylidene]-2-(4-methyl)benzylidenehydrazine
1-[4-(4-pentylphenyl)-3-fluorobenzylidene]-2-(4-ethyl)benzylidenehydrazine
1-[4-(4-pentylphenyl)-3-fluorobenzylidene-]2-(4-propyl)benzylidenehydrazine
1-[4-(4-pentylphenyl)-3-fluorobenzylidene]-2-(4-butyl)benzylidenehydrazine
1-[4-(4-pentylphenyl)-3-fluorobenzylidene-]2-(4-pentyl)benzylidenehydrazine
1-[4-(4-pentylphenyl)-3-fluorobenzylidene]-2-(4-hexyl)benzylidenehydrazine
1-[4-(4-pentylphenyl)-3-fluorobenzylidene]-2-(4-heptyl)benzylidenehydrazine
1-[4-(4-pentylphenyl)-3-fluorobenzylidene]-2-[4-(3-butenyl)]benzylidenehydrazine
1-[4-(4-pentylphenyl)-3-fluorobenzylidene]-2-[4-(4-pentenyl)]benzylidenehydrazine
1-[4-(4-pentylphenyl)-3-fluorobenzylidene]-2-[4-(5-hexenyl)]benzylidenehydrazine
1-[4-(4-pentylphenyl)-3-fluorobenzylidene]-2-[4-(6-heptenyl)]benzylidenehydrazine
1-[4-(4-hexylphenyl)-3-fluorobenzylidene]-2-(4-methyl)benzylidenehydrazine
1-[4-(4-hexylphenyl)-3-fluorobenzylidene]-2-(4-ethyl)benzylidenehydrazine
1-[4-(4-hexylphenyl)-3-fluorobenzylidene]-2-(4-propyl)benzylidenehydrazine
1-[4-(4-hexylphenyl)-3-fluorobenzylidene]-2-(4-butyl)benzylidenehydrazine
1-[4-(4-hexylphenyl)-3-fluorobenzylidene]-2-(4-pentyl)benzylidenehydrazine
1-[4-(4-hexylphenyl)-3-fluorobenzylidene]-2-(4-hexyl)benzylidenehydrazine
1-[4-(4-hexylphenyl)-3-fluorobenzylidene]-2-(4-heptyl)benzylidenehydrazine
1-[4-(4-hexylphenyl)-3-fluorobenzylidene]-2-[4-(3-butenyl)]benzylidenehydrazine
1-[4-(4-hexylphenyl)-3-fluorobenzylidene]-2-[4-(4-pentenyl)]benzylidenehydrazine
1-[4-(4-hexylphenyl)-3-fluorobenzylidene]-2-[4-(5-hexenyl)]benzylidenehydrazine
1-[4-(4-hexylphenyl)-3-fluorobenzylidene]-2-[4-(6-heptenyl)]benzylidenehydrazine
1-[4-(4-heptylphenyl)-3-fluorobenzylidene]-2-(4-methyl)benzylidenehydrazine
1-[4-(4-heptylphenyl)-3-fluorobenzylidene]-2-(4-ethyl)benzylidenehydrazine
1-[4-(4-heptylphenyl)-3-fluorobenzylidene]-2-(4-propyl)benzylidenehydrazine
1-[4-(4-heptylphenyl)-3-fluorobenzylidene]-2-(4-butyl)benzylidenehydrazine
1-[4-(4-heptylphenyl)-3-fluorobenzylidene]-2-(4-pentyl)benzylidenehydrazine
1-[4-(4-heptylphenyl)-3-fluorobenzylidene]-2-(4-hexyl)benzylidenehydrazine
1-[4-(4-heptylphenyl)-3-fluorobenzylidene]-2-(4-heptyl)benzylidenehydrazine
1-[4-(4-heptylphenyl)-3-fluorobenzylidene]-2-[4-(3-butenyl)]benzylidenehydrazine
1-[4-(4-heptylphenyl)-3-fluorobenzylidene]-2-[4-(4-pentenyl)]benzylidenehydrazine
1-[4-(4-heptylphenyl)-3-fluorobenzylidene]-2-[4-(5-hexenyl)]benzylidenehydrazine
1-[4-(4-heptylphenyl)-3-fluorobenzylidene]-2-[4-(6-heptenyl)]benzylidenehydrazine

EXAMPLE 14

Preparation of Liquid Crystal Composition (6)

A liquid crystal composition (M-12) consisting of 80% of the host liquid crystal (H) and 20% of Compound No. 12:

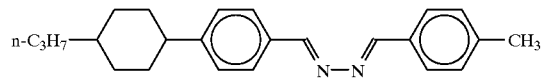

was prepared. The liquid crystal composition (M-12) exhibited an upper nematic phase temperature limit ($T_{N-1}$) of 157.2° C., which is a drastic increase from that of the host liquid crystal (H). The liquid crystal composition was then allowed to stand at a temperature of 0° C. for 24 hours. As a result, no crystallization was observed. This liquid crystal composition was allowed to stand at a temperature of −78° C. for a prolonged period of time so that it was solidified. While being heated, this liquid crystal composition was measured for temperature at which it again turns to uniform nematic phase ($T_{-N}$). The results were as low as −8° C. This demonstrates that the incorporation of Compound No. 12 as an n-type azine derivative in the host liquid crystal in an amount of 20% by weight provides extension of nematic phase temperature range by as great as 59.5° C.

A 4.5 $\mu$m thick liquid crystal device was then prepared from this composition in the same manner as mentioned above. The liquid crystal device thus prepared was then measured for switching time. The results were 16.0 msec., which demonstrates that the response is very fast. The liquid crystal device was then measured for threshold voltage (Vth). The results were 1.88 V. The liquid crystal device exhibited a birefringence index ($\Delta n$) as great as 0.131.

EXAMPLE 15

Preparation of Liquid Crystal Composition (7)

A liquid crystal composition (M-15) consisting of 80% of the host liquid crystal (H) and the same amount (20% by weight) of Compound No. 15 as an azine derivative:

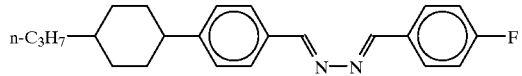

was prepared. The liquid crystal composition (M-15) exhibited an upper nematic phase temperature limit ($T_{N-1}$) of 144.1° C., which is an increase of about 30° C. from that of the host liquid crystal (H) (116.7° C.). A liquid crystal device was then prepared from this liquid crystal composition in the same manner as mentioned above. The liquid crystal device thus prepared was then measured for switching time. The results were 17.0 msec., which demonstrates that the device can respond at a higher rate than the host liquid crystal (H), though slightly inferior to the liquid crystal composition (M-12), which comprised 20% by weight of Compound No. 12 as an n-type azine derivative incorporated therein. Further, the liquid crystal device exhibited a birefringence index ($\Delta n$) as great as 0.131. The liquid crystal device was measured for threshold voltage. The results were 2.42 V, which is an improvement over that of the liquid crystal composition (M-12), which comprised 20% by weight of Compound No. 12 as an n-type azine derivative incorporated therein, though slightly higher than that of the host liquid crystal (H).

EXAMPLE 16

Preparation of Liquid Crystal Composition (8)

To 80% of the host liquid crystal (H) was added Compound No. 13 as an n-type azine derivative:

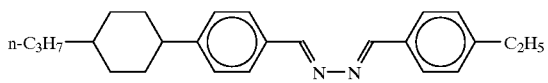

in the same amount as mentioned above (20% by weight) to prepare a liquid crystal composition (M-13). The liquid crystal composition (M-13) exhibited an upper nematic phase temperature limit ($T_{N-1}$) of 152.6° C. A liquid crystal device was prepared from this liquid crystal composition in the same manner as mentioned above. The liquid crystal device thus prepared was then measured for switching time. The results were 17.4 msec. The liquid crystal device also exhibited a birefringence index ($\Delta n$) of 0.137. The liquid crystal device was measured for threshold voltage. The results were 2.54 V.

EXAMPLE 17

Preparation of Liquid Crystal Composition (9)

A liquid crystal composition (M-14) consisting of 80% of the host liquid crystal (H) and 20% of Compound No. 14 as an n-type azine derivative:

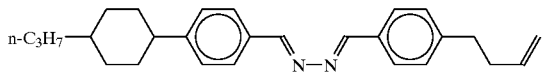

was prepared. The liquid crystal composition (M-14) exhibited an upper nematic phase temperature limit ($T_{N-1}$) of 153.3° C. A liquid crystal device was then prepared from this liquid crystal composition in the same manner as mentioned above. The liquid crystal device thus prepared was then measured for switching time. The results were 16.3 msec. The liquid crystal device also exhibited a birefringence index ($\Delta n$) of 0.136. The liquid crystal device was then measured for threshold voltage. The results were 2.69 V.

EXAMPLE 18

Preparation of Liquid Crystal Composition (10)

A liquid crystal composition (M-16) consisting of 80% by weight of the host liquid crystal (H) and 20% by weight of Compound No. 16 as a p-type azine derivative:

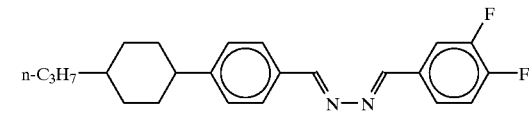

was prepared. The liquid crystal composition (M-16) exhibited an upper nematic phase temperature limit ($T_{N-1}$) of 146.3° C. A liquid crystal device was then prepared from this liquid crystal composition in the same manner as mentioned above. The liquid crystal device thus prepared was then measured for switching time. The results were 21.0 msec. The liquid crystal device also exhibited a birefringence index ($\Delta n$) of 0.128. The liquid crystal device was then measured for threshold voltage. The results were 2.07 V.

The nematic liquid crystal composition of the present invention will be further described in the following examples, but the present invention should not be construed as being limited thereto. The term "%" as used for composition is meant to indicate "% by weight".

For the evaluation of the chemical stability of the composition, 2 g of the liquid crystal composition was charged in an ampoule. The air in the ampoule was then replaced by nitrogen. The ampoule was then sealed. The specimen was then subjected to heat acceleration test at a temperature of 150° C. for 1 hour. The liquid crystal composition was then measured for specific resistivity. The properties measured in the examples were as follows:

$T_{N-1}$: Nematic phase-isotropic liquid phase transition temperature (°C.)

$T \rightarrow_N$: Solid phase or smectic phase-nematic phase transition temperature (°C.)

$V_{th}$: Threshold voltage (V) in the form of TN-LCD having a cell thickness of 6 μm γ: Sharpness Δε: Dielectric anisotropy η: Viscosity (c.p.) at 20° C.

EXAMPLE 19

A nematic liquid crystal composition (2-1) consisting of the following components:

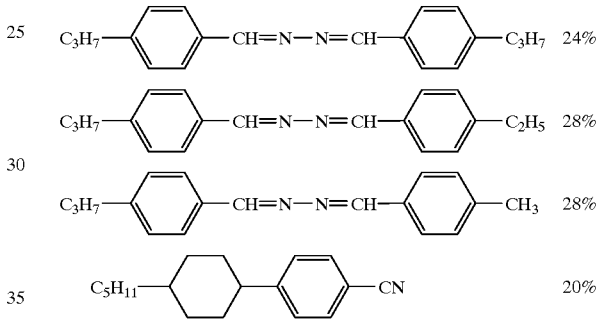

was prepared. The liquid crystal composition was measured for various properties. The results were as follows:

$T_{N-1}$: 93.6° C.

$T \rightarrow_N$: -1.0° C.

$V_{th}$: 2.59 V

γ: 1.15

Δε: 4.9

Δn: 0.281

This nematic liquid crystal composition was used to prepare TN-LCD having a cell thickness d of 1.8 μm. TN-LCD thus prepared was then measured for display properties. As a result, a liquid crystal display system which exhibits a threshold voltage of 2.28 V and a switching time of 1.1 msec. was obtained.

The foregoing nematic liquid crystal composition was also measured for wavelength dispersion of birefringence index. As a result, the ratio of birefringence index at a wavelength of 400 nm to that at a wavelength of 650 nm was not less than 1.15. Since this liquid crystal material exhibits a greater phase difference with different light wavelength, it is understood that this liquid crystal material is useful for a novel reflective type color liquid crystal display system utilizing birefringence of liquid crystal and retardation film which performs color display without any color filter layer.

To this nematic liquid crystal composition was then added a chiral substance "S-811" (available from Merck Co., Ltd.) to prepare a mixed liquid crystal. Separately, an organic film of "Sunever 610" (available from Nissan Chemical Industries, Ltd.) provided on opposing flat transparent electrodes was rubbed to form an alignment film. Thus, an STN-LCD display cell having a twist angle of 220° was prepared. The foregoing mixed liquid crystal was poured into the cell to prepare a liquid crystal display system which was then measured for display properties. As a result, a liquid crystal display system which exhibits excellent STN-LCD display properties, i.e., high multiplexing properties and improved fast response was obtained. The addition of the chiral substance was effected in such a manner that the inherent helical pitch P of the mixed liquid crystal and the cell thickness d of the display cell satisfy the following relationships:

Δn·d=0.85 d/P=0.53

EXAMPLE 20

A nematic liquid crystal composition (2-2) consisting of the following components:

| Component | Weight % |
|---|---|
| $C_3H_7$—⌬—CH=N—N=CH—⌬—$CH_3$ | 20% by weight |
| $C_3H_7$—⬡—⌬—CN | 13.6% by weight |
| $C_5H_{11}$—⬡—⌬—CN | 13.2% by weight |
| $C_7H_{15}$—⬡—⌬—CN | 13.2% by weight |
| $C_3H_7$—⬡—COO—⌬—$OC_2H_5$ | 6.8% by weight |
| $C_4H_9$—⬡—COO—⌬—$OC_2H_5$ | 6.8% by weight |
| $C_5H_{11}$—⬡—COO—⌬—$OCH_3$ | 6.8% by weight |
| $C_3H_7$—⬡—COO—⌬—$OC_4H_9$ | 6.8% by weight |
| $C_4H_9$—⬡—COO—⌬—$OCH_3$ | 6.4% by weight |
| $C_5H_{11}$—⬡—COO—⌬—$OC_2H_5$ | 6.4% by weight | was prepared. The liquid crystal composition was measured for various properties. The results were as follows:

$T_{N-1}$: 67.3° C.

$T \rightarrow_N$: −70° C.

$V_{th}$: 1.85 V

γ: 1.12

Δε: 6.6

Δn: 0.145

η: 24.1 c.p.

Specific resistivity before test: $6.0 \times 10^{11}$ Ω·cm

Specific resistivity after heat acceleration test: $4.3 \times 10^{11}$ Ω·cm

This nematic liquid crystal composition exhibits γ of 1.12, which is the same as the limit of the optical sharpness of liquid crystal display devices disclosed in "High Speed Liquid Crystal Technology", page 63, CMC. Accordingly, it can be understood that this liquid crystal composition is useful for high multiplex driving.

Since this nematic liquid crystal composition exhibits a high specific resistivity after heat acceleration test, it can be understood that this nematic liquid crystal composition is high stability to heat. A new nematic liquid crystal composition comprising this composition as an essential constituent material was prepared. This nematic liquid crystal composition was then used to prepare a twisted nematic and super twisted nematic liquid crystal display systems. These nematic liquid crystal display systems were confirmed to be excellent liquid crystal display systems which show no flickering.

The foregoing nematic liquid crystal composition (2-2) comprises an azine compound incorporated in the following host liquid crystal (b-1). The host liquid crystal (b-1) was then measured for various properties. The results were as follows:

Host liquid crystal (b-1)

| Component | Weight % |
|---|---|
| $C_3H_7$—⬡—⌬—CN | 17.0% by weight |
| $C_5H_{11}$—⬡—⌬—CN | 16.5% by weight |
| $C_7H_{15}$—⬡—⌬—CN | 16.5% by weight |
| $C_3H_7$—⬡—COO—⌬—$OC_2H_5$ | 8.5% by weight |
| $C_4H_9$—⬡—COO—⌬—$OC_2H_5$ | 8.5% by weight |
| $C_5H_{11}$—⬡—COO—⌬—$OCH_3$ | 8.5% by weight |
| $C_3H_7$—⬡—COO—⌬—$OC_4H_9$ | 8.5% by weight |
| $C_4H_9$—⬡—COO—⌬—$OCH_3$ | 8.0% by weight |
| $C_5H_{11}$—⬡—COO—⌬—$OC_2H_5$ | 8.0% by weight |

$T_{N-1}$: 54.5° C.

$T \rightarrow_N$: −40° C.

$V_{th}$: 1.60 V

γ: 1.13

Δε: 6.7

Δn: 0.092

η: 21.0 c.p.

The comparison of the foregoing liquid crystal compositions in properties shows that the liquid crystal composition of the present invention exhibits a larger birefringence index, a broader nematic phase temperature range and a smaller ratio γ of saturated voltage to threshold voltage and thus gives better results. However, the foregoing azine compound exhibited a higher viscosity and thus showed a tendency to increase the viscosity of the host liquid crystal (b-1).

Despite the foregoing viscosity properties, a surprising fact was found. In other words, the liquid crystal composition (2-2) of the present invention and the host liquid crystal (b-1) were measured for response time. The comparison of the response time of these liquid crystals shows that the host liquid crystal composition (b-1) exhibits a switching time of 39.2 msec. while the liquid crystal composition (2-2) exhibits a switching time of 35.6 msec. and gives better results.

It can be seen in the fact that despite its high viscosity the foregoing azine compound exerts an effect of shortening the switching time. This effect gives an expectation that physical properties such as elastic constant and rotational viscosity of the azine compound have a specific tendency.

EXAMPLE 21

A nematic liquid crystal composition (2-3) consisting of the following components:

Nematic Liquid Crystal Composition (2-3)

| Structure | Amount |
|---|---|
| $C_3H_7$–⟨phenyl⟩–CH=N—N=CH–⟨phenyl⟩–$CH_3$ | 8% by weight |
| $C_3H_7$–⟨phenyl⟩–CH=N—N=CH–⟨phenyl⟩–F | 8% by weight |
| CH$_2$=CH–⟨cyclohexyl⟩–⟨cyclohexyl⟩–$C_5H_{11}$ | 10% by weight |
| CH$_2$=CH–CH$_2$–⟨cyclohexyl⟩–⟨cyclohexyl⟩–$C_3H_7$ | 10% by weight |
| CH$_2$=CH–⟨cyclohexyl⟩–⟨cyclohexyl⟩–⟨phenyl⟩–$CH_3$ | 9% by weight |
| CH$_2$=CH–CH$_2$–⟨cyclohexyl⟩–⟨cyclohexyl⟩–⟨phenyl⟩–$CH_3$ | 9% by weight |
| $C_3H_7$–⟨cyclohexyl⟩–⟨phenyl⟩–C≡C–⟨phenyl⟩–$C_2H_5$ | 8% by weight |
| $C_4H_9$–⟨cyclohexyl⟩–⟨phenyl⟩–C≡C–⟨phenyl⟩–$CH_3$ | 8% by weight |
| CH$_2$=CH–⟨cyclohexyl⟩–⟨phenyl⟩–CN | 10% by weight |
| CH$_2$=CH–CH$_2$–⟨cyclohexyl⟩–⟨phenyl⟩–CN | 10% by weight |
| $C_5H_{11}$–⟨pyrimidine⟩–⟨phenyl⟩–CN | 4% by weight |
| $C_4H_9$–⟨phenyl⟩–COO–⟨phenyl(F)⟩–CN | 6% by weight | was prepared. The liquid crystal composition was measured for various properties. The results were as follows:

$T_{N-1}$: 96.1° C.
$T \rightarrow_N$: −70.0° C.
$V_{th}$: 1.89 V
$\gamma$: 1.15
$\Delta\epsilon$: 8.9
$\Delta n$: 0.171

To this nematic liquid crystal composition was then added a chiral substance "S-811" (available from Merck Co., Ltd.) to prepare a mixed liquid crystal. Separately, an organic film of "Sunever 610" (available from Nissan Chemical Industries, Ltd.) provided on opposing flat transparent electrodes was rubbed to form an alignment film. Thus, an STN-LCD display cell having a twist angle of 220° was prepared. The foregoing mixed liquid crystal was poured into the cell to prepare a liquid crystal display system which was then measured for display properties. As a result, a liquid crystal display system which exhibits excellent STN-LCD display properties, i.e., high multiplexing properties and improved fast response was obtained. The addition of the chiral substance was effected in such a manner that the inherent helical pitch P of the mixed liquid crystal and the cell thickness d of the display cell satisfy the following relationships:

$\Delta n \cdot d = 0.85$ $d/P = 0.53$

EXAMPLE 22

A nematic liquid crystal composition (2-4) consisting of the following components:

Nematic Liquid Crystal Composition (2-4)

$C_3H_7$—⟨ring⟩—CH=N—N=CH—⟨ring⟩—$CH_3$    20% by weight

⟨structure f⟩    40% by weight

⟨structure⟩    40% by weight was prepared. The liquid crystal composition was measured for various properties. The results were as follows:

$T_{N-1}$: 115.6° C.

$T \rightarrow_N$: −8.0° C.

$V_{th}$: 2.70 V $\gamma$: 1.13

$\Delta\epsilon$: 3.9

$\Delta n$: 0.143

$\eta$: 23.1 c.p.

Specific resistivity before test: $6.0 \times 10^{11}$ $\Omega \cdot cm$

Specific resistivity after heat acceleration test: $6.3 \times 10^{11}$ $\Omega \cdot cm$ Voltage holding ratio before test: 98.4%

Voltage holding ratio after heat acceleration test: 98.0%

This nematic liquid crystal composition exhibits γ close to the limit (1.12) of the optical sharpness of liquid crystal display devices disclosed in "High Speed Liquid Crystal Technology", page 63, CMC. Accordingly, it can be understood that this liquid crystal composition is useful for high multiplex driving.

Since this nematic liquid crystal composition exhibits a high specific resistivity and a high voltage holding ratio after heat acceleration test, it can be understood that this nematic liquid crystal composition is higher stability to heat. A new nematic liquid crystal composition comprising this composition as an essential constituent material was prepared. This nematic liquid crystal composition was then used to prepare an active matrix liquid crystal display system. The liquid crystal display system was confirmed to be an excellent liquid crystal display system which show little current leakage and no flickering. Similarly, another nematic liquid crystal composition of the present invention comprising this composition as an essential constituent material was prepared.

The foregoing nematic liquid crystal composition (2-4) comprises an azine compound incorporated in the following host liquid crystal (H):

Host Liquid Crystal (H)

⟨structure⟩    50% by weight

⟨structure⟩    50% by weight

The host liquid crystal (H) was then measured for various properties. The results were as follows:

$T_{N-1}$: 116.7° C.

$T \rightarrow_N$: +11.0° C.

$V_{th}$: 2.14 V $\gamma$: 1.23

$\Delta\epsilon$: 4.8

$\Delta n$: 0.090

$\eta$: 19.8 c.p.

The comparison of the foregoing liquid crystal compositions in properties shows that the liquid crystal composition of the present invention exhibits a larger birefringence index, a broader nematic phase temperature range and a smaller sharpness and thus gives better results. However, the foregoing azine compound exhibited a higher viscosity and thus showed a tendency to increase the viscosity of the host liquid crystal (H).

Despite the foregoing viscosity properties, a surprising fact was found. In other words, the liquid crystal composition (2-4) of the present invention and the host liquid crystal (H) were measured for response. The comparison of the response of these liquid crystals shows that the host liquid crystal composition (H) exhibits a switching time of 25.3 msec. while the liquid crystal composition (2-4) exhibits a switching time of 21.3 msec. and gives better results. It can be seen in the fact that despite its higher viscosity the foregoing azine compound exerts an effect of shortening the switching time. This effect gives an expectation that physical properties such as elastic constant and rotational viscosity of the azine compound have a specific tendency.

EXAMPLE 23

A nematic liquid crystal composition (2-5) consisting of the following components:

Nematic Liquid Crystal Composition (2-5)

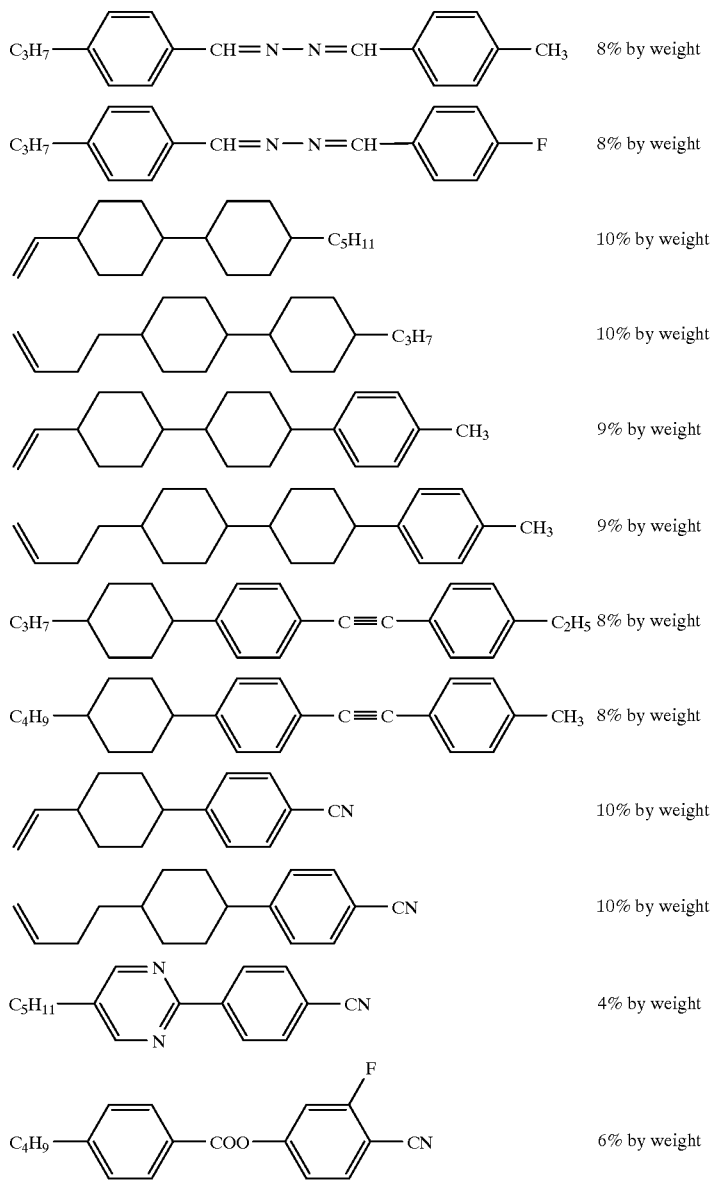

was prepared. The liquid crystal composition was measured for various properties. The results were as follows:

$T_{N-1}$: 100.1° C.
$T \to_N$: −70.0° C.
$V_{th}$: 2.01 V
γ: 1.15
Δε: 8.6
Δn: 0.173

To this nematic liquid crystal composition was then added a chiral substance "S-811" (available from Merck Co., Ltd.) to prepare a mixed liquid crystal. Separately, an organic film of "Sunever 610" (available from Nissan Chemical Industries, Ltd.) provided on opposing flat transparent electrodes was rubbed to form an alignment film. Thus, an STN-LCD display cell having a twist angle of 220° was prepared. The foregoing mixed liquid crystal was poured into the cell to prepare a liquid crystal display system which was then measured for display properties. As a result, a liquid crystal display system which exhibits excellent STN-LCD display properties, i.e., high multiplexing properties and improved fast response was obtained. The addition of the chiral substance was effected in such a manner that the inherent helical pitch P of the mixed liquid crystal and the cell thickness d of the display cell satisfy the following relationships:

$\Delta n \cdot d = 0.85$ $d/P = 0.53$

EXAMPLE 24

A nematic liquid crystal composition (2-6) consisting of the following components:

Nematic Liquid Crystal Composition (2-6)

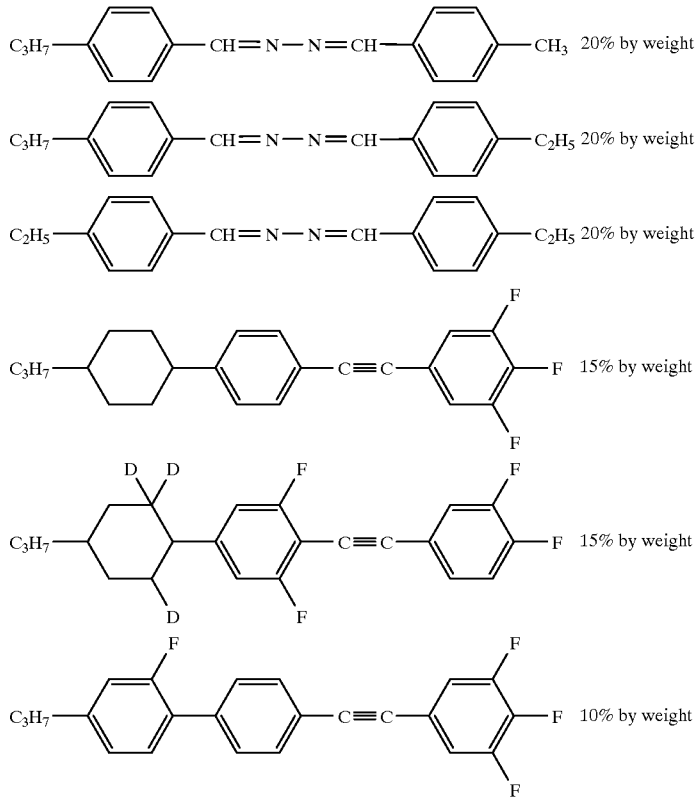

was prepared. This liquid crystal composition exhibits a larger birefringence index, a broader nematic phase temperature range, a smaller ratio γ of saturated voltage to threshold voltage and a fast response and thus gives better results.

The light-scattering type liquid crystal display device comprising this liquid crystal composition will be further described hereinafter, but the present invention should not be construed as being limited thereto.

The liquid crystal composition (2-6) as a liquid crystal material, a polymer-forming compound "HX-220" (available from Nippon Kayaku Co., Ltd.), lauryl acrylate, and 2-hydroxy-2-methyl-1-phenylpropane-1-one were mixed in a proportion of 80%, 13.86%, 5.94% and 0.2%, respectively, to prepare a uniform solution of light-control layer-forming material. The light-control layer-forming material was then vacuum-injected into a 50×50 mm vacant cell, prepared from a pair of ITO electrode glass substrates having spacers with an average particle diameter of 10 μm, interposed therebetween at a temperature of more than 10° C. higher than the transition temperature of the uniform solution. While being kept at a temperature of more than 3° C. higher than the transition temperature of the uniform solution, the cell was passed under a metal halide lamp (80 W/cm$^2$) at a rate of 3.5 m/min. In this manner, the cell was irradiated with ultraviolet rays having an energy of 500 mJ/cm$^2$ so that the polymer-forming compound was cured to obtain a liquid crystal device having a light-control layer comprising a liquid crystal material and a transparent solid substance. A section of the cured material formed between the substrates in the liquid crystal device was observed under a scanning electron microscope. As a result, a transparent solid substance having a three-dimensional network structure formed by a polymer was recognized.

The light-scattering type liquid crystal display device thus obtained exhibited a wide operating temperature range, a response favorable for animation, a high contrast and a uniform display as compared with the conventional light-scattering type liquid crystal display devices. Thus, the light-scattering type liquid crystal display device thus obtained is useful for decorative display plate such as advertising display, display system such as watch, and projection display system.

EXAMPLE 29

A nematic liquid crystal composition (2-10) consisting of the following components:

Nematic Liquid Crystal Composition (2-10)

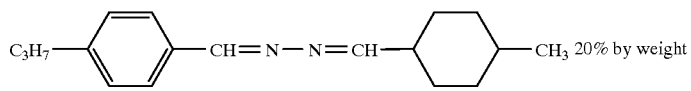
20% by weight

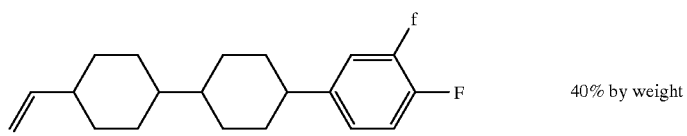
40% by weight

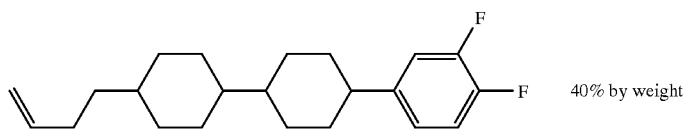
40% by weight was prepared. The liquid crystal composition was measured for various properties. The results were as follows:

$T_{N-1}$: 118.1° C.

$T \rightarrow_N$: −12.0° C.

$V_{th}$: 2.77 V

γ: 1.13

Δε: 4.0

Δn: 0.144

η: 21.4 c.p.

Specific resistivity before test: $6.1 \times 10^{11}$ Ω·cm

Specific resistivity after heat acceleration test: $5.2 \times 10^{11}$ Ω·cm

Voltage holding ratio before test: 98.4%

Voltage holding ratio after heat acceleration test: 97.9%

This nematic liquid crystal composition exhibits γ close to the limit (1.12) of the optical sharpness of liquid crystal display devices disclosed in "High Speed Liquid Crystal Technology", page 63, CMC. Accordingly, it can be understood that this liquid crystal composition is useful for high multiplexing driving.

Since this nematic liquid crystal composition exhibits a high specific resistivity and a high voltage holding ratio after heat acceleration test, it can be understood that this nematic liquid crystal composition is high stability to heat. A new nematic liquid crystal composition comprising this composition as an essential constituent material was prepared. This nematic liquid crystal composition was then used to prepare an active matrix liquid crystal display system. The liquid crystal display system was confirmed to be an excellent liquid crystal display system which show little current leakage and no flickering. Similarly, another nematic liquid crystal composition of the present invention comprising this composition as an essential constituent material was prepared. This nematic liquid crystal composition was then used to prepare a twisted nematic and super twisted nematic liquid crystal display systems. These nematic liquid crystal display systems were confirmed to be excellent liquid crystal display systems which show no flickering.

The foregoing nematic liquid crystal composition (2-11) comprises an azine compound incorporated in the following host liquid crystal (H).

The comparison of the foregoing liquid crystal compositions in properties shows that the liquid crystal composition of the present invention exhibits a greater birefringence index, a broader nematic phase temperature range and a smaller sharpness γ and thus gives better results.

EXAMPLE 30

A nematic liquid crystal composition (2-11) consisting of the following components:

Nematic Liquid Crystal Composition (2-11)

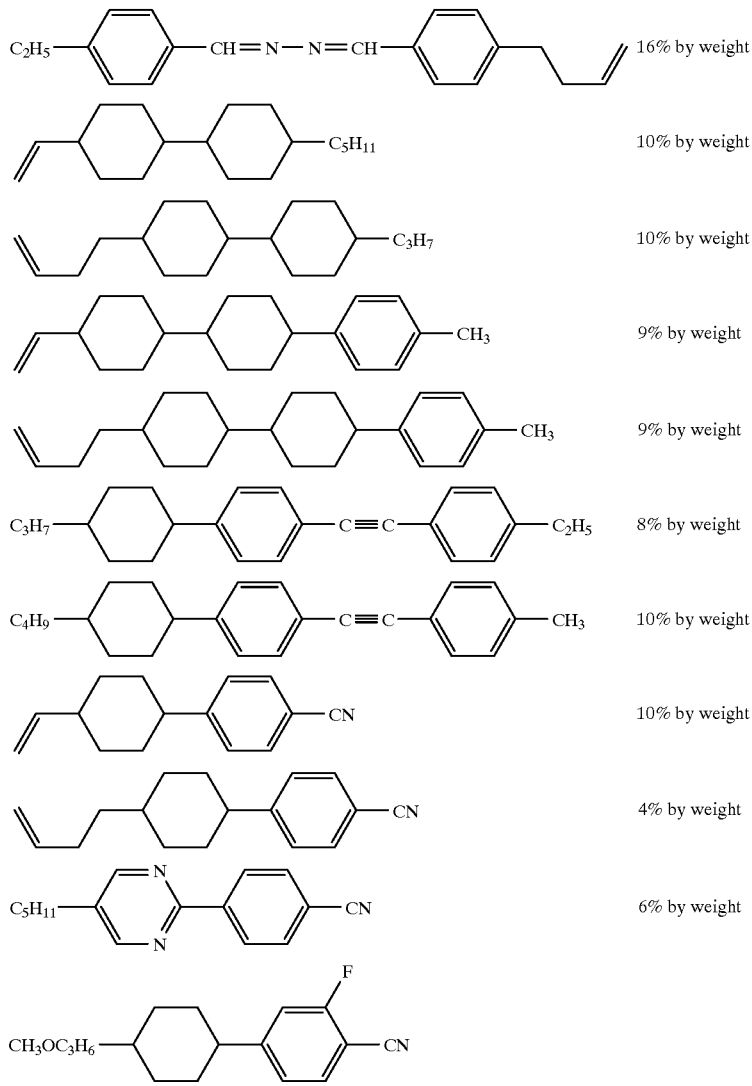

was prepared. The liquid crystal composition was measured for various properties. The results were as follows:

$T_{N-1}$: 101.1° C.
$T \to_N$: −70.0° C.
$V_{th}$: 2.19 V
Δε: 7.8
Δn: 0.172

To this nematic liquid crystal composition was then added a chiral substance "S-811" (available from Merck Co., Ltd.) to prepare a mixed liquid crystal. Separately, an organic film of "Sunever 610" (available from Nissan Chemical Industries, Ltd.) provided on opposing flat transparent electrodes was rubbed to form an alignment film. Thus, an STN-LCD display cell having a twist angle of 240° was prepared. The foregoing mixed liquid crystal was poured into the cell to prepare a liquid crystal display system which was then measured for display properties. As a result, a liquid crystal display system which exhibits excellent STN-LCD display properties, i.e., high multiplexing properties and improved fast response was obtained. The addition of the chiral substance was effected in such a manner that the inherent helical pitch P of the mixed liquid crystal and the cell thickness d of the display cell satisfy the following relationships:

Δn·d=0.85
d/P=0.53

STN-LCD Display Properties at Twist Angle of 240°

$V_{th}$: 2.40 V
γ: 1.024
Response (τr=τd): 15.6 msec. (static driving)

EXAMPLE 31

A nematic liquid crystal composition (2-12) consisting of the following components:

Nematic Liquid Crystal Composition (2-12)

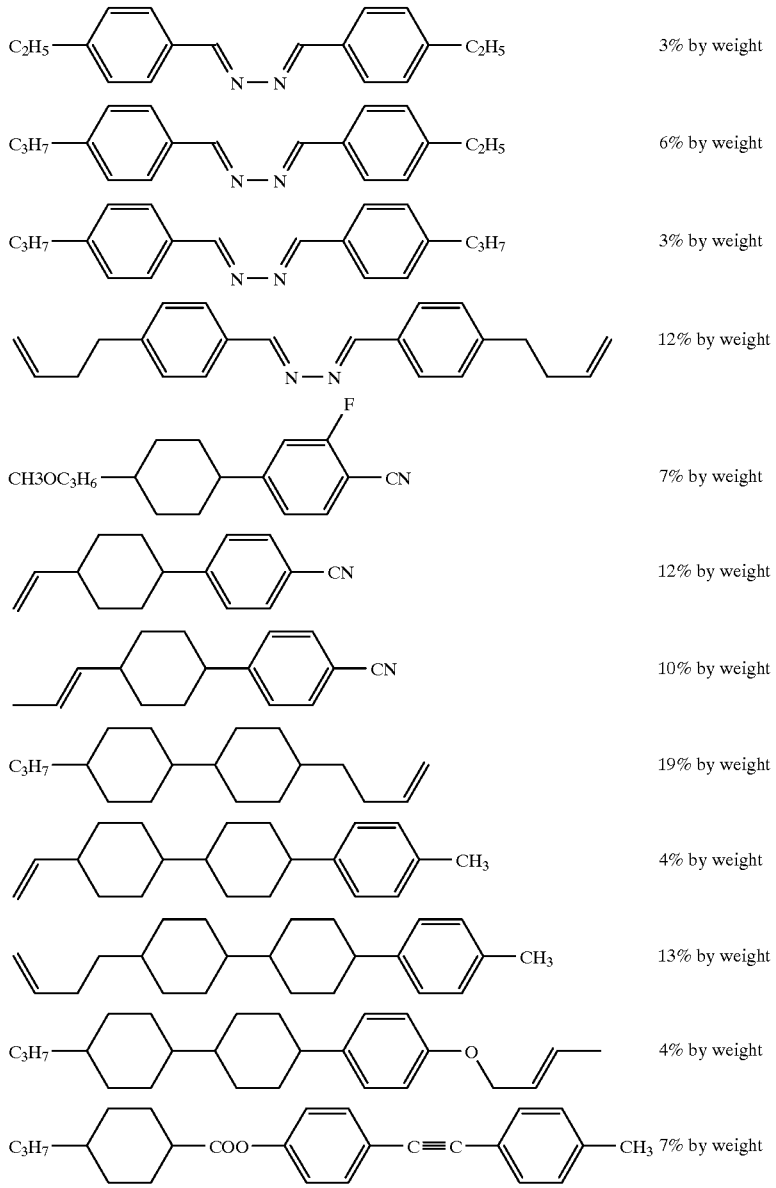

was prepared. The liquid crystal composition was measured for various properties. The results were as follows:

$T_{N-1}$: 101.7° C.
$T \to_N$: −30.0° C.
$V_{th}$: 2.16 V
Δε: 5.7
Δn: 0.167

To this nematic liquid crystal composition was then added a chiral substance "S-811" (available from Merck Co., Ltd.) to prepare a mixed liquid crystal. Separately, an organic film of "Sunever 610" (available from Nissan Chemical Industries, Ltd.) provided on opposing flat transparent electrodes was rubbed to form an alignment film. Thus, an STN-LCD display cell having a twist angle of 240° was prepared. The foregoing mixed liquid crystal was poured into the cell to prepare a liquid crystal display system which was then measured for display properties. As a result, a liquid crystal display system which exhibits excellent STN-LCD display properties, i.e., high multiplexing properties and improved fast response was obtained. The addition of the chiral substance was effected in such a manner that the inherent helical pitch P of the mixed liquid crystal and the cell thickness d of the display cell satisfy the following relationships:

Δn·d=0.85
d/P=0.51
STN-LCD Display Properties at Twist Angle of 240°
$V_{th}$: 2.46 V
γ: 1.024
Response (τr=τd): 19.0 msec. (static driving)
EXAMPLE 32
A nematic liquid crystal composition (2-13) consisting of the following components:
Nematic Liquid Crystal Composition (2-13)
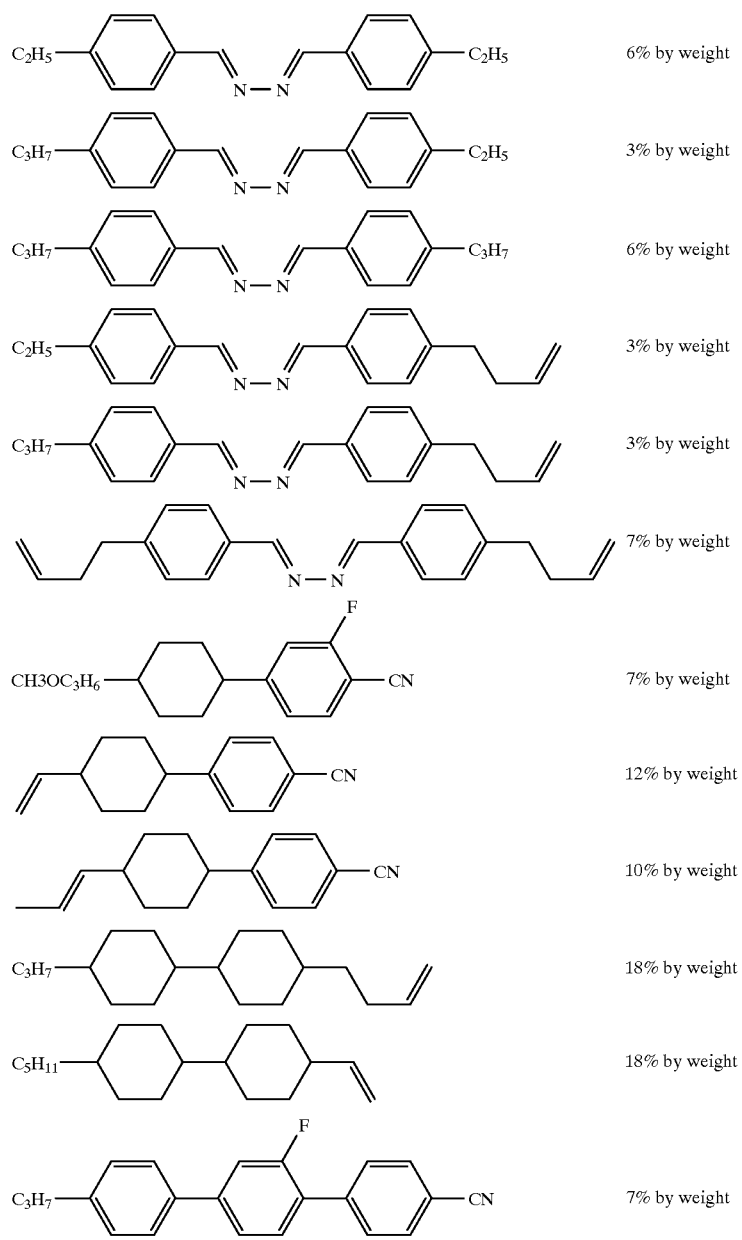

was prepared. The liquid crystal composition was measured for various properties. The results were as follows:

$T_{N-1}$: 83.8° C.
$T \to_N$: −31.0° C.
$V_{th}$: 1.89 V
γ: 1.14
Δε: 7.0
Δn: 0.172

To this nematic liquid crystal composition was then added a chiral substance "S-811" (available from Merck Co., Ltd.) to prepare a mixed liquid crystal. Separately, an organic film of "Sunever 610" (available from Nissan Chemical Industries, Ltd.) provided on opposing flat transparent electrodes was rubbed to form an alignment film. Thus, an STN-LCD display cell having a twist angle of 240° was prepared. The foregoing mixed liquid crystal was poured into the cell to prepare a liquid crystal display system which was a then measured for display properties. As a result, a liquid crystal display system which exhibits excellent STN-LCD display properties, i.e., high multiplexing properties and improved fast response was obtained. The addition of the chiral substance was effected in such a manner that the inherent helical pitch P of the mixed liquid crystal and the cell thickness d of the display cell satisfy the following relationships:

Δn·d=0.85
d/P=0.51

STN-LCD Display Properties at Twist Angle of 240°

$V_{th}$: 2.26 V
γ: 1.034
Response (τr=τd): 13.2 msec. (static driving)
55.0 msec. (1/240 duty driving)

EXAMPLE 33

A nematic liquid crystal composition (2-14) consisting of the following components:

The foregoing nematic liquid crystal composition was also measured for wavelength dispersion of birefringence index. As a result, the ratio of birefringence index at a wavelength of 400 nm to that at a wavelength of 650 nm was Nematic Liquid Crystal Composition (2-14)

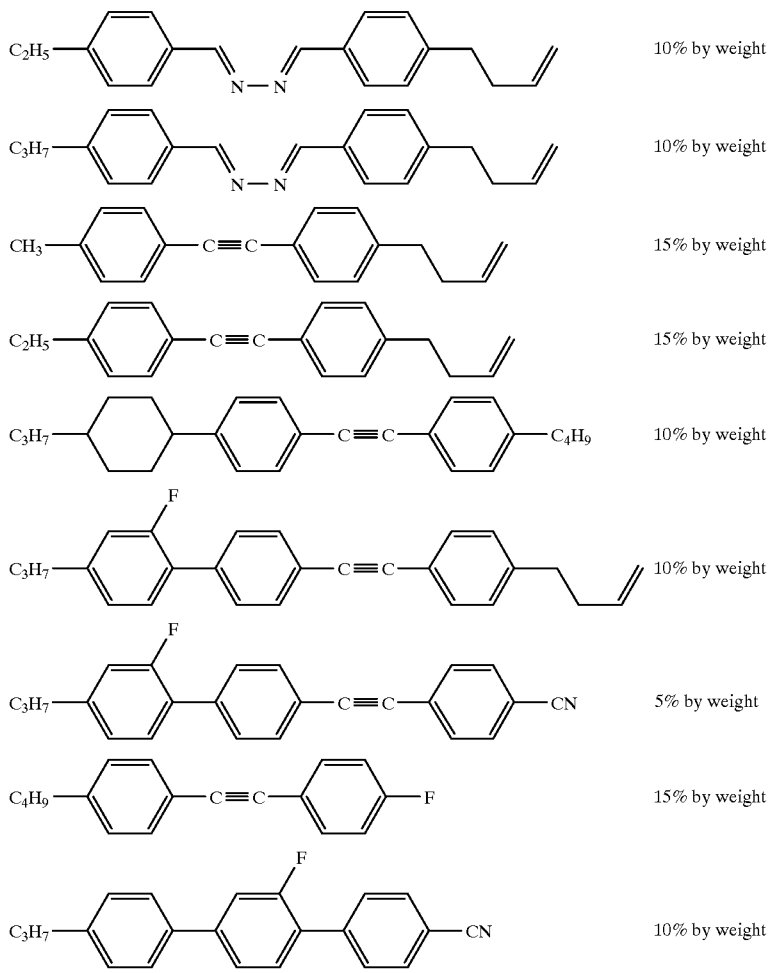

was prepared. The liquid crystal composition was measured for various properties. The results were as follows:

$T_{N\text{-}1}$: 95.4° C.
$T\rightarrow_N$: −10.0° C.
$V_{th}$: 2.48 V
γ: 1.15
Δε: 4.7
Δn: 0.290

This nematic liquid crystal composition was used to prepare TN-LCD having a cell thickness d of 1.7 μm. TN-LCD thus prepared was then measured for display properties. As a result, a liquid crystal display system which exhibits a threshold voltage of 2.20 V and a switching time of 1.2 msec. was obtained. not less than 1.15. Since this liquid crystal material exhibits a greater phase difference with different light wavelength, it is understood that this liquid crystal material is useful for a novel reflective type color liquid crystal display system utilizing birefringence of liquid crystal and retardation film which performs color display without any color filter layer.

EXAMPLE 34

The light-scattering type liquid crystal display device comprising the nematic liquid crystal composition (2-14) will be further described hereinafter, but the present invention should not be construed as being limited to these examples.

The liquid crystal composition (2-14) as a liquid crystal material, a polymer-forming compound "HX-220" (available from Nippon Kayaku Co., Ltd.), lauryl acrylate, and 2-hydroxy-2-methyl-1-phenylpropane-1-one were mixed in a proportion of 80%, 13.86%, 5.94% and 0.2%, respectively, to prepare a uniform solution of light-control layer-forming material. The light-control layer-forming material was then vacuum-injected into a 50×50 mm vacant cell, prepared from a pair of ITO electrode glass substrates having spacers with an average particle diameter of 10 μm, interposed therebetween at a temperature of more than 10° C. higher than the transition temperature of the uniform solution. While being kept at a temperature of more than 3° C. higher than the transition temperature of the uniform solution, the cell was passed under a metal halide lamp (80 W/cm²) at a rate of 3.5 m/min. In this manner, the cell was irradiated with ultraviolet rays having an energy of 500 mJ/cm² so that the polymer-forming compound was cured to obtain a liquid crystal device having a light-control layer comprising a liquid crystal material and a transparent solid substance. A section of the cured material formed between the substrates in the liquid crystal device was observed under a scanning electron microscope. As a result, a transparent solid substance having a three-dimensional network structure formed by a polymer was recognized.

The light-scattering type liquid crystal display device thus obtained exhibited a wide operating temperature range, a response favorable for animation, a high contrast and a uniform display as compared with the conventional light-scattering type liquid crystal display devices. Thus, the light-scattering type liquid crystal display device thus obtained is useful for decorative display plate such as advertising display, display system such as watch and projection display system.

EXAMPLE 35

A nematic liquid crystal composition (2-15) consisting of the following components:

Nematic Liquid Crystal Composition (2-15)

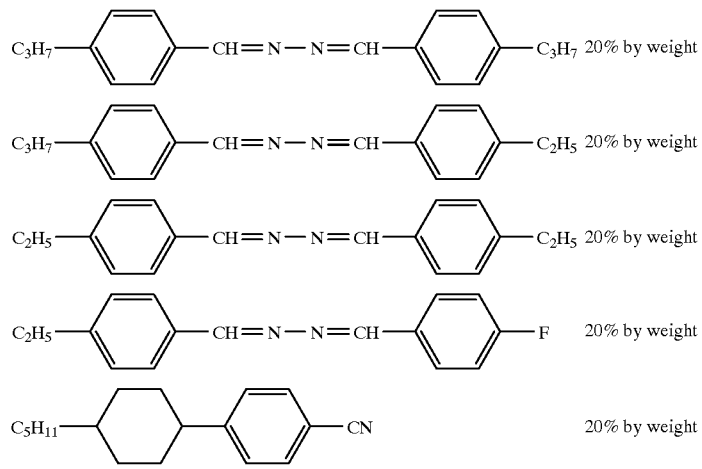

was prepared. The liquid crystal composition was measured for various properties. The results were as follows:

$T_{N\text{-}1}$: 92.4° C.
$T\rightarrow_N$: −0.0° C.
$V_{th}$: 2.55 V
γ: 1.15
Δε: 5.1
Δn: 0.280

This nematic liquid crystal composition was used to prepare TN-LCD having a cell thickness d of 1.8 μm. TN-LCD thus prepared was then measured for display properties. As a result, a liquid crystal display system which exhibits a threshold voltage of 2.23 V and a switching time of 1.0 msec. was obtained.

The foregoing nematic liquid crystal composition was also measured for wavelength dispersion of birefringence index. As a result, the ratio of birefringence index at a wavelength of 400 nm to that at a wavelength of 650 nm was not less than 1.15. Since this liquid crystal material exhibits a greater phase difference with different light wavelength, it is understood that this liquid crystal material is useful for a novel reflective type color liquid crystal display system utilizing birefringence of liquid crystal and retardation film which performs color display without any color filter layer.

To this nematic liquid crystal composition was then added a chiral substance "S-811" (available from Merck Co., Ltd.) to prepare a mixed liquid crystal. Separately, an organic film of "Sunever 610" (available from Nissan Chemical Industries, Ltd.) provided on opposing flat transparent electrodes was rubbed to form an alignment film. Thus, an STN-LCD display cell having a twist angle of 220° was prepared. The foregoing mixed liquid crystal was poured into the cell to prepare a liquid crystal display system which was then measured for display properties. As a result, a liquid crystal display system which exhibits excellent STN-LCD display properties, i.e., high multiplexing properties- and improved fast response was obtained. The addition of the chiral substance was effected in such a manner that the inherent helical pitch P of the mixed liquid crystal and the cell thickness d of the display cell satisfy the following relationships:

Δn·d=0.85
d/P=0.53

EXAMPLE 36

A nematic liquid crystal composition (2-16) consisting of the following components:

Nematic Liquid Crystal Composition (2-16)

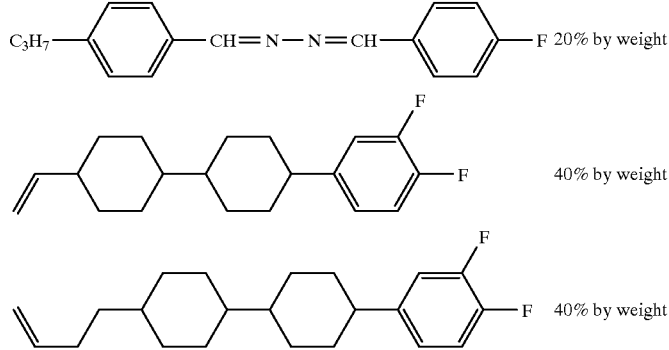

was prepared. The liquid crystal composition was measured for various properties. The results were as follows:

$T_{N-1}$: 103.9° C.
$T\rightarrow_{N}$: -0.0° C.
$V_{th}$: 2.28 V
γ: 1.13
Δε: 4.8
Δn: 0.143
η: 21.9 c.p.
Specific resistivity before test: $4.7\times10^{11}$ Ω·cm
Specific resistivity after heat acceleration test: $3.9\times10^{11}$ Ω·cm
Voltage holding ratio before test: 98.0%
Voltage holding ratio after heat acceleration test: 97.2%

This nematic liquid crystal composition exhibits γ close to the limit (1.12) of the optical sharpness of liquid crystal display devices disclosed in "High Speed Liquid Crystal Technology", page 63, CMC. Accordingly, it can be understood that this liquid crystal composition is useful for high multiplex driving.

Since this nematic liquid crystal composition exhibits a high specific resistivity and a high voltage holding ratio after heat acceleration test, it can be understood that this nematic liquid crystal composition is fast to heat. A new nematic liquid crystal composition comprising this composition as an essential constituent material was prepared. This nematic liquid crystal composition was then used to prepare an active matrix liquid crystal display system. The liquid crystal display system was confirmed to be an excellent liquid crystal display system which show little current leakage and no flickering. Similarly, another nematic liquid crystal composition of the present invention comprising this composition as an essential constituent material was prepared. This nematic liquid crystal composition was then used to prepare a twisted nematic and super twisted nematic liquid crystal display systems. These nematic liquid crystal display systems were confirmed to be excellent liquid crystal display systems which show no flickering.

The foregoing nematic liquid crystal composition (2-16) comprises an azine compound incorporated in the following host liquid crystal (H).

The comparison of the foregoing liquid crystal compositions in properties shows that the liquid crystal composition of the present invention exhibits a large birefringence index, a broader nematic phase temperature range and a smaller sharpness and thus gives better results. However, the foregoing azine compound exhibited a higher viscosity and thus showed a tendency to increase the viscosity of the host liquid crystal (H).

Despite the foregoing viscosity properties, a surprising fact was found. In other words, the liquid crystal composition (2-16) of the present invention and the host liquid crystal (H) were measured for response characteristics. The comparison of the response of these liquid crystals shows that the host liquid crystal composition (H) exhibits a switching time of 25.3 msec. while the liquid crystal composition (2-16) exhibits a switching time of 18.5 msec. and gives better results. It can be seen in the fact that despite its higher viscosity the foregoing azine compound exerts an effect of shortening the switching time. This effect gives an expectation that physical properties such as elastic constant and rotational viscosity of the azine compound have a specific tendency.

EXAMPLE 37

A nematic liquid crystal composition (2-17) consisting of the following components:

Nematic Liquid Crystal Composition (2-17)

| Structure | Amount |
|---|---|
| $C_2H_5$—⟨Ph⟩—CH=N—N=CH—⟨Ph⟩—F | 8% by weight |
| $C_3H_7$—⟨Ph⟩—CH=N—N=CH—⟨Ph⟩—F | 8% by weight |
| CH$_2$=CH—⟨Cy⟩—⟨Cy⟩—$C_5H_{11}$ | 10% by weight |
| CH$_2$=CH—CH$_2$—⟨Cy⟩—⟨Cy⟩—$C_3H_7$ | 10% by weight |
| CH$_2$=CH—⟨Cy⟩—⟨Cy⟩—⟨Ph⟩—$CH_3$ | 9% by weight |
| CH$_2$=CH—CH$_2$—⟨Cy⟩—⟨Cy⟩—⟨Ph⟩—$CH_3$ | 9% by weight |
| $C_3H_7$—⟨Cy⟩—⟨Ph⟩—C≡C—⟨Ph⟩—$C_2H_5$ | 8% by weight |
| $C_4H_9$—⟨Cy⟩—⟨Ph⟩—C≡C—⟨Ph⟩—$CH_3$ | 10% by weight |
| CH$_2$=CH—⟨Cy⟩—⟨Ph⟩—CN | 10% by weight |
| CH$_2$=CH—CH$_2$—⟨Cy⟩—⟨Ph⟩—CN | 4% by weight |
| $C_5H_{11}$—⟨Pyrimidine⟩—⟨Ph⟩—CN | 6% by weight |
| $CH_3OC_3H_6$—⟨Cy⟩—⟨Ph(F)⟩—CN | | was prepared. The liquid crystal composition was measured for various properties. The results were as follows:

$T_{N-1}$: 95.3° C.
$T \rightarrow_N$: −70.0° C.
$V_{th}$: 1.88 V
γ: 1.15
Δε: 9.0
Δn: 0.165

To this nematic liquid crystal composition was then added a chiral substance "S-811" (available from Merck Co., Ltd.) to prepare a mixed liquid crystal. Separately, an organic film of "Sunever 610" (available from Nissan Chemical Industries, Ltd.) provided on opposing flat transparent electrodes was rubbed to form an alignment film. Thus, an STN-LCD display cell having a twist angle of 220° was prepared. The foregoing mixed liquid crystal was poured into the cell to prepare a liquid crystal display system which was then measured for display properties. As a result, a liquid crystal display system which exhibits excellent STN-LCD display properties, i.e., high multiplexing properties and improved fast response was obtained. The addition of the chiral substance was effected in such a manner that the inherent helical pitch P of the mixed liquid crystal and the cell thickness d of the display cell satisfy the following relationships:

Δn·d 0.85
d/P=0.53

EXAMPLE 38

A nematic liquid crystal composition (2-18) consisting of the following components:

Nematic Liquid Crystal Composition (2-18)

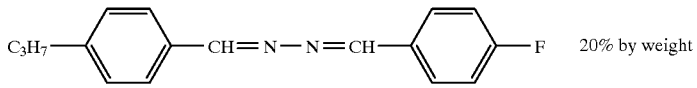 20% by weight

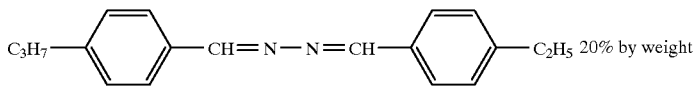 20% by weight

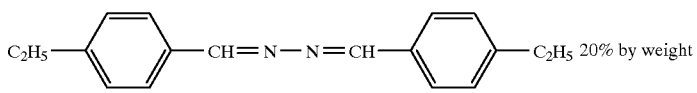 20% by weight

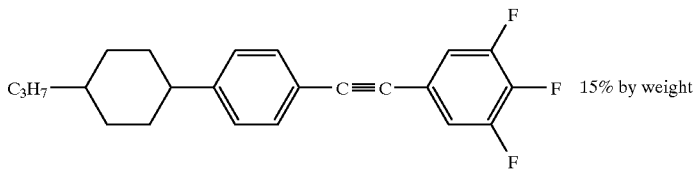 15% by weight

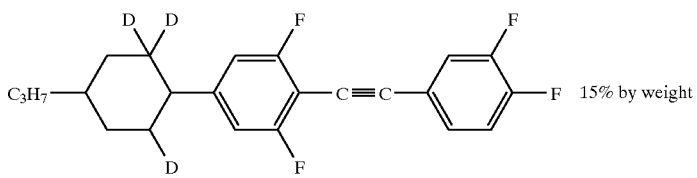 15% by weight

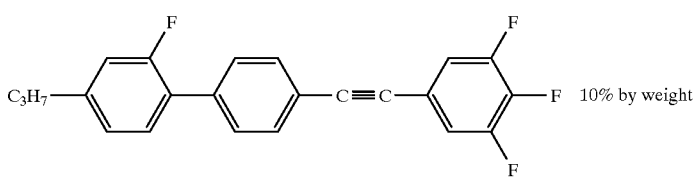 10% by weight was prepared. This liquid crystal composition exhibits a greater birefringence index, a broader nematic phase temperature range, a smaller sharpness and a fast response and thus gives better results.

The liquid crystal composition (2-18) as a liquid crystal material, a polymer-forming compound "HX-220" (available from Nippon Kayaku Co., Ltd.), lauryl acrylate, and 2-hydroxy-2-methyl-1-phenylpropane-1-one were mixed in a proportion of 80%, 13.86%, 5.94% and 0.2%, respectively, to prepare a uniform solution of light-control layer-forming material. The light-control layer-forming material was then vacuum-injected into a 50×50 mm vacant cell, prepared from a pair of ITO electrode glass substrates having spacers with an average particle diameter of 10 $\mu$m, interposed therebetween at a temperature of more than 10° C. higher than the transition temperature of the uniform solution. While being kept at a temperature of more than 3° C. higher than the transition temperature of the uniform solution, the cell was passed under a metal halide lamp (80 W/cm$^2$) at a rate of 3.5 nm/min. In this manner, the cell was irradiated with ultraviolet rays having an energy of 500 mJ/cm$^2$ so that the polymer-forming compound was cured to obtain a liquid crystal device having a light-control layer comprising a liquid crystal material and a transparent solid substance. A section of the cured material formed between the substrates in the liquid crystal device was observed under a scanning electron microscope. As a result, a transparent solid substance having a three-dimensional network structure formed by a polymer was recognized.

The light-scattering type liquid crystal display device thus obtained exhibited a wide operating temperature range, a response favorable for animation, a high contrast and a uniform display as compared with the conventional light-scattering type liquid crystal display devices. Thus, the light-scattering type liquid crystal display device thus obtained is useful for decorative display plate such as advertising display, display system such as watch and projection display system.
EXAMPLE 39
A nematic liquid crystal composition (2-19) consisting of the following components:
Nematic Liquid Crystal Composition (2-19)
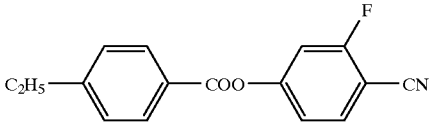  5% by weight
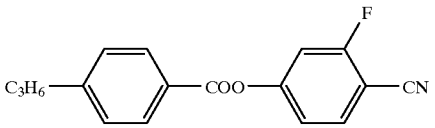  5% by weight
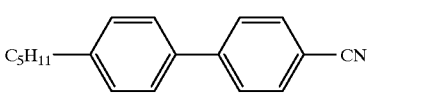  5% by weight
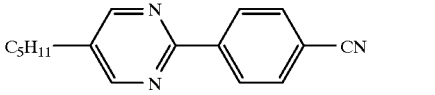  5% by weight
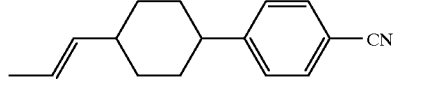  10% by weight
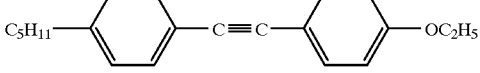  10% by weight
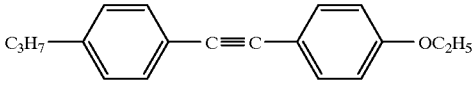  10% by weight
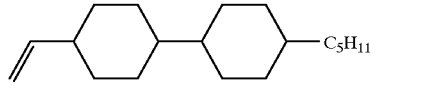  15% by weight
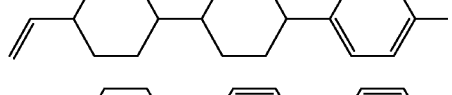  13% by weight
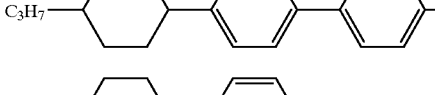  7% by weight
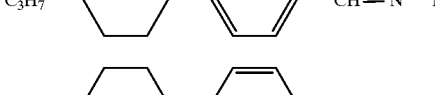  5% by weight
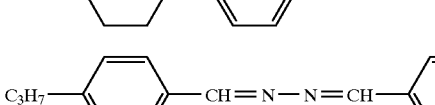  5% by weight
  5% by weight

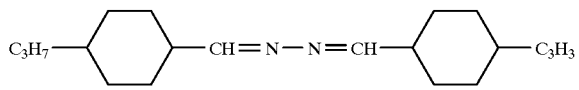 5% by weight was prepared. The liquid crystal composition was measured for various properties. The results were as follows:

$T_{N-1}$: 90.0° C.
$T \rightarrow_N$: −70.0° C.
$V_{th}$: 1.99 V
γ: 1.15
Δε: 8.8
Δn: 0.191

To this nematic liquid crystal composition was then added a chiral substance "S-811" (available from Merck Co., Ltd.) to prepare a mixed liquid crystal. Separately, an organic film of "Sunever 610" (available from Nissan Chemical Industries, Ltd.) provided on opposing flat transparent electrodes was rubbed to form an alignment film. Thus, an STN-LCD display cell having a twist angle of 240° was prepared. The foregoing mixed liquid crystal was poured into the cell to prepare a liquid crystal display system which was then measured for display properties. As a result, a liquid crystal display system which exhibits excellent STN-LCD display properties, i.e., high multiplexing properties and improved fast response was obtained. The addition of the chiral substance was effected in such a manner that the inherent helical pitch P of the mixed liquid crystal and the cell thickness d of the display cell satisfy the following relationships:

Δn·d=0.85
d/P=0.50

STN-LCD Display Properties at Twist Angle of 240°

$V_{th}$: 2.22 V
γ: 1.028
Response (τr=τd): 15.4 msec. (static driving)
81.0 msec. (1/240 duty driving)

The novel azine liquid crystal compound provided by the present invention exhibits a broad liquid crystal temperature range and an excellent solubility that causes little crystallization, can reduce the threshold voltage and respond at a high speed and causes no coloring as compared with known azine derivatives. In particular, the novel azine liquid crystal compound of the present invention can be used as a component of a practical liquid crystal material requiring a broad operating temperature range and a fast response.

Further, the preparation process of the present invention makes it possible to easily and selectively produce asymmetric azines containing these novel azine compounds.

Moreover, the nematic liquid crystal composition of the present invention exhibits a great birefringence index Δn, a high voltage holding ratio and a high chemical stability, stays in nematic phase in a broad temperature range and exerts an excellent effect of improving fast response and thus can be used in twisted nematic or super twisted nematic liquid crystal display systems.

Further, a liquid crystal display device which utilizes birefringence of liquid crystal layer and retardation film to make color display can be provided. In particular, because of its great birefringence index, the liquid crystal dyisplay device of the present invention can comprise a liquid crystal layer having a reduced thickness that can improve fast response, making it possible to make display of a large amount of data. Moreover, a device can be provided useful for a light-scattering type liquid crystal a display system having a light-control layer comprising a liquid crystal material and a transparent solid substance.

What is claimed is:

1. A compound, represented by the following general formula (I):

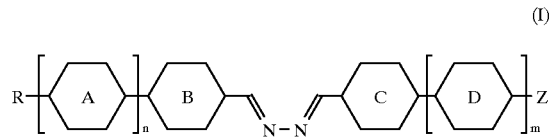

wherein m and n each independently represent an integer of 0 or 1;

rings A, B, C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group;

R represents a $C_{2-12}$ alkyl group, alkoxyl group, alkenyl group or alkoxylalkyl group or $C_{3-12}$ alkenyloxy group; and z represents a fluorine atom, chlorine atom, bromine atom, cyano group, —OCF$_3$, —OCF$_2$H, —CF$_3$, —OCH$_2$CF$_3$, $C_{1-12}$ alkyl group or alkoxyl group, $C_{2-12}$ alkenyl group or alkoxylalkyl group or $C_{3-12}$ alkenyloxy group, with the proviso that Z is not an alkyl group, cyano group, fluorine atom, chlorine atom or bromine atom when m and n each are 0 and rings B and C each are 1,4-phenylene group and R is an alkyl group.

2. The compound according to claim 1, wherein m and n are 0 at the same time and rings B and C each independently represent 1,4-phenylene group which may be substituted by fluorine atom, with the proviso that at least one of rings B and C is substituted by fluorine atom when R represents a $C_{2-12}$ alkyl group and Z represents a fluorine atom, chlorine atom, bromine atom or $C_{1-12}$ alkyl group.

3. The compound according to claim 2, wherein R represents a $C_{2-12}$ alkenyl group, Z represents a $C_{1-7}$ straight-chain alkyl group, $C_{2-12}$ alkenyl group or fluorine atom and rings B and C each represent 1,4-phenylene group which may be substituted by fluorine atom.

4. The compound according to claim 2, wherein R represents a $C_{2-7}$ straight-chain alkyl group, Z represents a fluorine atom or —OCF$_3$ and rings B and C each represents 1,4-phenylene group which may be substituted by fluorine atom.

5. The compound according to claim 1, wherein n represents 1, m represents 0, R represents a $C_{2-7}$ straight-chain alkyl group or $C_{2-7}$ straight-chain alkenyl group, rings B and C each represent 1,4-phenylene group which may be substituted by fluorine atom and Z represents a fluorine atom, trifluoromethoxy group, $C_{1-7}$ straight-chain alkyl group or $C_{4-7}$ straight-chain alkenyl group.

6. The compound according to claim 1, wherein m and n are 0 at the same time, ring B represents trans-1,4-cyclohexylene group and ring C represents 1,4-phenylene group which may be substituted by fluorine atom or trans-1,4-cyclohexylene group.

7. A process for the preparation of a compound represented by the general formula (I):

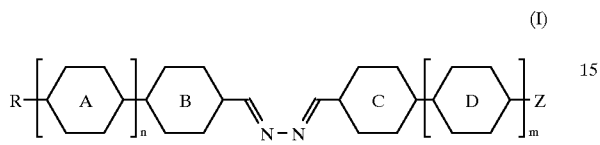

(I)

wherein m and n each independently represent an integer of 0 or 1; rings A, B, C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; R represents a $C_{1-12}$ alkyl group or alkoxyl group, $C_{2-12}$ alkenyl group or alkoxylalkyl group or $C_{3-12}$ alkenyloxy group; and Z represents a fluorine atom, chlorine atom, bromine atom, cyano group, —$OCF_3$, —$OCF_2H$, —$CF_3$, —$OCH_2CF_3$, $C_{1-12}$ alkyl group or alkoxyl group, $C_{2-12}$ alkenyl group or alkoxylalkyl group or $C_{3-12}$ alkenyloxy group, which comprises allowing a compound represented by the following general formula (II):

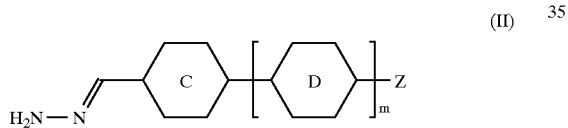

(II)

wherein Z represents a fluorine atom, chlorine atom, bromine atom, cyano group, —$OCF_3$, —$OCF_2H$, —$CF_3$, —$OCH_2CF_3$, $C_{1-12}$ alkyl group or alkoxyl group, $C_{2-12}$ alkenyl group or alkoxylalkyl group or $C_{3-12}$ alkenyloxy group; rings C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; and m represents an integer of 0 or 1
and a compound represented by the following general formula (III):

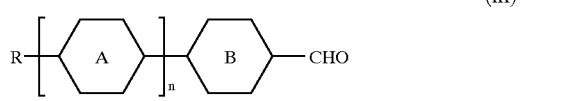

(III)

wherein R represents a $C_{1-12}$ alkyl group or alkoxyl group, $C_{2-12}$ alkenyl group or alkoxylalkyl group or $C_{3-12}$ alkenyloxy group; rings A and B each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; and n represents an integer of 0 or 1
to undergo reaction in the presence of an amine.

8. A process for the preparation of a compound represented by the general formula (I):

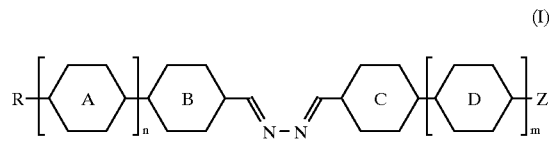

(I)

wherein m and n each independently represent an integer of 0 or 1; rings A, B, C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; R represents a $C_{1-12}$ alkyl group or alkoxyl group, $C_{2-12}$ alkenyl group or alkoxylalkyl group or $C_{3-12}$ alkenyloxy group; and Z represents a fluorine atom, chlorine atom, bromine atom, cyano group, —$OCF_3$, —$OCF_2H$, —$CF_3$, —$OCH_2CF_3$, $C_{1-12}$ alkyl group or alkoxyl group, $C_{2-12}$ alkenyl group or alkoxylalkyl group or $C_{3-12}$ alkenyloxy group,
which comprises allowing a compound represented by the following general formula (IV):

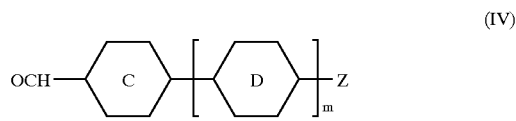

(IV)

wherein Z represents a fluorine atom, chlorine atom, bromine atom, cyano group, —$OCF_3$, —$OCF_2H$, —$CF_3$, —$OCH_2CF_3$, $C_{1-12}$ alkyl group or alkoxyl group, $C_{2-12}$ alkenyl group or alkoxylalkyl group or $C_{3-12}$ alkenyloxy group; rings C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; and m represents an integer of 0 or 1
and a compound represented by the following general formula (V):

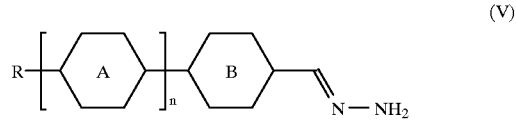

(V)

wherein R represents a $C_{1-12}$ alkyl group or alkoxyl group, $C_{2-12}$ alkenyl group or alkoxylalkyl group or $C_{3-12}$ alkenyloxy group; rings A and B each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group; and n represents an integer of 0 or 1
to undergo reaction in the presence of an amine.

9. A nematic liquid crystal composition, comprising a compound represented by the general formula (I):

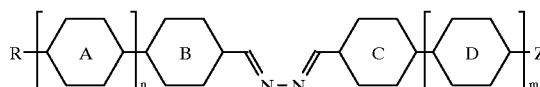

(I)

wherein m and n each independently represent an integer of 0 or 1;

rings A, B, C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group;

R represents a $C_{1-12}$ alkyl group or alkoxyl group, $C_{2-12}$ alkenyl group or alkoxylalkyl group or $C_{3-12}$ alkenyloxy group; and Z represents a fluorine atom, chlorine atom, bromine atom, cyano group, —$OCF_3$, —$OCF_2H$, —$CF_3$, —$OCH_2CF_3$, $C_{1-12}$ alkyl group or alkoxyl group, $C_{2-12}$ alkenyl group or alkoxylalkyl group or $C_{3-12}$ alkenyloxy group, with the proviso that Z is not an alkyl group, cyano group, fluorine atom, chlorine atom or bromine atom when m and n each are 0 and rings B and C each are 1,4-phenylene group and R is an alkyl group.

10. The nematic liquid crystal composition according to claim 9 wherein m and n are 0 at the same time and rings B and C each independently represent 1,4-phenylene group which may be substituted by fluorine atom, with the proviso that at least one of rings B and C is substituted by fluorine atom when R represents a $C_{1-12}$ alkyl group and Z represents a fluorine atom, chlorine atom, bromine atom or $C_{1-12}$ alkyl group.

11. The nematic liquid crystal composition according to claim 9, wherein R represents a $C_{2-12}$ alkenyl group, Z represents a $C_{1-7}$ straight-chain alkyl group, $C_{2-12}$ alkenyl group or fluorine atom and rings B and C each represent 1,4-phenylene group which may be substituted by fluorine atom.

12. The nematic liquid crystal composition according to claim 9, wherein R represents a $C_{1-7}$ straight-chain alkyl group, Z represents a fluorine atom or —$OCF_3$ and rings B and C each represents 1,4-phenylene group which may be substituted by fluorine atom.

13. The nematic liquid crystal composition according to claim 9, wherein n represents 1, m represents 0, R represents a $C_{1-7}$ straight-chain alkyl group or $C_{2-7}$ straight-chain alkenyl group, rings B and C each represent 1,4-phenylene group which may be substituted by fluorine atom and Z represents a fluorine atom, trifluoromethoxy group, $C_{1-7}$ straight-chain alkyl group or $C_{4-7}$ straight-chain alkenyl group.

14. The nematic liquid crystal composition according to claim 9, wherein m and n are 0 at the same time, ring B represents trans-1,4-cyclohexylene group and ring C represents 1,4-phenylene group which may be substituted by fluorine atom or trans-1,4-cyclohexylene group.

15. A nematic liquid crystal composition, comprising as a liquid crystal component A a compound represented by the general formula (I):

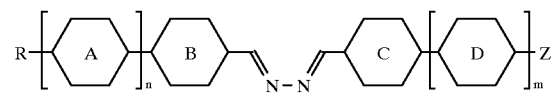

(I)

wherein m and n each independently represent an integer of 0 or 1;

rings A, B, C and D each independently represent 1,4-phenylene group which may be substituted by fluorine atom, trans-1,4-cyclohexylene group, pyrimidine-2,5-diyl group, pyridine-2,5-diyl group, pyrazine-2,5-diyl group, pyridazine-3,6-diyl group or trans-1,3-dioxane-2,5-diyl group;

R represents a $C_{1-12}$ alkyl group or alkoxyl group, $C_{2-12}$ alkenyl group or alkoxylalkyl group or $C_{3-12}$ alkenyloxy group; and z represents a fluorine atom, chlorine atom, bromine atom, cyano group, —$OCF_3$, —$OCF_2H$, —$CF_3$, —$OCH_2CF_3$, $C_{1-12}$ alkyl group or alkoxyl group, $C_{2-12}$ alkenyl group or alkoxylalkyl group or $C_{3-12}$ alkenyloxy group and as a liquid crystal component B a compound having a dielectric anisotropy of not less than +2, wherein as said liquid crystal component B there is incorporated a compound selected from the group consisting of compounds represented by the following general formulae (II-1) to (II-4):

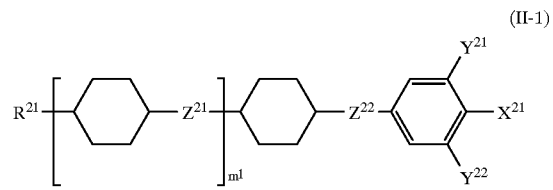

(II-1)

(II-2)

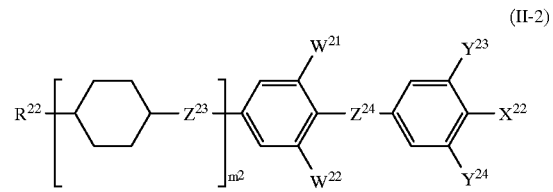

(II-3)

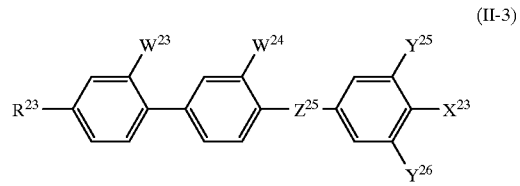

(II-4)

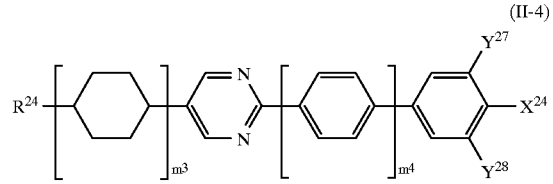

wherein $R^{21}$ to $R^{24}$ each independently represent a $C_{2-10}$ straight-chain alkyl group, alkenyl group or $C_sH_{2s+1}$—O—$C_tH_{2t}$ in which s and t each independently represent an integer of from 1 to 5;

$X^{21}$ to $X^{24}$ each independently represent a fluorine atom, chlorine atom, —$OCF_3$, —$OCHF_2$, —$CF_3$ or —CN;

$Y^{21}$ to $Y^{29}$ each independently represent a hydrogen atom or fluorine atom;

$W^{21}$ to $W^{24}$ each independently represent a hydrogen atom or fluorine atom;

$Z^{21}$ to $Z^{23}$ each independently represent a single bond, —COO—, —CH$_2$CH$_2$— or —(CH$_2$)$_4$—;

$Z^{21}$ may also represent —C≡C— or —CH═CH—;

$Z^{24}$ and $Z^{25}$ each independently represent a single bond, —COO—, —C≡C— or —CF═CF—; and $m^1$ to $m^4$ each independently represent an integer of from 0 or 1, with the proviso that $m^3+m^4$ make an integer of 0 or and hydrogen atoms in the cyclohexane ring in the compounds (II-1) to (II-4) may be replaced by deuterium atoms (D).

16. The nematic liquid crystal composition according to claim 15 further comprising as a liquid crystal component C a compound having a dielectric anisotropy of from −2 to +2, wherein as said liquid crystal component C there is incorporated a compound selected from the group consisting of compounds represented by the following general formulae (III-1) to (III-4):

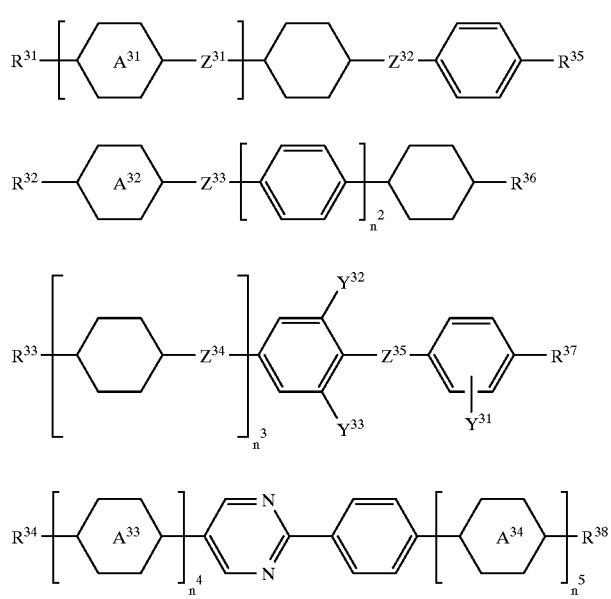

(III-1)

(III-2)

(III-3)

(III-4)

wherein
R$^{31}$ to R$^{34}$ each independently represent a C$_{2-7}$ straight-chain alkyl group or alkenyl group;

R$^{35}$ to R$^{38}$ each independently represent a C$_{1-7}$ straight-chain alkyl group, alkoxy group, alkenyl group, alkenyloxy group or C$_u$H$_{2u+1}$—O—C$_v$H$_{2v}$ in which u and v each independently represent an integer of from 1 to 5;

Y$^{31}$ represents a hydrogen atom, fluorine atom or —CH$_3$;

Y$^{32}$ and Y$^{33}$ each independently represent a hydrogen atom or fluorine atom;

Z$^{31}$ to Z$^{34}$ each independently represent a single bond, —COO—, —CH$_2$CH$_2$— or —(CH$_2$)$_4$—;

Z$^{31}$ may also represent —C≡C— or —CH═CH—;

Z$^{35}$ represents a single bond, —C≡C—, —COO— or —CF═CF—;

rings A$^{31}$ and A$^{32}$ each independently represent a cyclohexane ring or cyclohexene ring;

rings A$^{33}$ and A$^{34}$ each independently represent a cyclohexane ring or benzene ring; and n$^1$ to n$^5$ each independently represent an integer of 0 or 1, with the proviso that n$^4$+n$^5$ make an integer of 0 or 1, and hydrogen atoms in the cyclohexane ring in the compounds (III-1) to (III-4) may be replaced by deuterium atoms (D).

17. The nematic liquid crystal composition according to claim 15, comprising a compound represented by the general formula (I"):

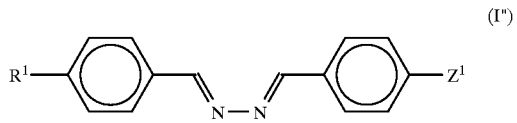

(I")

wherein R$^1$ represents a C$_{1-10}$ alkyl group, alkoxyl group or hydrogen atom; and Z$^1$ represents a C$_{1-10}$ alkyl group, alkoxyl group, fluorine atom, chlorine atom, cyano group or hydrogen atom.

18. The nematic liquid crystal composition according to claim 15, comprising a compound represented by the general formula (I'''):

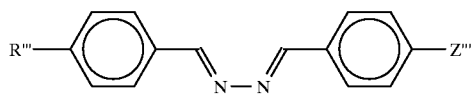

(I''')

wherein R''' and Z''' each independently represent a C$_{1-10}$ alkyl group or C$_{2-7}$ alkenyl group.

19. An active matrix, twisted nematic or super twisted nematic liquid crystal display system, comprising a nematic liquid crystal composition according to any one of claims 9, 15, 16, 17 and 18.

20. A light-scattering type liquid crystal display system, comprising a light-control layer having a nematic liquid crystal composition according to any one of claims 9, 15, 16, 17 and 18.

* * * * *